US012746049B2

(12) United States Patent
Biester et al.

(10) Patent No.: US 12,746,049 B2
(45) Date of Patent: Sep. 29, 2026

(54) DEVICES AND METHODS FOR CUTTING SURGICAL COMPONENTS

(71) Applicant: MEDOS INTERNATIONAL SARL, Le Locle (CH)

(72) Inventors: Eric Biester, Barrington, RI (US); Michael Sorrenti, Middleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 207 days.

(21) Appl. No.: 18/390,645

(22) Filed: Dec. 20, 2023

(65) Prior Publication Data

US 2024/0206934 A1 Jun. 27, 2024

Related U.S. Application Data

(60) Provisional application No. 63/434,820, filed on Dec. 22, 2022.

(51) Int. Cl.
*A61B 17/88* (2006.01)

(52) U.S. Cl.
CPC ................................ *A61B 17/8863* (2013.01)

(58) Field of Classification Search
CPC ............ A61B 17/7088; A61B 17/7086; A61B 17/7085; A61B 17/7083; A61B 17/7089; A61B 17/8863; A44B 13/02; F16B 45/024
See application file for complete search history.

(56) References Cited

U.S. PATENT DOCUMENTS

| | | | | |
|---|---|---|---|---|
| 208,250 A * | 9/1878 | Main | F16B 45/024 24/599.8 |
| 1,032,369 A * | 7/1912 | Baxter | F16B 45/024 24/599.6 |
| 1,102,162 A | 6/1914 | Norman | |
| 1,706,460 A | 3/1929 | Norling | |

(Continued)

FOREIGN PATENT DOCUMENTS

| | | | | |
|---|---|---|---|---|
| DE | 10128596 A1 * | 12/2002 | A61B 17/8863 |
| ES | 1293277 Y | 10/2022 | |

OTHER PUBLICATIONS

Machine translation of DE-10128596-A1. (Year: 2025).*
International Search Report and Written Opinion for Application No. PCT/EP2023/086864 mailing Mar. 21, 2024 (16 pages).

*Primary Examiner* — Amy R Sipp
(74) *Attorney, Agent, or Firm* — Flaster Greenberg PC

(57) ABSTRACT

Surgical instruments for cutting surgical components either in situ or ex situ are disclosed. The surgical instruments can include a translating anvil that can be driven relative to an outer sleeve by a rotating an inner sleeve relative to the outer sleeve. The outer sleeve can be separable into a distal tip and a proximal base tube that can be modularly coupled to one another and selectively locked against separation. A distal portion of the outer sleeve can include a hooked shape with an opening to receive a rod or other component therein that can be selectively closed by a pivoting capture arm. Actuation of the instrument can occur by manual user power or by powered instrument, such as a driver. The outer sleeve can interface with additional instruments or components, such as a counter-torque handle, to prevent rotation thereof during actuation of the inner sleeve relative thereto.

13 Claims, 38 Drawing Sheets

(56) References Cited

U.S. PATENT DOCUMENTS

| | | | | |
|---|---|---|---|---|
| 1,790,056 | A * | 1/1931 | Moody | E21B 19/04 294/82.2 |
| 2,558,641 | A | 6/1951 | Beezley | |
| 2,688,185 | A | 9/1954 | Brazil et al. | |
| 2,879,592 | A | 3/1959 | Paul | |
| 8,124,454 | B1 | 2/2012 | Chu et al. | |
| 8,127,454 | B1 | 3/2012 | Gao | |
| 2001/0027320 | A1 | 10/2001 | Sasso | |
| 2009/0062858 | A1* | 3/2009 | Dziedzic | A61B 17/1757 606/103 |
| 2009/0318944 | A1* | 12/2009 | Kimura | A61B 17/320068 606/169 |
| 2011/0295252 | A1 | 12/2011 | Tipirneni et al. | |
| 2015/0265303 | A1 | 9/2015 | Schwab et al. | |
| 2022/0280207 | A1 | 9/2022 | Biester et al. | |

* cited by examiner

DEVICES AND METHODS FOR CUTTING SURGICAL COMPONENTS

CROSS-REFERENCE TO RELATED APPLICATIONS

This application claims the benefit of U.S. Provisional Application No. 63/434,820, filed on Dec. 22, 2022. The entire contents of this application are incorporated by reference herein.

FIELD

This disclosure relates generally to surgical instruments used for cutting surgical components, such as various implants including spinal fixation rods and plates, and related methods of use.

BACKGROUND

Fixation systems used in spinal surgery include various types of implants. For example, bone anchors can be implanted in vertebrae of a patient's spine with a rod positioned therebetween to provide stability. To fit the spinal rod to a particular fixation construct, the rod can be bent, cut, or otherwise manipulated. The implants can be made from a hard material to withstand the forces experienced in the spine, which can make the rod difficult to cut, both in situ and ex situ, such as on a back table in an operating room.

Conventional rod cutting instruments can have several shortcomings. For example, rod cutters, whether suited for use in situ or at a back table, etc., often have handles with long arms to achieve mechanical advantage, as they often cut the rod using a pinching or shearing action with opposed moving dies coupled to the handles. These handles, which can be as much as two or three feet in length, can require a large amount of force to actuate and can lack precision as a result. The application of a high amount of energy by a user in an uncontrolled manner can be undesirable.

Accordingly, there is a need for improved cutting devices that can be used to cut surgical components, such as spinal fixation rods, plates, other implants, etc., in a more controlled and ergonomic fashion.

SUMMARY

Disclosed herein are devices and methods for cutting surgical components, such as spinal rods and plates or other implants, either in situ or ex situ. The devices disclosed herein can cut implants in a more controlled fashion than traditional double action bolt cutters or shearing rod cutters. The devices disclosed herein can be modular in nature, providing options for cutting different types and/or sizes of surgical components. The devices disclosed herein can utilize different actuation power sources, including user-powered actuation or actuation from a powered instrument, such as a driver. Some non-limiting examples of surgical components that can be cut by the cutting devices disclosed herein can include spinal rods, trauma plates, craniomaxillofacial (CMF) plates, and so forth. One embodiment of a cutting instrument can include a translating anvil that can be driven relative to an outer sleeve by a rotating inner sleeve relative to the outer sleeve. The outer sleeve can be unitary in some embodiments and, in other embodiments, can be separable into a distal tip and a proximal base tube that are configured to be modularly coupled to one another and selectively locked against separation. Regardless of modularity, a distal portion of the outer sleeve can include a hooked shape with an opening to receive a rod or other component therein. The opening can be selectively closed by a pivoting capturing arm in a manner similar to a carabiner in order to facilitate receiving and securing a surgical component relative to the distal tip. Once a surgical component is situated within the distal tip, the threaded inner sleeve can be rotated relative to the outer sleeve to distally translate the anvil and cut the surgical component. The outer sleeve and/or the threaded inner sleeve can include surface features thereon for interfacing with one or more additional instruments or components. For example, a counter-torque handle can be coupled to the outer sleeve to prevent rotation thereof during actuation of the inner sleeve relative thereto. Moreover, in some embodiments, a hex socket and/or a powered drill can be coupled to the inner sleeve to rotate it relative to the outer sleeve.

In one aspect, a surgical instrument is disclosed that can include an outer sleeve, as well as an opening formed in a sidewall of the outer sleeve. The outer sleeve can have a lumen that extends therethrough and the opening can be configured to receive at least a portion of an implant therethrough. The instrument can further include a capture arm disposed within the opening, as well as an inner sleeve disposed in the lumen of the outer sleeve and an anvil disposed in the lumen of the outer sleeve distal to the inner sleeve. The capture arm can be pivotably coupled to the outer sleeve and configured to selectively expose the opening to allow the implant to pass therethrough. The inner sleeve can be configured to rotate relative to the outer sleeve and the anvil can be configured to translate without rotating relative to the outer sleeve to cut the implant.

Any of a variety of alternative or additional features can be included and are considered within the scope of the present disclosure. For example, in some embodiments, the inner sleeve can include a threaded surface on at least a portion thereof that is configured to engage with a corresponding threaded surface on an inner surface of the outer sleeve.

In certain embodiments, the inner sleeve can be configured to rotate relative to the outer sleeve to translate the anvil distally with respect to the outer sleeve. In some embodiments, the anvil can further include a cutting tip at a distal end thereof for cutting the implant. The cutting tip can be V-shaped. In certain embodiments, the anvil can include a groove formed along a length thereof. The instrument can further include a pin that passes through the outer sleeve and is disposed in the groove of the anvil to prevent rotation of the anvil during translation. In some embodiments, the anvil can include a coating that is configured to enhance a hardness thereof.

In certain embodiments, the implant can include one or more of a spinal rod, a trauma plate, or a CMF plate. The capture arm can be configured to pivot to expose the opening in response to a force applied to the capture arm by the implant. In some embodiments, the capture arm can be biased to be disposed within the opening. In certain embodiments, the capture arm can be biased by a spring disposed in a channel formed in the capture arm that exerts a radially outward force onto the capture arm.

In certain embodiments, the instrument can further include a pocket formed on an inner surface of a sidewall of the pouter sleeve opposite the opening. The pocket can be configured to receive the capture arm when the capture arm selectively exposes the opening. In some embodiments, the instrument can further include a counter-torque handle configured to mate with the outer sleeve to prevent rotation of the outer sleeve during rotation of the inner sleeve.

In certain embodiments, the outer sleeve can include a sharpened edge positioned to contact an implant on an opposite side from the anvil. In some embodiments, a proximal end of the inner sleeve can include a drive feature configured to couple with a torque application device to facilitate rotation of the inner sleeve.

In certain embodiments, the outer sleeve can include a base tube and a distal tip configured to be modularly coupled to one another and selectively locked against separation. A distal end of the base tube can include a reduced diameter portion configured to be received within a reduced diameter portion of a proximal end of the distal tip. In certain embodiments, the distal tip can include a snap lock configured to interface with a slot of the base tube to selectively lock against separation of the distal tip and base tube. In some embodiments, the opening can be formed in the distal tip. The capture arm can be pivotably coupled to the distal tip. In some embodiments, the inner sleeve can be configured to translate relative to the outer sleeve.

In another aspect, a surgical method is disclosed that can include contacting an implant against a capture arm on a side of a cutting instrument outer sleeve to pivot the capture arm and expose an opening to an implant-receiving portion of the cutting instrument, passing the implant through the opening and into the implant-receiving portion of the cutting instrument; and rotating an inner sleeve of the cutting instrument relative to the outer sleeve to distally translate an anvil through the implant.

As with the above-noted embodiments, any of a variety of alternative or additional features can be included and are considered within the scope of the present disclosure. For example, in some embodiments, the method can further include coupling a driver to a proximal portion of the inner sleeve. The driver can be powered and rotating the inner sleeve can further include actuating the powered driver.

In some embodiments, the method can further include coupling a counter-torque handle to the outer sleeve to prevent rotation of the outer sleeve during rotation of the inner sleeve. In certain embodiments, pivoting the capture arm can include passing a distal end of the capture arm into a pocket formed in a sidewall of the cutting instrument opposite the opening. In some embodiments, the method can further include pivoting the capture arm to block the opening after passing the implant through the opening.

In certain embodiments, the method can further include assembling the outer sleeve by coupling a modular distal tip with a base tube prior to contacting the implant against the capture arm. In some embodiments, coupling the modular distal tip with the base tube can further include inserting a reduced diameter portion of a distal end of the base tube into a reduced-diameter portion of a proximal end of the distal tip. Coupling the modular distal tip with the base tube can further include rotating the distal tip and base tube relative to one another to engage a lock against separation thereof. In certain embodiments, the implant can include one or more of a spinal rod, a trauma plate, or a CMF plate.

Any of the features or variations described herein can be applied to any particular aspect or embodiment of the present disclosure in a number of different combinations. The absence of explicit recitation of any particular combination is due solely to avoiding unnecessary length or repetition.

DETAILED DESCRIPTION

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Figure 1A:
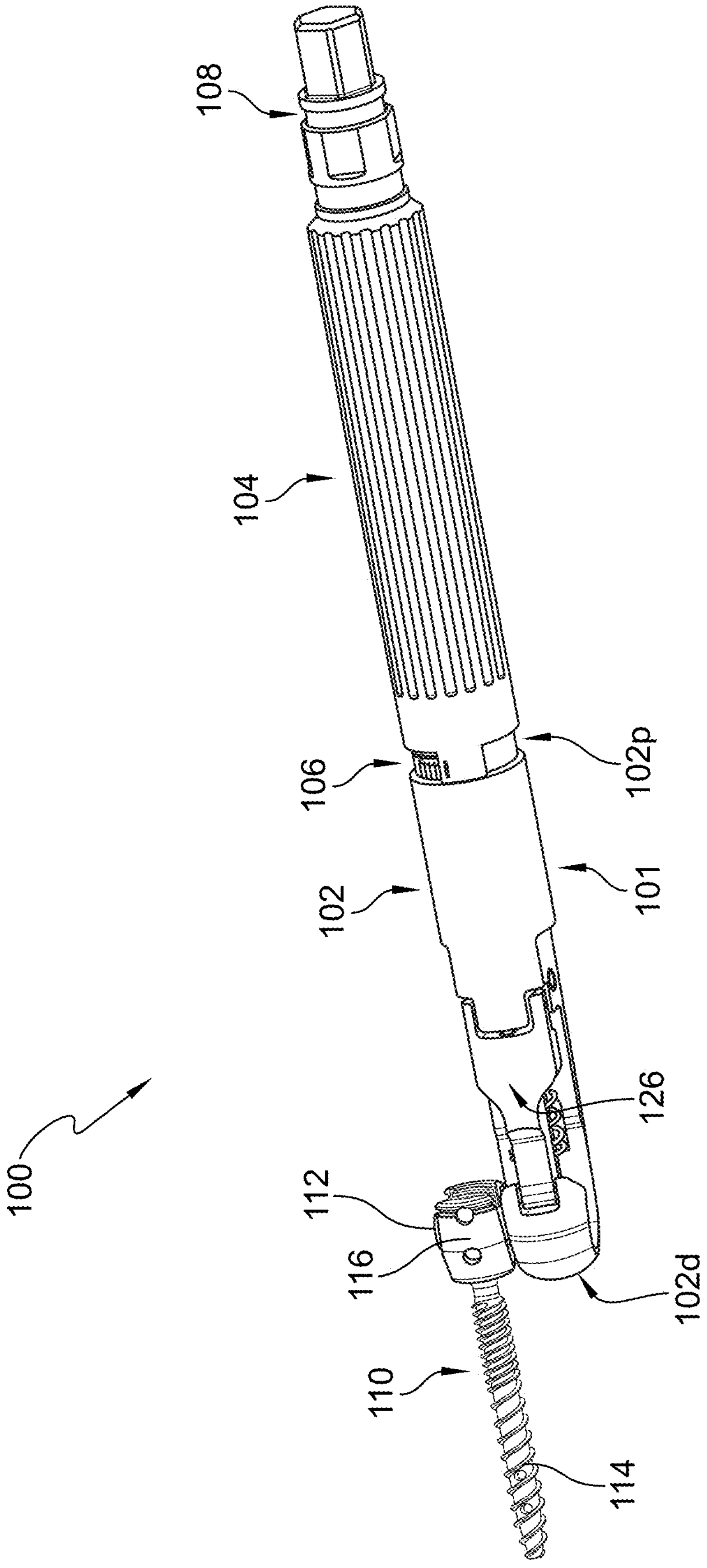
FIG. 1A is a perspective view of one embodiment of a cutting instrument and a bone anchor.
Figure 1B:
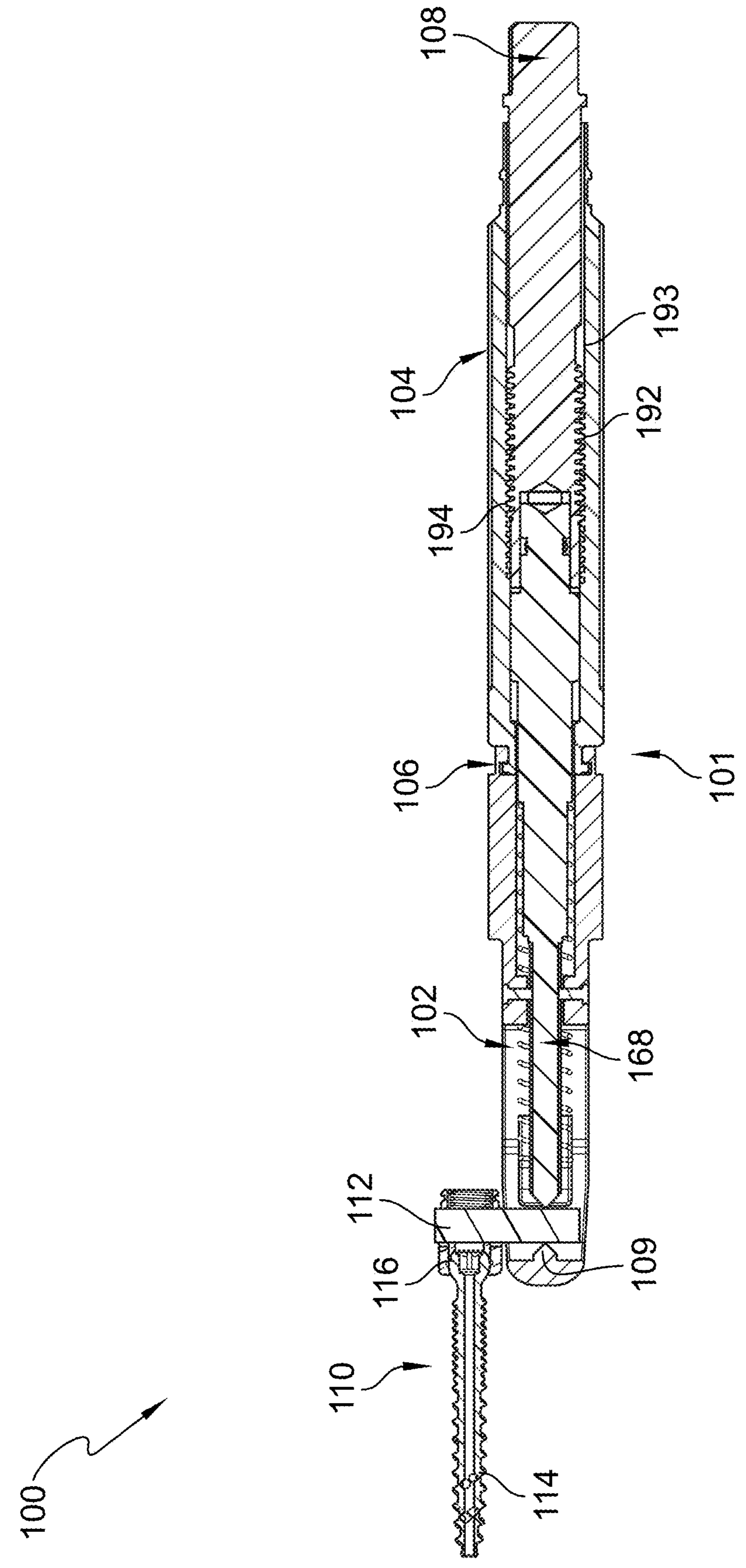
FIG. 1B is a side longitudinal cross-sectional view of the instrument and bone anchor of FIG. 1A.
Figure 1C:
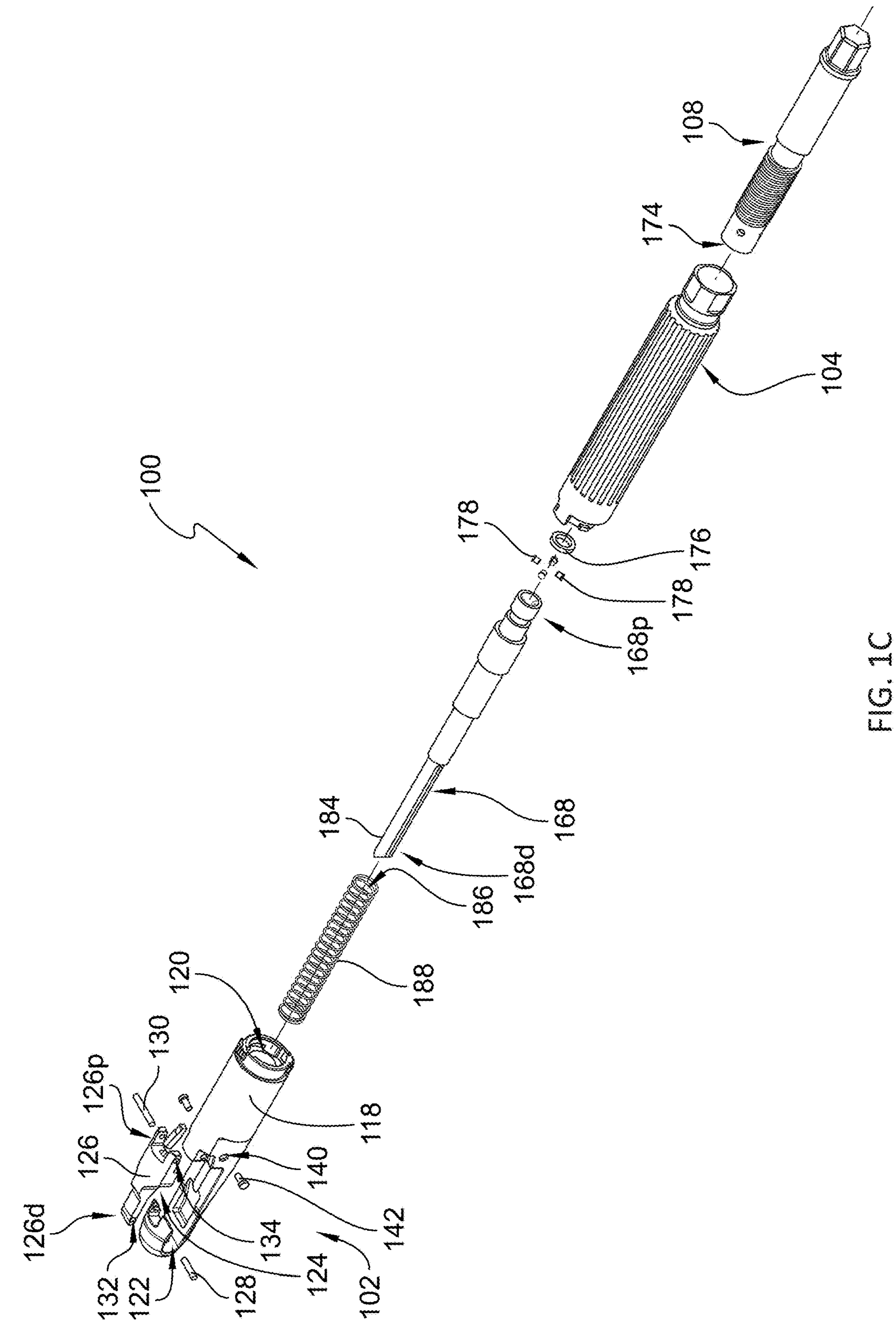
FIG. 1C is an exploded view of the instrument of FIG. 1A.

FIGS. 1A-1C illustrate perspective, longitudinal cross-sectional, and exploded views, respectively, of one embodiment of a cutting instrument 100. The cutting instrument 100 can include an outer sleeve 101 having a distal tip 102 and a proximal base tube 104 that can be modularly coupled and secured against separation by a lock 106. The cutting instrument 100 can also include an inner sleeve 108 that can be configured to rotate relative to the outer sleeve 101, e.g., via threaded engagement with the base tube 104, as well as an anvil 168 that is configured to translate relative to the outer sleeve 101. The distal tip 102 can be configured to receive an implant, e.g., a spinal rod or a bone plate, as discussed in greater detail below. The proximal base tube 104 can be modularly coupled to the distal tip 102 with the lock 106 securing the base tube 104 to the distal tip 102 during use. The inner sleeve 108 can move relative to the distal tip 102, base tube 104, and an implant engaged with the distal tip to facilitate cutting the implant.

While various implants and spinal fixation elements can be used, FIG. 1A illustrates an example embodiment of a bone anchor 110 that can be used with the devices disclosed herein. As shown, the bone anchor 110 can include a threaded shank 114 and a rod-receiving head 116. The threaded shank 114 can be configured to be threaded into bone and the rod-receiving head 116 can be configured to receive a spinal fixation element, such as the spinal rod 112. In the illustrated embodiment, the rod-receiving head 116 includes opposed arms that define a u-shaped receiving portion for seating the spinal rod 112. In some embodiments, the rod-receiving head 116 can also include mating features formed thereon to facilitate mating with one or more instruments. While various mating features can be used, in one embodiment the rod-receiving head 116 can include one or more recesses (e.g., blind bores, through-bores, grooves, notches, thread forms, etc.) formed in a proximal portion thereof for receiving one or more projections (e.g., pins, nubs, broken or continuous ridges, hooks, thread forms, etc.) that engage the bone anchor 110. In certain embodiments, any of a variety of complementary features can be utilized in any configuration (e.g., protrusions or other male features formed on the bone anchor and complementary recesses or female features formed on the instrument, etc.). Other implants can also be used, including, for example, hooks, plates, staples, etc.

Figure 2:
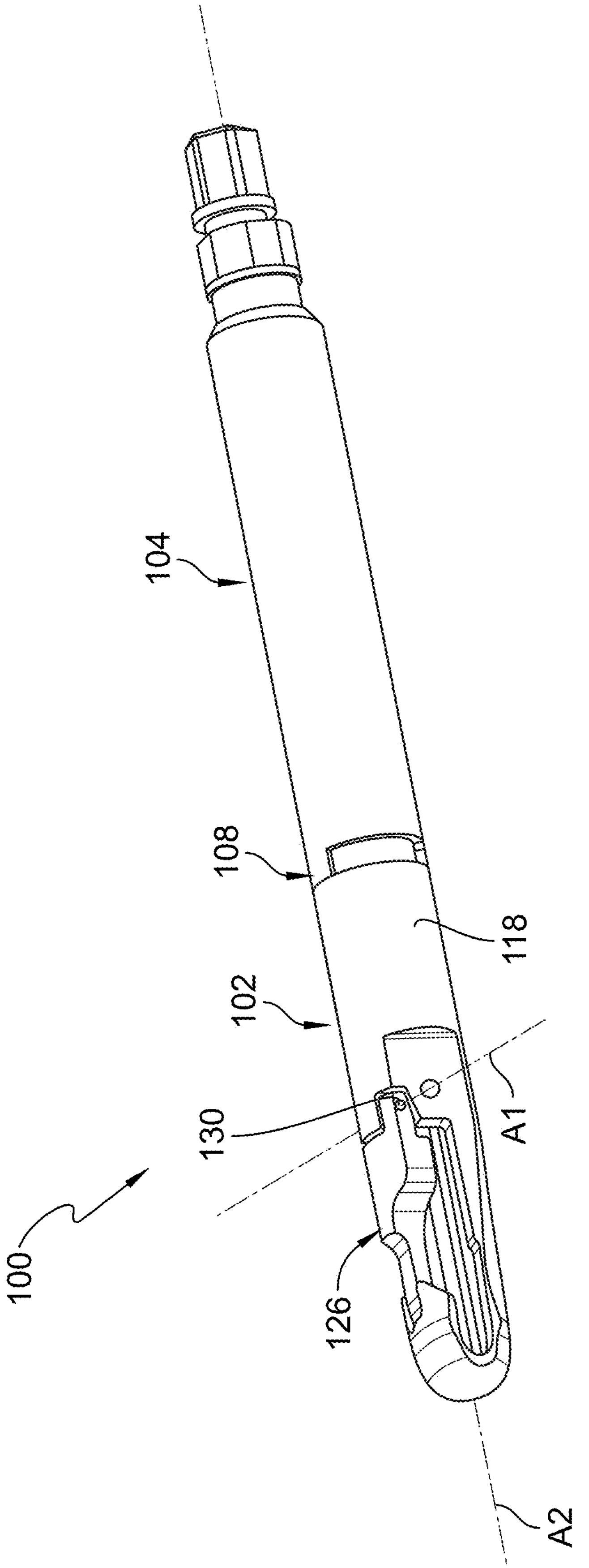
FIG. 2 is a perspective view of the cutting instrument of FIG. 1A.

FIG. 2 illustrates the assembled cutting instrument 100 in greater detail. As shown, the distal tip 102 can be coupled to the base tube 104 to form the outer sleeve 101. The coupling between the distal tip 102 and the base tube 104 can be modular such that the base tube 104 can be decoupled from the distal tip 102 and coupled to other cutting tips as needed. Modularity of the components can allow for efficient use of the instruments during operation, permit the interchangeable use of cutting tips configured for different surgical implants or components, and facilitate cleaning/sanitization of the instrument.

Figure 3A:
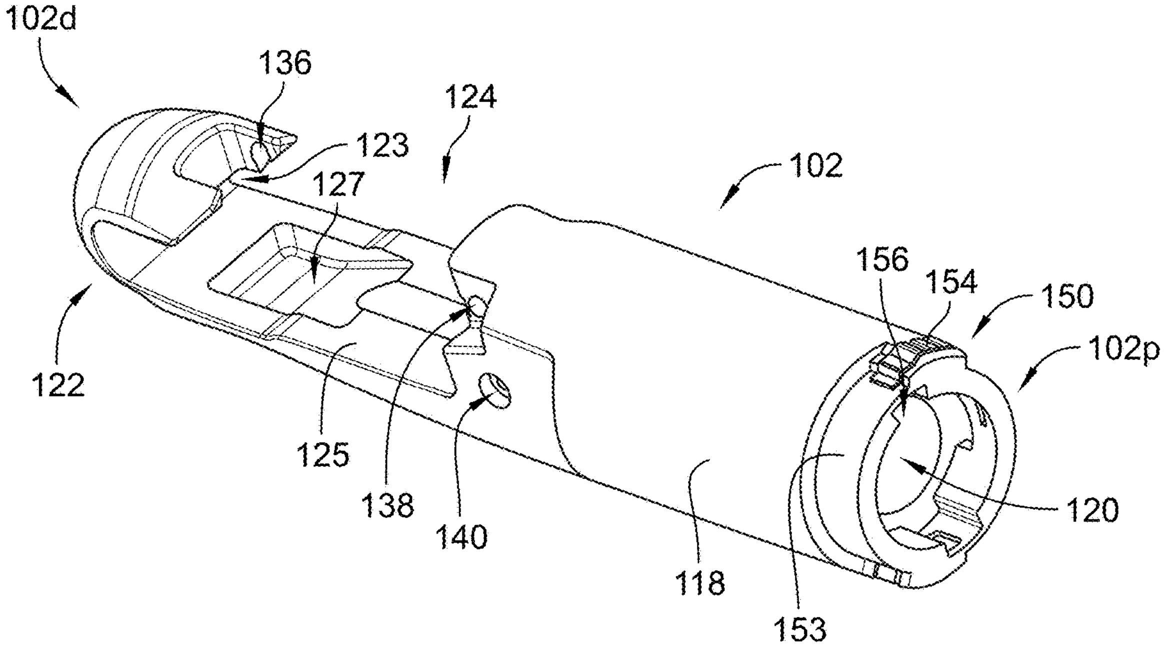
FIG. 3A is a perspective view of the distal tip of the cutting instrument of FIG. 1A.

The distal tip 102 can be configured to engage at least a portion of a spinal implant. For example, as shown in FIG. 3A, the distal tip 102 can include a cylindrical sidewall 118 that defines a lumen 120. The lumen 120 can extend substantially through a length of the distal tip 102 from a proximal end 102*p* to a distal end 102*d* thereof to receive the anvil 168, as described in greater detail below. The distal end 102*d* of the distal tip 102 can include a rod-receiving portion 122 having a slot 123 that is configured to receive the spinal rod 112 therein. The slot 123 of the distal tip 102 can resemble the U-shaped receiving portion of the rod-receiving head 116 of the bone anchor 110 such that the distal tip 102 can engage the spinal rod in a similar fashion. In contrast to the U-shaped receiving portion of the rod-receiving head 116, however, the rod-receiving portion 122 of the distal tip 102 can include a sharpened edge 109 (see FIG. 1B) positioned distal to the rod 112 and opposite the anvil 168 to aid the anvil in a cutting operation.

The sidewall 118 can include any number of openings extending along the distal tip 102. That is, in some embodiments, a cross-section of the sidewall 118 does not form a complete or continuous closed structure, such as an uninterrupted cylinder, along an entire length of the distal tip 102. For example, the distal tip 102 can include one or more cutouts, indentations, or slots formed in the sidewall 118 thereof. In the illustrated embodiment, the distal tip 102 has a hooked shape at its distal end 102*d*, with an opening 124 formed in a side of the tip proximal to the slot 123 of the rod-receiving portion 122.

In some embodiments, the opening 124 can allow a capture arm 126 (see FIGS. 1A, 1C, and 2) to be received therein. As shown in FIG. 2, the capture arm 126 in its resting position can be disposed in the opening 124 to extend substantially in line with the sidewall 118. The capture arm 126 can pivot relative to the distal tip 102 about a pin 130 that extends along an axis A1 that is transverse to a longitudinal axis A2 of the instrument 100. The capture arm 126 can therefore function similarly to a carabiner gate by pivoting radially inward to expose the opening 124 and allow a portion of a spinal implant to pass therethrough into the slot 123 of the rod-receiving portion 122. The capture arm 126 can also pivot radially outward to block the opening 124 such that no component can pass therethrough. That is, the capture arm 126 can be configured to move and/or pivot relative to the distal tip 102 to allow for implants to pass through the opening 124 into the slot 123 of the distal tip 102. For example, in some embodiments, the capture arm 126 can pivot radially inward to allow for side-loading of an implant, e.g., the spinal rod 112, into the slot 123. An inner surface 125 of the distal tip 102 opposite the opening 124 can include a recess or pocket 127 configured to receive a distal end 126*d* (see FIG. 1C) of the capture arm 126 therein. Once the spinal rod 112 or other implant is disposed within the slot 123, the capture arm 126 can pivot radially outward back to its resting position to block the opening 124. In addition, the distal end 126*d* of the capture arm 126 can include a pin 128 (see FIG. 1C) extending therethrough along an axis transverse to a longitudinal axis A2 of the instrument. Opposed ends of the pin 128 can extend beyond the sidewalls of the capture arm 126 such that they are received in recesses 136 (see FIG. 3A) formed in a portion of the distal tip 102 when the capture arm 126 is in its resting position. The pin 128 and its interaction with the recesses 136 can help increase the strength of the distal tip 102 to endure axial loads experienced during a cutting operation when the anvil 168 is distally advanced through an implant disposed in the slot 123 of the distal tip 102. More details about side-loading of implants using the capture arm are shown and discussed with respect to the figures below.

The distal tip 102 can include one or more surface features for engaging with other components of the cutting instrument 100. As noted above, for example, the capture arm 126 can be coupled to the distal tip 102 via a pin 130 that extends through a bore 138 (see FIG. 3A) in the distal tip 102 and a bore 134 (see FIG. 1C) in the capture arm 126. As noted above, the pin 128 can extend through a bore 132 in the capture arm 126 and can interface with the recesses 136 formed in the distal tip 102. As shown in FIG. 3A, the distal tip 102 can also include a bore 140 formed therein and configured to receive one or more pins 142 therethrough. The pins 142 can extend through opposed sides of the bore 140 and into the lumen 120 to engage the anvil 168 and prevent relative rotation between the anvil and the distal tip 102, as discussed in greater detail below.

Figure 3B:
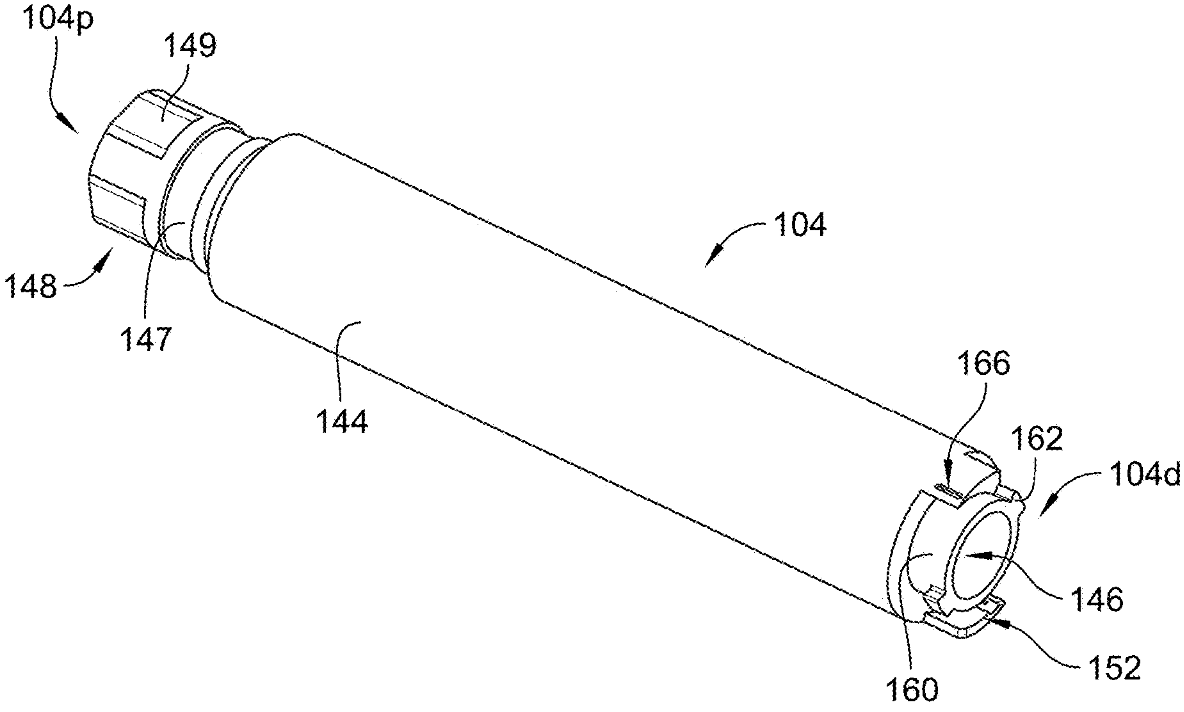
FIG. 3B is a perspective view of a base tube of the cutting instrument of FIG. 1A.

FIG. 3B illustrates the base tube 104 that is configured to be coupled to the distal tip 102 to form the outer sleeve 101 of the instrument 100. As shown, the base tube 104 can include a cylindrical sidewall 144 that defines a lumen 146 extending from a proximal end 104*p* to a distal end 104*d* thereof. The lumen 146 is configured to align with the lumen 120 of the distal tip 102 to receive the anvil 168 and inner sleeve 108 therethrough. The proximal end 104*p* of the tube 104 can include a counter-torque feature 148 that can allow for modular coupling of a handle or other counter-torque application implement thereto. The counter-torque feature 148 can have a variety of forms and sizes. In some embodiments, the counter-torque feature 148 can include one or more flats 149 to facilitate the application of torque to the outer sleeve 101. In the illustrated embodiment, the counter-torque feature 148 includes four flat portions 149 disposed around a circumference of a proximal portion of the tube 104.

The distal tip 102 and base tube 104 can include complementary features formed thereon that form a lock 106 that can selectively secure the two components against separation from one another. The lock 106 can be formed between the distal end 104*d* of the base tube 104 and the proximal end 102*p* of the distal tip 102 to facilitate modular coupling therebetween. The proximal end 102*p* of the distal tip 102 can include one or more mating features 150 that can interface with corresponding mating feature 152 on the distal end 104*d* of the base tube 104, as shown in FIGS. 3A-3B. The mating features 150, 152 can snap into engagement with one another to secure the distal tip 102 against separation from the base tube 104. After use, the distal tip 102 can be decoupled from the base tube 104 and modularly coupled to another tip, or vice versa, to facilitate efficiency, ease of cleaning of the components after use, etc.

Figure 4B:
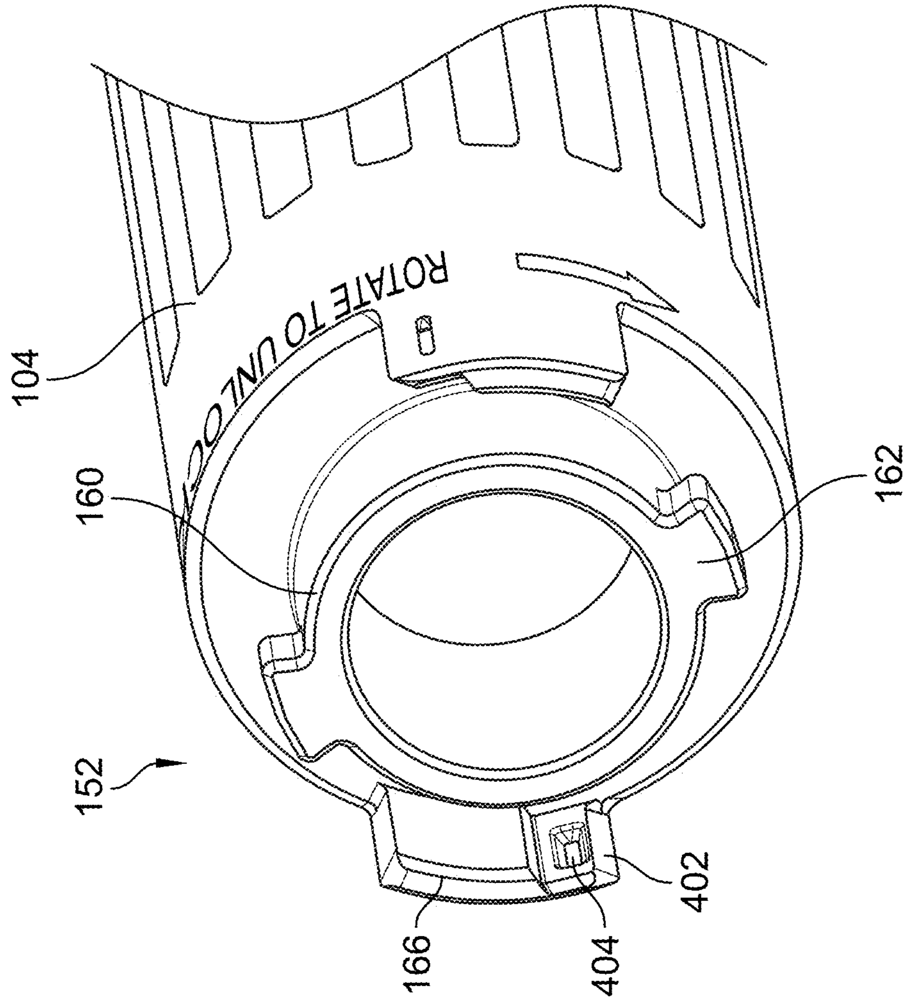
FIG. 4B is a perspective view of a corresponding mating feature on the base tube of FIG. 3B.
Figure 4A:
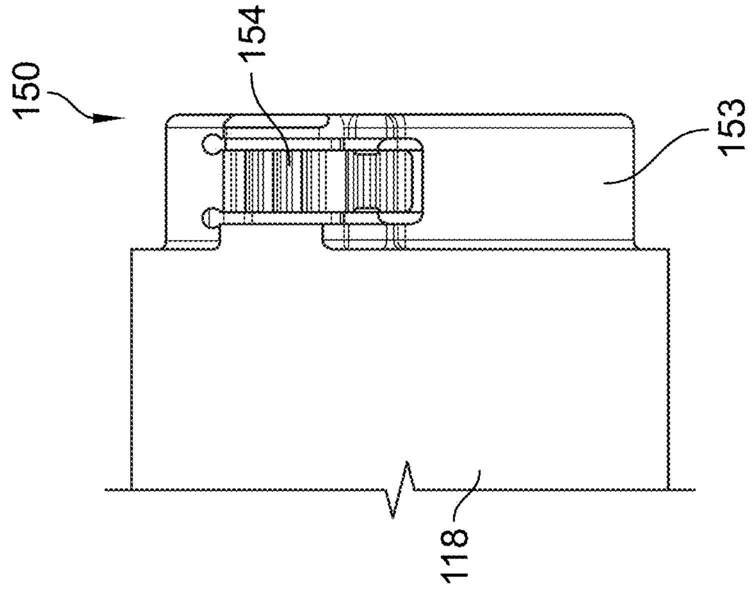
FIG. 4A is a side view of a mating feature on the distal tip of FIG. 3A.
Figure 5A:
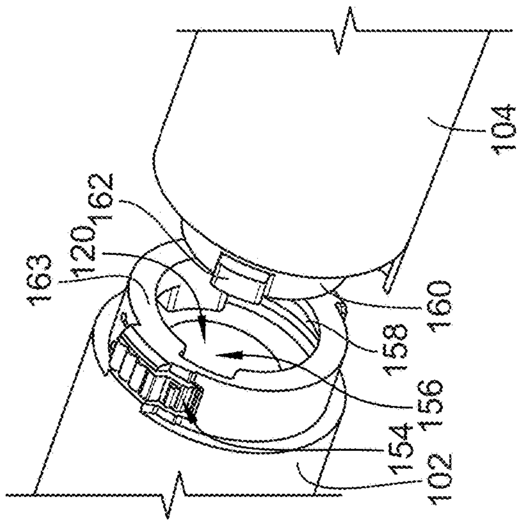
FIG. 5A is a perspective view of the coupling between the distal tip of FIG. 3A and the base tube of FIG. 3B.
Figure 5B:
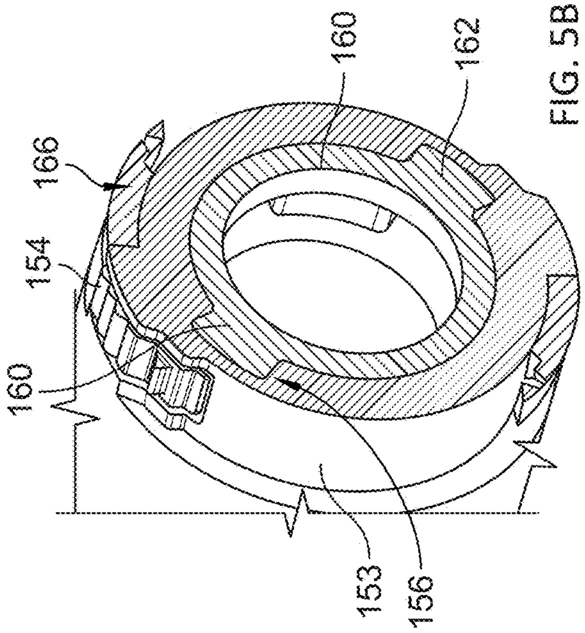
FIG. 5B is a perspective cross-sectional view of the coupling between the base tube and the distal tip of FIG. 5A.
Figure 5C:
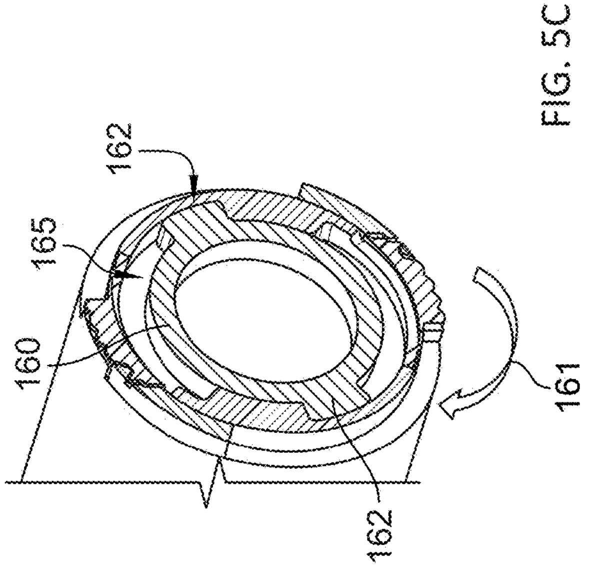
FIG. 5C is a perspective cross-sectional view of the coupling between the base tube and the distal tip of FIG. 5A after locking against separation.
Figure 5D:
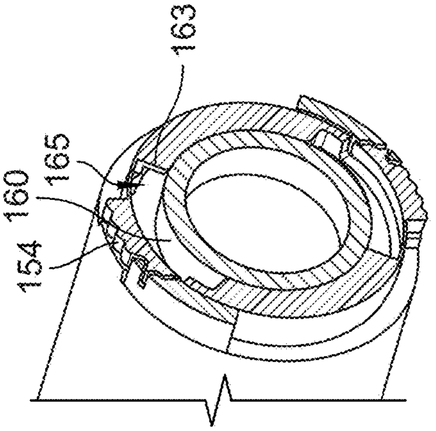
FIG. 5D is an alternative perspective cross-sectional view of the coupling between the base tube and the distal tip of FIG. 5A after locking against separation.
Figure 6:
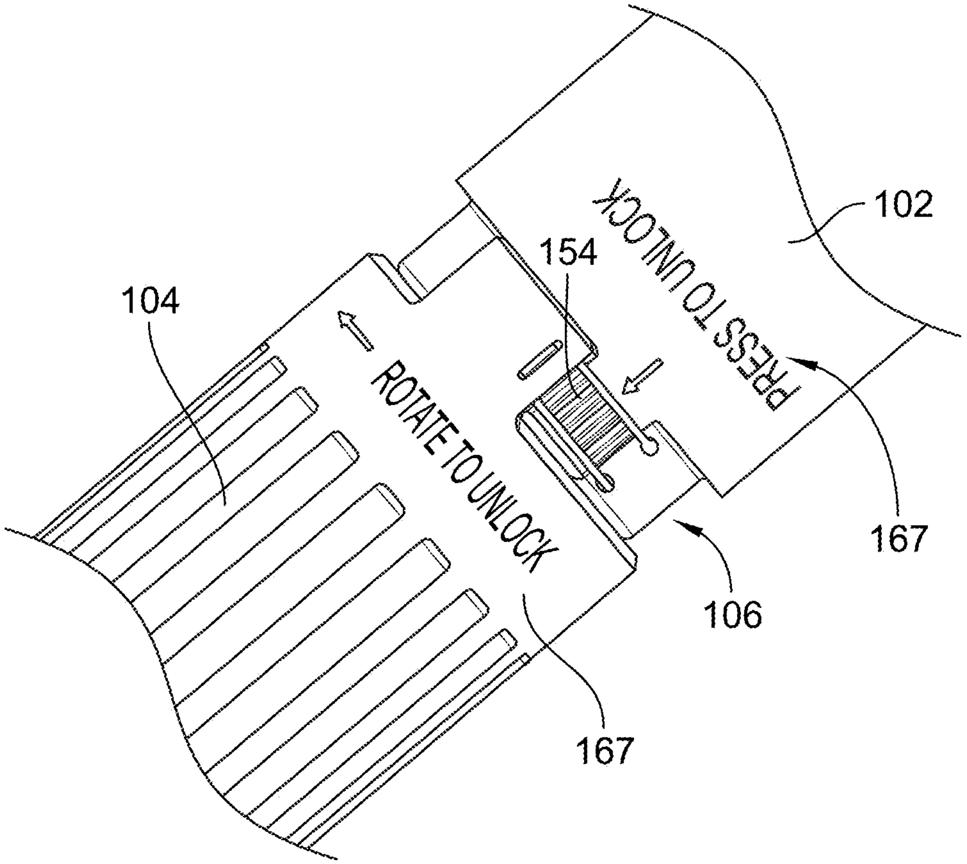
FIG. 6 is a perspective view of an indicator on the coupling between the base tube and the distal tip of FIG. 5A.

FIGS. 4-6 illustrate the lock 106 in greater detail. As shown in FIG. 4A, the mating feature 150 positioned at the proximal end 102*p* of the distal tip 102 can include a reduced-diameter portion 153. The mating feature 150 can include a snap lock 154 configured to engage a corresponding portion of the mating feature 152 of the base tube 104 to couple the tip 102 and tube 104 and form the outer sleeve 101 of the cutting instrument 100. The snap lock 154 can be fashioned as a portion of the reduced-diameter portion 153 extending as a living hinge such that it is deflectable radially inward and outward. The snap lock 154 can also include one or more protrusions or other surface features formed thereon to engage with a corresponding recess or other surface feature formed on the base tube 104. As shown in FIG. 5A, the mating feature 150 can further include one or more recesses or cavities 156 formed on an inner surface 158 of the reduced-diameter portion 153. The recesses or cavities 156 can extend at least partially around an inner circumference of the reduced-diameter portion 153 and include one or more openings 165 facing proximally that can allow protrusions 162 formed on the base tube 104 to advance distally into the recesses or cavities 156 of the distal tip 102.

The corresponding mating feature 152 of the base tube 104, as shown in FIG. 4B, can include a reduced-diameter portion 160 having one or more radial protrusions 162 extending therefrom. The radial protrusions 162 can be configured to extend into the recesses or cavities 156 of the distal tip 102 to couple the distal tip to the base tube 104. The mating feature 152 can further include one or more extensions 166 spaced apart from the reduced-diameter portion 160 and extending distally such that, when the distal tip 102 and base tube 104 are coupled, the reduced-diameter portion 153 of the distal tip is received between the reduced-diameter portion 160 and the one or more extensions 166 of the base tube. The one or more extensions 166 can be configured to interface with the snap lock 154 of the distal tip 102 to selectively lock the distal tip against rotation relative to the base tube 104. For example, the one or more extensions 166 can include a ramped end 402 to facilitate receiving the snap lock 154 as the distal tip 102 and base tube 104 are rotated relative to one another to complete a locking operation. Further, the one or more extensions 166 can include a slot or other bore 404 formed therein that can receive a protrusion or other surface feature formed on the snap lock 154 when in a locked configuration.

FIGS. 5A-5D illustrate the coupling of the distal tip 102 to the base tube 104 and actuation of the lock 106 in greater detail. While a snap lock coupling is shown in the illustrated embodiment, the distal tip 102 can be coupled to the base tube 104 in other manners in some embodiments, including by press-fit, using a mechanical fastener like a pin, screw, bolt, etc., or more permanently using adhesives, welding, etc. In some embodiments, a modular or selectively actuated coupling mechanism can be employed to provide modularity and allow various distal tip configurations to be quickly swapped out for use during a procedure.

As shown in FIG. 5A, coupling the distal tip 102 to the base tube 104 can begin by moving the two components toward one another in axial alignment to bring the proximal end of the distal tip and its reduced-diameter portion 153 near to the distal end of the base tube and its reduced-diameter portion 160. The distal tip 102 and base tube 104 can be rotationally aligned such that the protrusions 162 formed on the base tube can be inserted into the recesses 156 as the distal tip and base tube are moved toward one another axially. In addition, the one or more snap lock 154 and recess 156 on the distal tip 102, as well as the one or more protrusion 162 and extension 166 on the base tube 104, can be positioned around a circumference of the distal tip and proximal base tube such that the snap lock 154 and extension 166 are offset from one another when the recess 156 and protrusion 162 are aligned to allow for axial movement of the distal tip and proximal base tube toward one another. Such movement can result in the insertion of the reduced diameter portion 160 of the base tube 104 into the lumen of the reduced diameter portion 153 of the distal tip 102. The cross-sectional view of FIG. 5B shows this positioning where the reduced-diameter portion 160 of the base tube 104 is inserted into the lumen of the reduced-diameter portion 153 of the distal tip 102, along with the rotational alignment of the protrusions 162 and recesses 156 to allow the axial movement of the distal tip and proximal base tube toward one another. Moreover, the rotational offset of the snap lock 154 and extensions 166 can be seen as well.

As shown by the transition between FIGS. 5B and 5C, once the distal tip 102 and base tube 104 are axially positioned relative to one another, they can be locked against separation by rotating relative to one another about a longitudinal axis thereof. Rotating the two components relative to one another, as shown by arrow 161 in FIG. 5C, can cause each protrusion 162 to move from the proximally-extending recess 156 into an internal locking recess or cavity 165 that can extend along the inner surface 158 of the reduced-diameter portion 153 of the distal tip 102. The locking recess 165 can be formed as a groove in the inner surface 158 and can include a proximal lip or shoulder 163 such that it does not extend to a proximal end of the distal tip like the recess 156. Accordingly, when the protrusion 162 is positioned in the recess 165, it will not be possible to axially separate the distal tip 102 from the base tube 104.

Rotating the distal tip 102 and base tube 104 relative to one another can also move each extension 166 into engagement with each snap lock 154, as shown in the transition between FIGS. 5B and 5C/5D (FIGS. 5C and 5D are cross-sectional views with a cutting plane positioned at different axial positions to show the recess 165 in FIG. 5C and the proximal lip 163 in FIG. 5D). More particularly, relative rotation of the distal tip 102 and base tube 104 can cause each extension 166 to rotate over each snap lock 154. The ramped end 402 of each extension 166 can deflect each snap 154 lock radially inward as it passes over and the snap lock 154 can then deflect radially outward into the slot or bore 404 when aligned. This can selectively lock the distal tip 102 and base tube 104 against relative rotation and therefore separation until a user takes action, such as pushing each snap lock 154 radially inward to release the lock against relative rotation. Once the rotation lock is released, the distal tip 102 and base tube 104 can be rotated in a direction opposite the arrow 161 until the protrusions 162 again align with the proximally-extending recesses 156, at which point the distal tip and base tube 104 can be axially separated from one another.

The cutting instrument 100 can include one or more indicators that instruct how to couple and/or decouple the distal tip 102 and the base tube 104 and/or show whether the instrument 100 is in an unlocked configuration or in a locked configuration. For example, as shown in FIG. 6, the instrument 100 can include indicators 167 in the form of labels or images to indicate the status of the lock 106. The instrument 100 can include a first text indicator of "Press to Unlock" and/or "Rotate to Unlock" on one or both of the distal tip 102 and the base tube 104. The text indicators are one example and other text, image, or other labels or indicators can be utilized.

Figure 7:
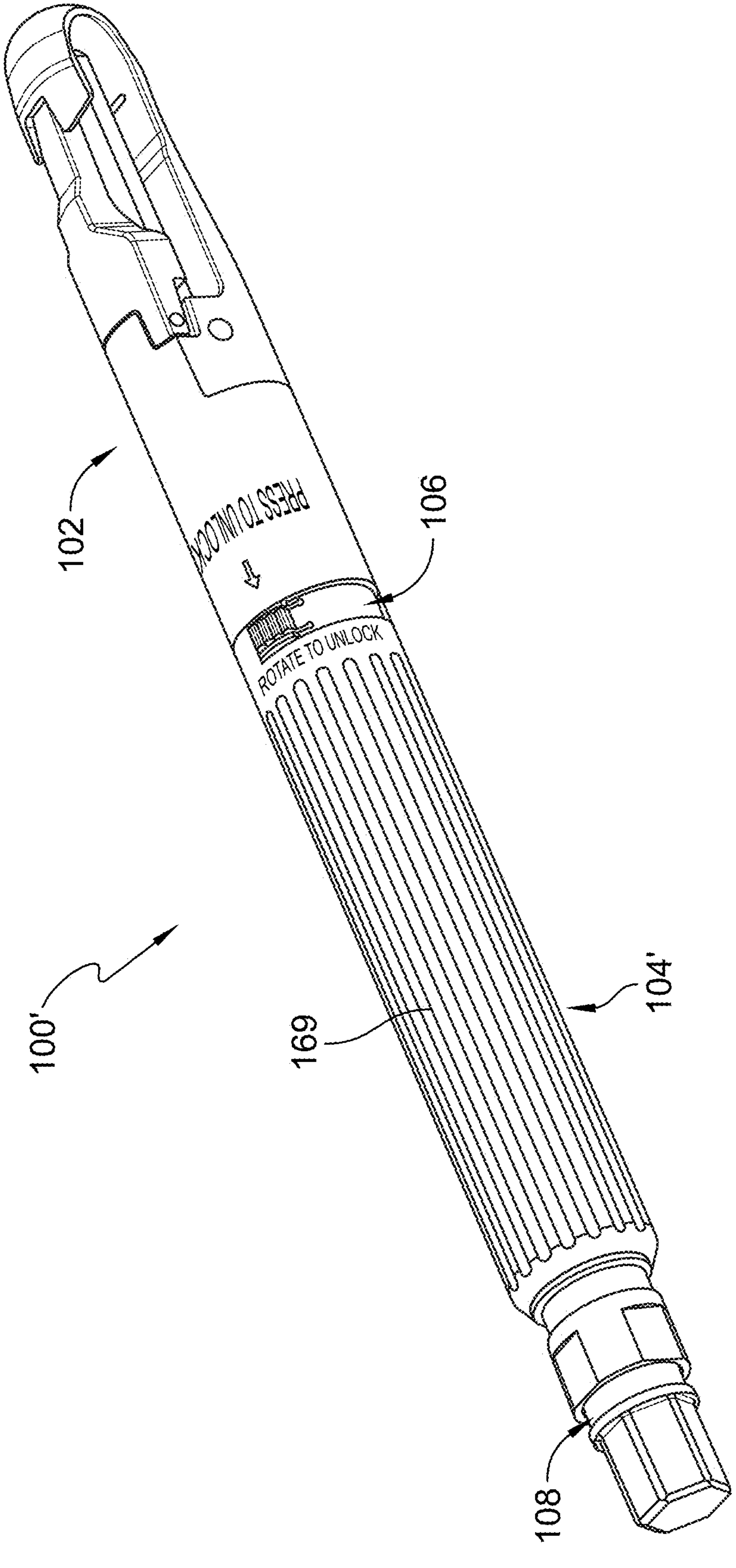
FIG. 7 is a perspective view of another embodiment of a cutting instrument.
Figure 8A:
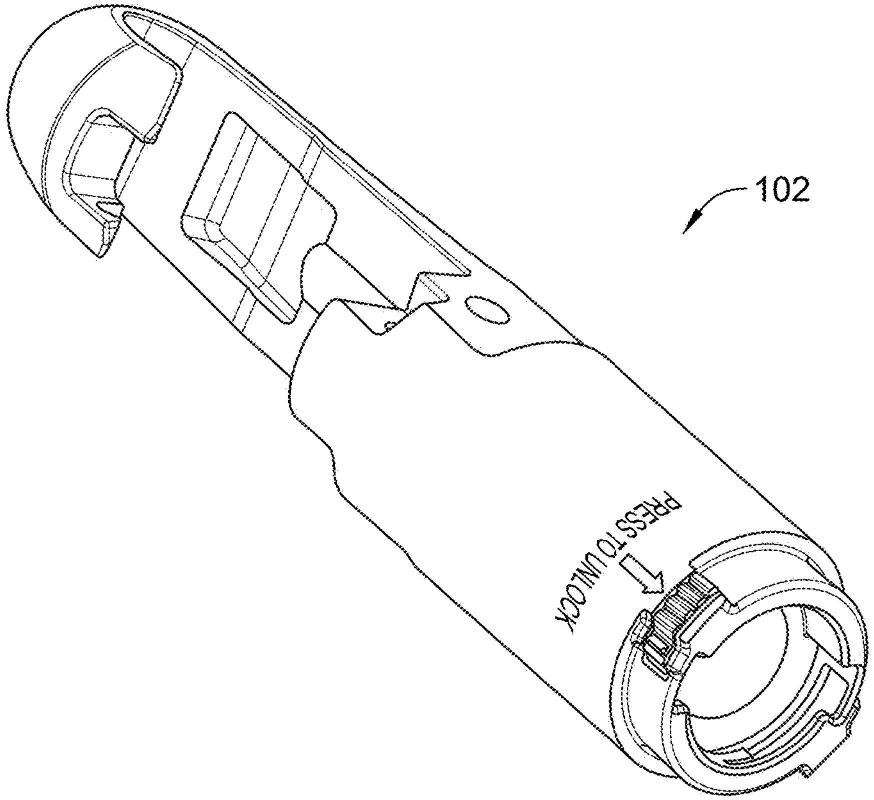
FIG. 8A is a perspective view of a distal tip of the cutting instrument of FIG. 7.
Figure 8B:
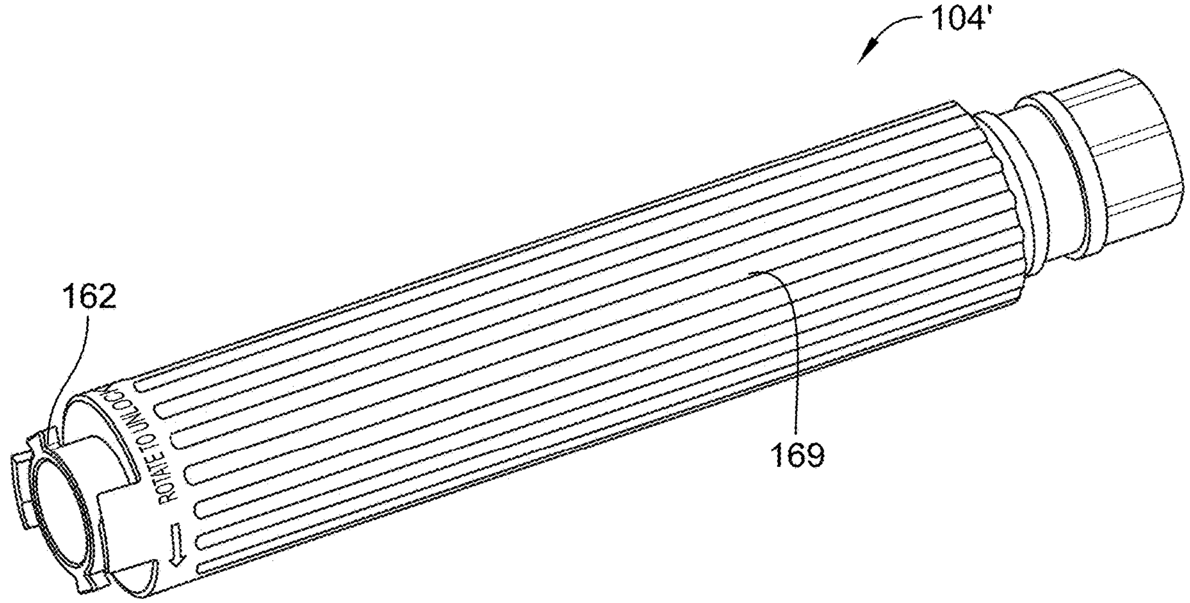
FIG. 8B is a perspective view of a base tube of the cutting instrument of FIG. 7.

FIGS. 7-8B illustrate an alternate embodiment of a cutting instrument 100' having surface features formed on the base tube 104'. As shown, one or more grip grooves 169 can be formed along a length of the base tube 104'. For example, the grip grooves 169 can be positioned to facilitate a user's grip of the instrument 100' during use. The grip grooves 169 can include features that increase user comfort and ease of use of the instrument 100'. Any number of features can be included to increase comfort and ease of use. For example, the grip grooves 169 can include surface features to facilitate engagement, such as recesses or dimples to engage with a user's fingers, finger loops, etc. In some embodiments, different materials can be utilized to form the grip grooves 169 or some portion thereof. For example, in some embodiments a silicone overmold or grip of a different material can be coupled to the base tube 104'.

Figure 9A:
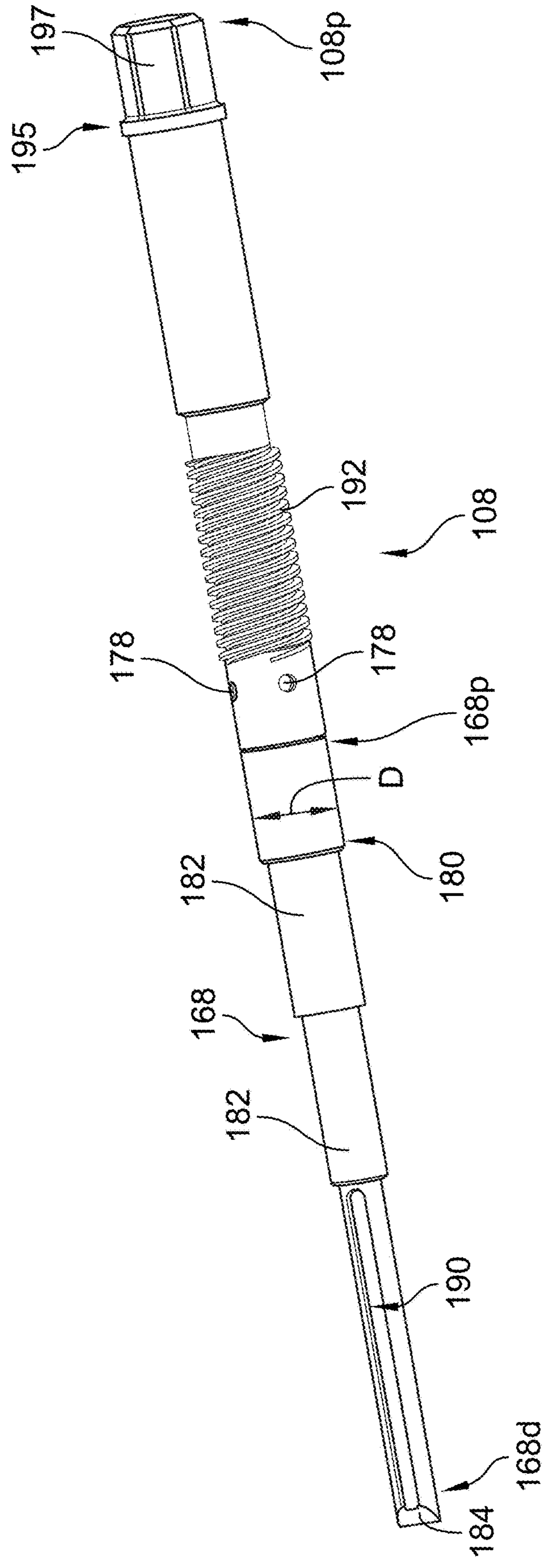
FIG. 9A is a perspective view of an inner sleeve of the cutting instrument of FIG. 1A having an anvil on a distal end thereof.

FIG. 9A illustrates the inner sleeve 108 and anvil 168 configured to be received through the lumens 120, 146 of the cutting instrument 100. The inner sleeve 108 can be used to provide axial thrust and translate the anvil 168 to cut an implant or other component disposed in the distal tip 102. The anvil 168 and the inner sleeve 108 can be coupled to one another in a manner that allows relative rotation between the components. For example, as shown in FIG. 1C, a proximal end 168*p* of the anvil can be configured to be received in a channel 174 formed in the sleeve 108. A washer 176 and a plurality of pins 178 can be used at the interface of the anvil 168 and the sleeve 108 to couple the components in a manner that prevents relative axial translation therebetween while allowing relative rotation therebetween.

Figure 9B:
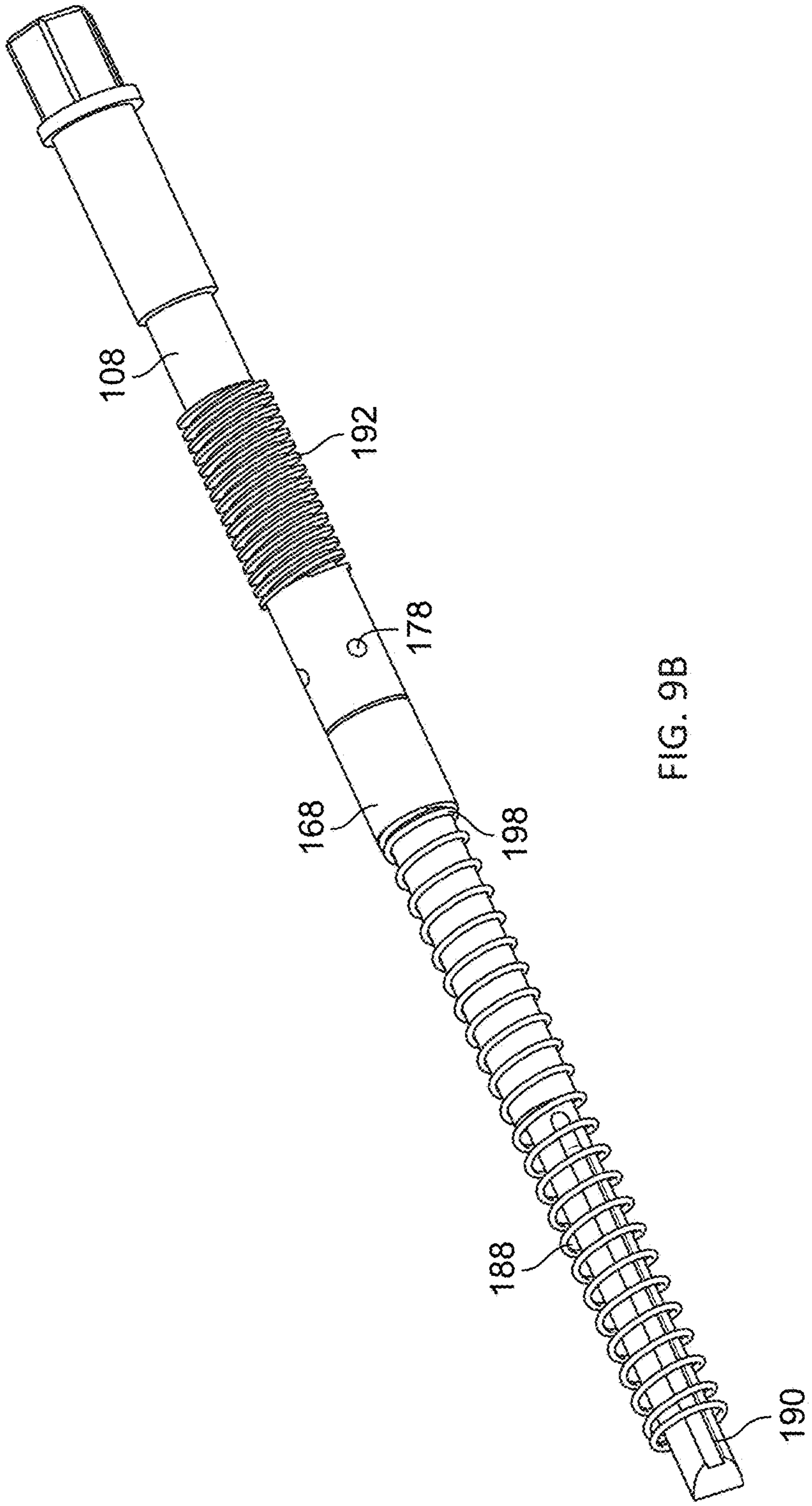
FIG. 9B is a perspective view of the inner sleeve of FIG. 9A having a spring disposed on a distal end thereof.
Figure 9C:
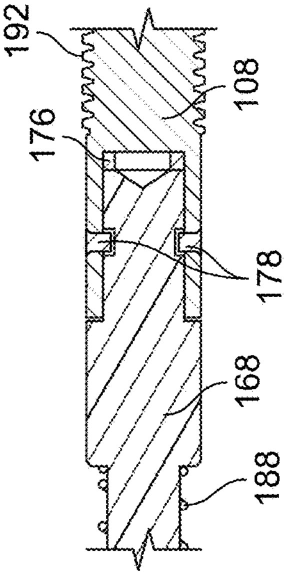
FIG. 9C is a longitudinal cross-sectional view of an assembled configuration of the inner sleeve and the anvil of FIG. 9A.

FIGS. 9B and 9C show additional views of the inner sleeve 108 and anvil 168, as well as the spring 188 discussed in more detail below. In particular, the cross-sectional view of FIG. 9C illustrates the assembled configuration of the inner sleeve 108 and anvil 168 via the pins 178 disposed in through-bores formed in a distal portion of the inner sleeve 108 and extending into a groove formed in a proximal portion of the anvil 168. This configuration prevents relative translation of the inner sleeve 108 and anvil 168 along a longitudinal axis thereof, i.e., axial separation of the components, while allowing relative rotation therebetween about a longitudinal axis thereof. With this configuration, the inner sleeve 108 can be threadably coupled to the outer sleeve 101 and rotated relative thereto to axially translate the anvil 168, and the anvil 168 can be prevented from rotating relative to the outer sleeve 101 using rotation control alignment grooves 190 formed along a length thereof. This operation is described in more detail below.

The translating anvil 168 can include a body 180 having a series of cylindrical portions 182 with smaller diameters D terminating in a cutting tip 184 at a distal end 168*d* of the anvil 168. As shown, the cutting tip 184 can terminate in a substantially V-shaped point that is configured to cut through the implant. While a V-shaped cutting tip is shown, the shape and/or angles of the cutting tip 184 can be altered based on a material of the implant being cut, a shape of the distal outer sleeve 102, and so forth. Due to the hardness of the implants being cut, in some embodiments, the cutting tip 184 can be a replaceable component such that it can be replaced after cutting one or more spinal rods 112 and/or plates 300 to maintain cutting performance and prevent damage, such as breaking and chipping of the cutting tip 184 after use. In some embodiments, the cutting tip 184 and/or the anvil 168 can be reusable and can include additional features to extend its usable lifespan. For example, the cutting tip 184 and/or the anvil 168 can be treated to increase its hardness, e.g., using a titanium nitride physical vapor deposition (PVD) coating, etc., that can preserve sharpness of the cutting tip 184 to allow for extended use. In some embodiments, the various embodiments for the anvil 168 and/or the cutting tip 184 can be included in a kit that can allow users to interchange the type of cutting tip used with the cutting instrument 100.

The anvil 168 can be configured to be received through an interior channel of a spring 188 that can bias the anvil 168 and inner sleeve 108 proximally by extending between a first, proximally-facing shoulder 1102 (see FIG. 11A) formed in the inner lumen 120 of the distal tip 102 and a second, distally-facing shoulder 198 (see FIG. 9B) formed on the anvil 168. The anvil 168 can include one or more rotation control alignment grooves 190 formed along a distal portion thereof to prevent rotation of the anvil 168 relative to the distal tip 102 while allowing axial translation relative thereto, as discussed further below.

The inner sleeve 108 can include a threaded surface 192 on at least a portion thereof. The threaded surface 192 can be received in the lumen 146 of the base tube 104 to engage with threads 194 formed on an interior proximal surface 193 of the tube 104. Any of a variety of thread forms can be utilized and, in some embodiments, a triple lead Acme centralizing thread can be utilized. Distal advancement of the inner sleeve 108 relative to the base tube 104 can occur by threaded engagement between the inner sleeve 108 and the base tube 104. Relative rotation of these components can cause accompanying axial translation, which can impart force onto the anvil 168 and cause it to translate without rotation, as discussed in greater detail below.

A proximal end 108*p* of the inner sleeve 108 can include a drive feature 195 that can allow for modular coupling of a driver handle, powered driver, or other torque application implement to the inner shaft 108. The drive feature 195 can have a variety of forms and sizes. In some embodiments, the drive feature 195 can include one or more flats 197 to facilitate the application of torque thereto. In the illustrated embodiment, the drive feature 195 is a hex feature having six flat portions 197 disposed around a circumference thereof.

Figure 10:
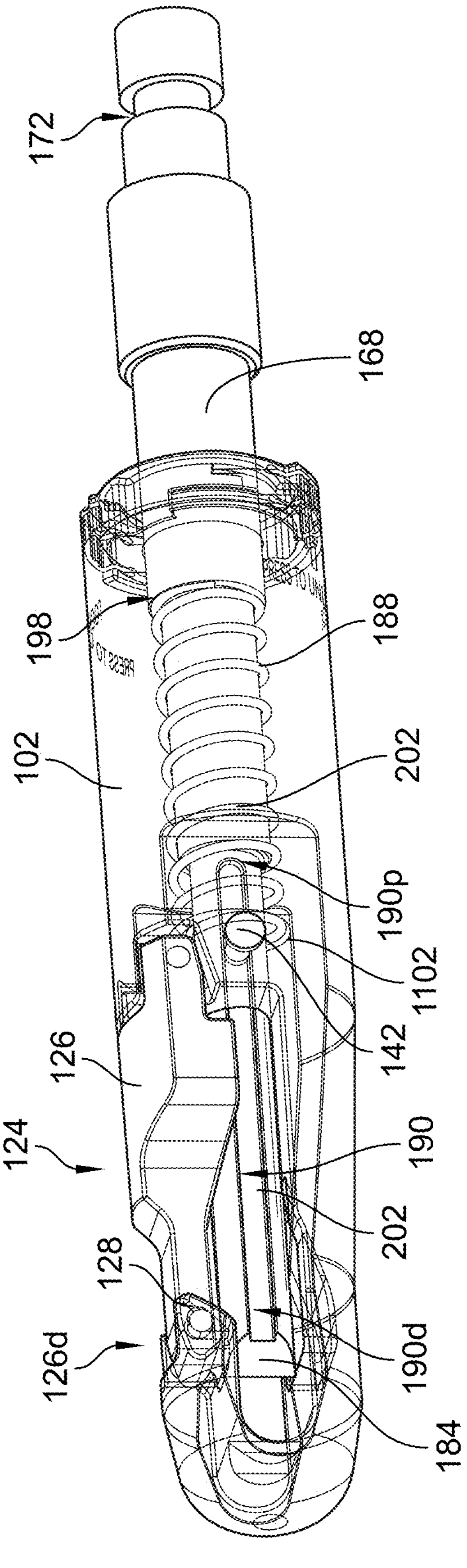
FIG. 10 is a partially transparent perspective view of the anvil of FIG. 9A disposed within the distal tip of the cutting instrument of FIG. 1A.

FIG. 10 illustrates the translating anvil 168 disposed within the distal tip 102 of the cutting instrument 100. As shown, the anvil 168 is disposed through the spring 188 and, given the distally advanced position of the anvil, the spring 188 is under compression between the distally-facing shoulder 198 of the anvil and the proximally-facing shoulder 1102 of the distal tip. As noted above, one or more traveling pins 142 can be positioned through bores formed in the distal tip 102 (e.g., bore 140 shown in FIG. 1C) such that they extend into the inner lumen of the distal tip and ride along the one or more rotation control alignment grooves 190 such that rotation of the anvil 168 relative to the distal tip 102 is prevented while axial translation between the two components is allowed. Further, the one or more rotation control alignment grooves 190 can prevent undesirable off-axis movement of the anvil 168 relative to the distal tip 102, such as lateral deflection that might result during a cutting operation when a large amount of distally-directed force is imparted onto the anvil 168 to press it through an implant disposed in the distal end of the distal tip 102.

As mentioned above, the capture arm 126 can be positioned in the opening 124 to allow for side loading of the implant, e.g., a spinal rod 112, into the rod-receiving portion 122 of the distal tip 102. The capture arm 126 can pivot radially inward to expose a portion of the opening 124 to allow the spinal rod 112 to pass therethrough. The capture arm 126 can taper distally, as shown in FIG. 10, to a reduced thickness at its distal end 126*d* in order to maximize the size of implant that can be passed through the opening 124 when the capture arm is pivoted radially inward (e.g., as shown in FIGS. 17D and 17E). As noted above, the pivoting capture arm 126 can function similarly to a carabiner gate and can be biased toward a closed configuration in which the opening 124 is blocked and the capture arm 126 can help endure forces experienced during a cutting operation by providing a force transmission path across the opening 124. Biasing of the capture arm 126 toward a closed position can be achieved with a leaf spring 204 or other lateral deflection biasing element, as shown in the cross-sectional views of FIGS. 11A and 12A. The spring 204 can be anchored to a portion of the distal tip 102 and extend into a recess 206 formed within the proximal end 126*p* of the capture arm 126.

Transition of the cutting instrument 100 between an initial configuration and a cutting configuration is shown in FIGS. 11A-12B. In its initial configuration, the inner sleeve 108 and anvil 168 can be retracted proximally relative to the tip 102 and tube 104. In certain embodiments, the threaded surface 192 of the inner sleeve 108 can be disengaged from the threads 194 of the tube 104, while in other embodiments the threads can remain engaged over a portion thereof (e.g., a proximal portion of the threads 194 and a distal portion of the threads 192). Moreover, in its initial configuration, the spring 188 can be positioned in an uncompressed, resting state or an initial, low-compression state while the anvil 168 is retracted relative to the capture arm 126. Retraction of the anvil 168 relative to the capture arm 126 can allow for actuation of the capture arm 126 for side-loading and unloading of an implant from the cutting instrument 100. For example, in the initial configuration, the cutting tip 184 of the anvil 168 can be retracted to a position proximal to the proximal end 126*p* of the capture arm 126. Moreover, a distance D1 can separate the drive feature 195 of the inner sleeve 108 and a proximal end of the tube 104. This distance can represent the distance that the anvil 168 can be advanced distally during a cutting operation.

Figure 11A:
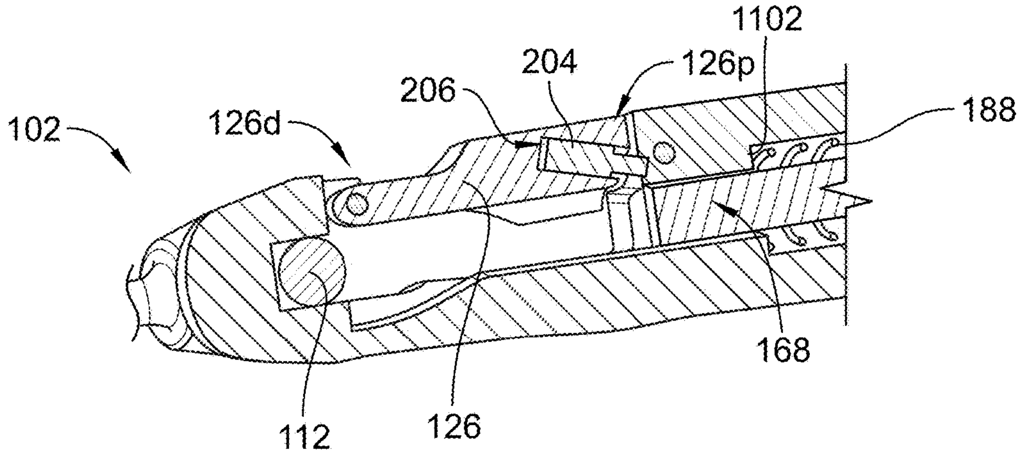
FIG. 11A is a longitudinal cross-sectional view of a capture arm biased towards a closed position at the distal tip of the cutting instrument in an initial configuration of FIG. 1A.
Figure 11B:
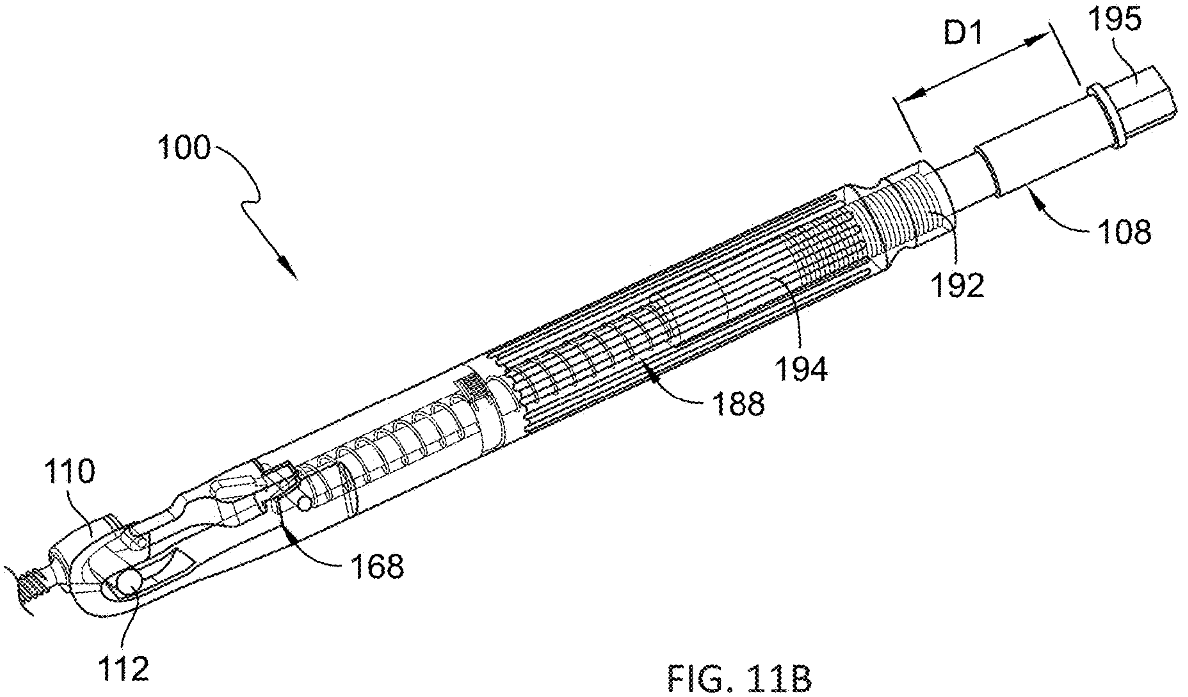
FIG. 11B is a partially transparent perspective view of the cutting instrument of FIG. 1A in the initial configuration of FIG. 11A.
Figure 12A:
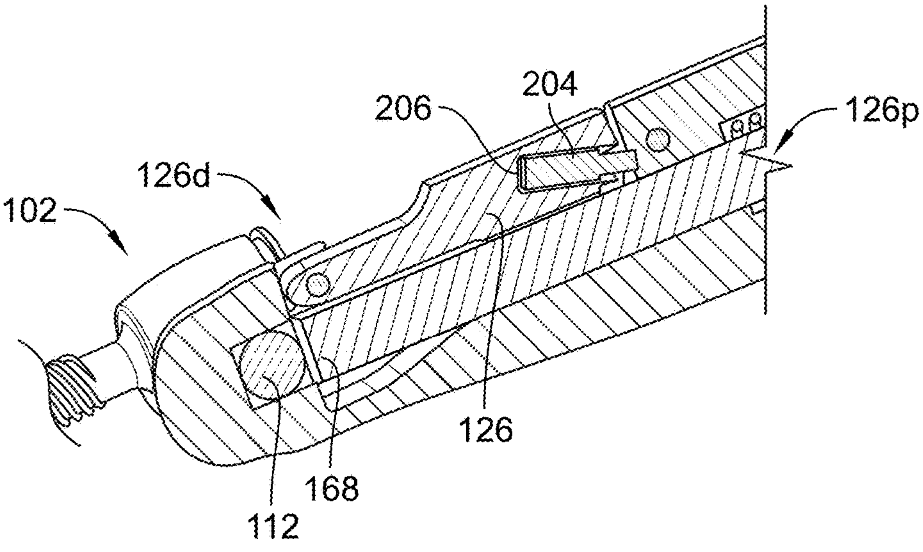
FIG. 12A is a longitudinal cross-sectional view of a capture arm biased towards a closed position at the distal tip of the cutting instrument in the cutting configuration of FIG. 1A.
Figure 12B:
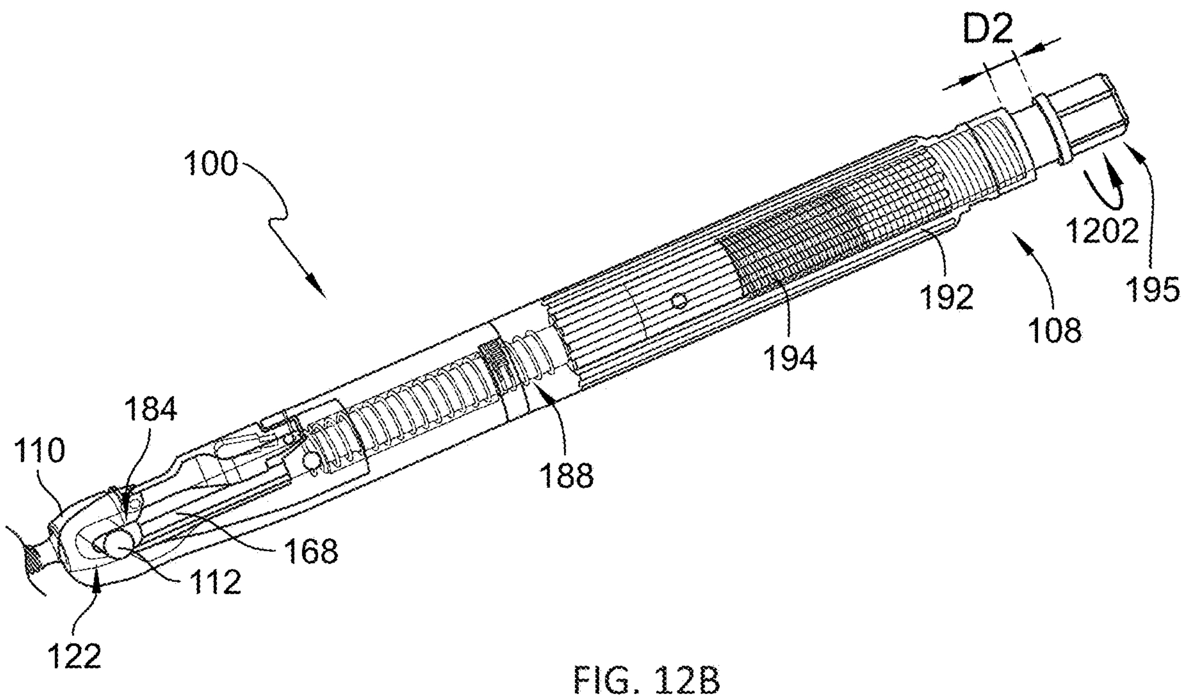
FIG. 12B is a partially transparent perspective view of the cutting instrument of FIG. 1A in the cutting configuration of FIG. 12A.

Distal advancement of the inner sleeve 108 and anvil 168 from the position shown in FIGS. 11A and 11B to the positions shown in FIGS. 12A and 12B initiates a cutting operation by positioning the cutting tip 184 to abut the implant 112 disposed in the rod-receiving portion 122 of the distal tip 102, as shown in FIGS. 12A-12B. To achieve this, the inner sleeve 108 can be rotated relative to the outer sleeve 101 as shown by the arrow 1202 to reduce the distance between the drive feature 195 and the proximal end of the tube 104 from the distance D1 shown in FIG. 11B to the distance D2 shown in FIG. 12B. As noted above, rotation of the inner sleeve 108 relative to the outer sleeve 101 can cause the threaded surface 192 of the inner sleeve 108 to rotate along the threads 194 of the tube 104 while exerting a distally-directed force onto the anvil 168 to translate the anvil 168 towards the implant. Continued rotation of the inner sleeve 108 can further distally advance the anvil 168 beyond the configuration shown in FIGS. 12A and 12B to advance the anvil through the implant 112 and sever it into two pieces.

Cutting operations can exert high axial loads on the instrument 100. Various features or additional use steps can be included to address the forces experienced during use. In various embodiments, for example, different thread forms can be utilized based on the expected forces involved in cutting implants with different sizes and geometric configurations, or implants formed from different materials (e.g., materials of different hardness, etc.). In certain embodiments, thread forms with fine pitch and high tolerances can be utilized. In some embodiments, single lead thread forms can be utilized, while in other embodiments multiple-lead thread forms can be utilized, such as the triple lead Acme centralizing thread mentioned above. In addition, in some embodiments various coatings can be provided on the threads to reduce friction during actuation. For example, a diamond-like carbon (DLC) coating can be provided on the threads, or they can be electropolished to minimize friction during use under axial loading.

Figure 13A:
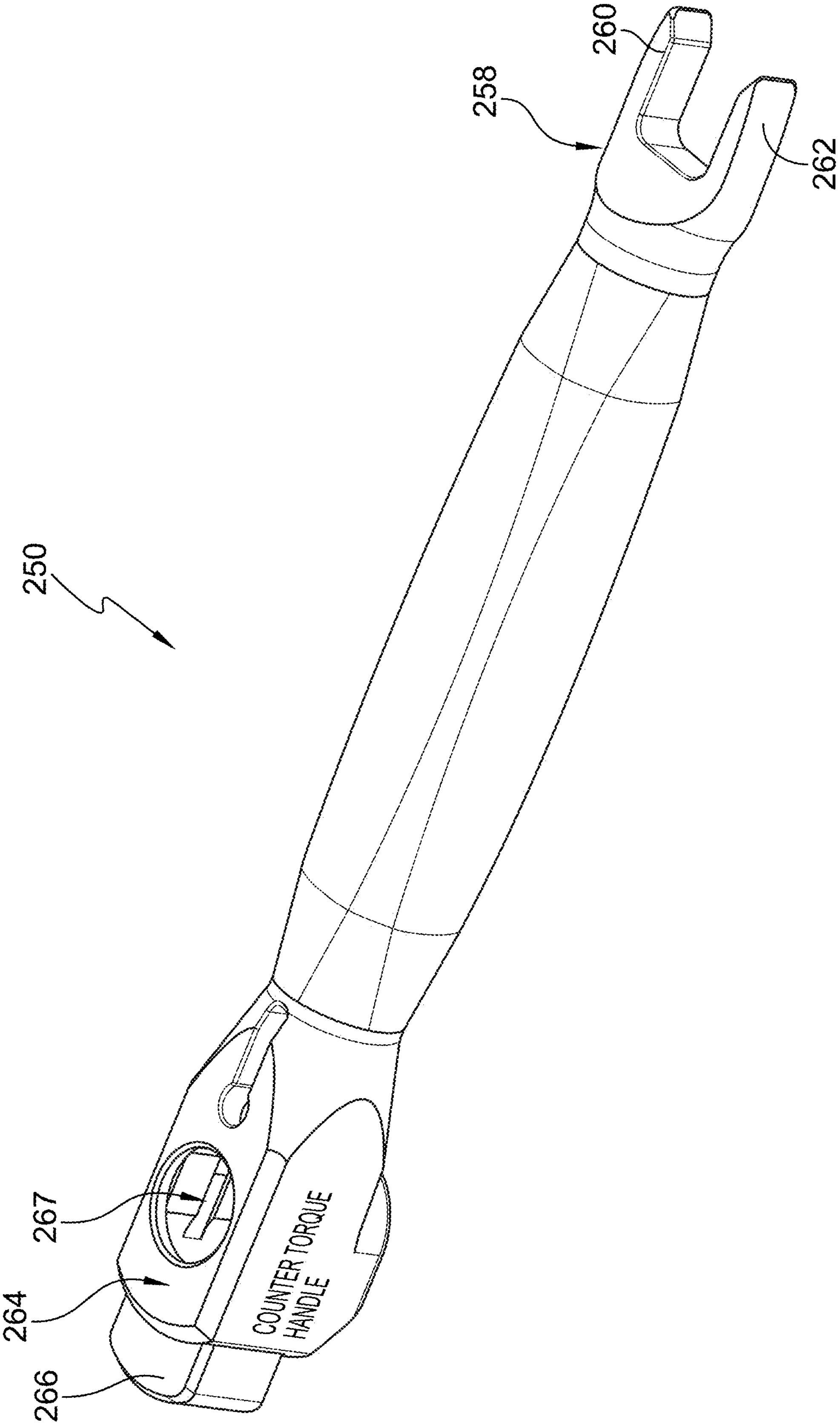
FIG. 13A is a perspective view of one embodiment of a counter-torque handle configured to be used with the cutting instruments of the present disclosure.
Figure 13B:
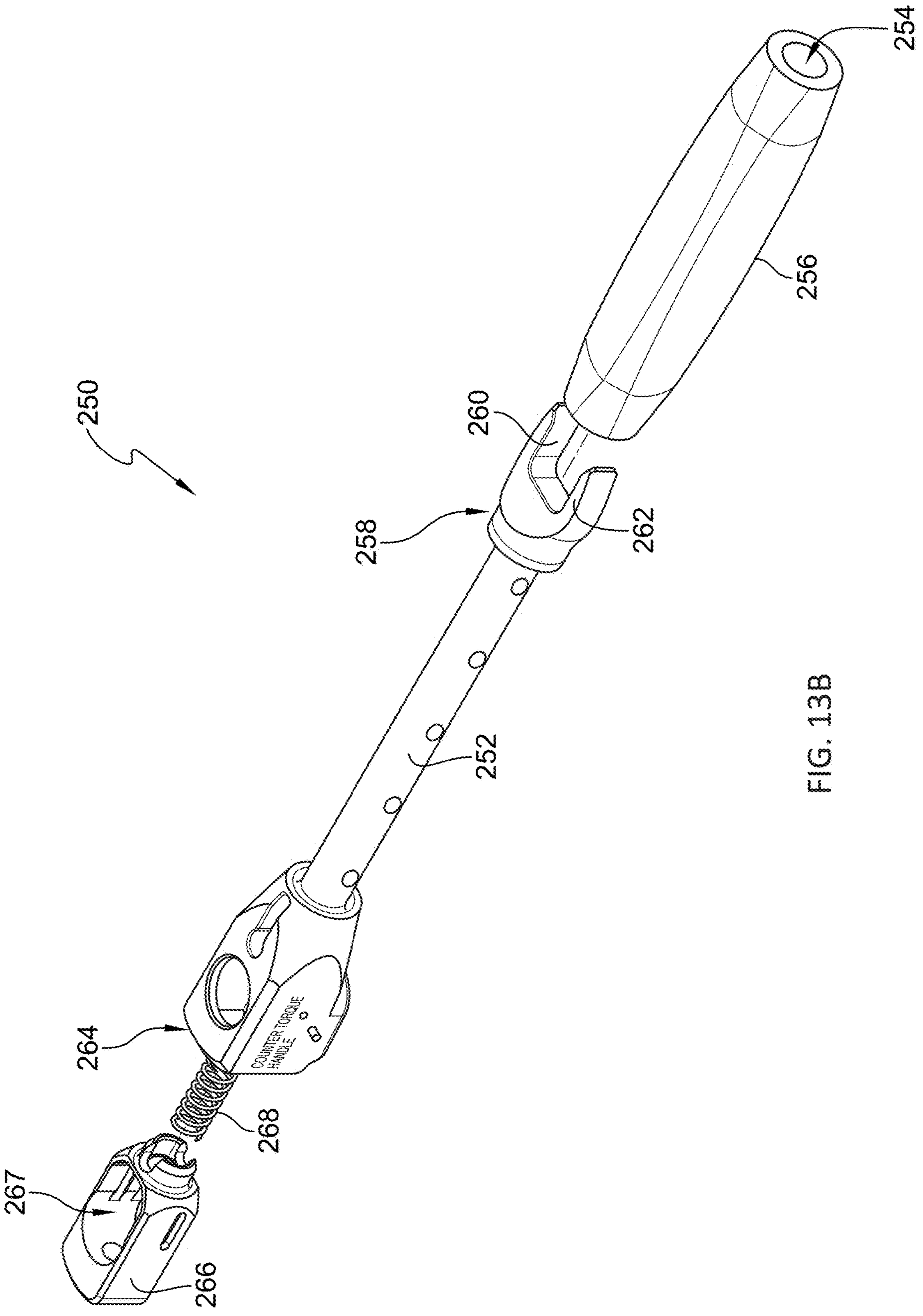
FIG. 13B is an exploded view of the counter-torque handle of FIG. 13A.

Moreover, in some embodiments additional components can be included to reduce friction under loading or better handle loading forces, such as bearings incorporated between the inner and outer sleeves to maintain positioning and facilitate smooth relative movement. In certain embodiments, one or more additional components can be used to engage a portion of the cutting instrument 100 to help handle loading forces. For example, a counter-torque implement can be coupled to the outer sleeve 101 to prevent rotation thereof when rotating the inner sleeve 108 during a cutting operation. FIGS. 13A-13B illustrate one example of a counter-torque handle 250 that can be used with the cutting instrument 100 of the present disclosure. The counter-torque handle 250 can include a shaft 252 disposed within a channel 254 of a handle 256. The handle 256 can include gripping features (e.g., knurling, ridges, recesses, finger loops, etc.) to facilitate a user grasping the handle during operation. The counter-torque handle 250 can include one or more features for engaging the cutting instrument 100 to facilitate rotation of the inner sleeve 108 relative to the outer sleeve by resisting any rotation of the outer sleeve along with the inner sleeve. For example, the shaft 252 can terminate at one end with a fork 258 having prongs 260, 262. An opposite end of the shaft 252 can include a housing 264 having a spring-loaded coupler 266 disposed therein. The coupler 266 can be moved relative to the housing 264 by exerting a force thereon that compresses a spring 268. The coupler 266 can include a bore formed therein with one or more ridges formed around a partial circumference thereof.

In use, the coupler 266 can be pressed inward against the spring bias force and positioned over a proximal end of another component, such as the counter-torque feature 148 of the tube 104. Once positioned, the coupler 266 can be allowed to move outward under the spring bias force such that the one or more ridges formed around a partial circumference of the bore engage a portion of the component disposed within the bore, such as opposed flats 149 of the counter-torque feature 148 of the tube 104. In such a configuration, the counter-torque handle 250 can be prevented from rotating relative to the tube 104 and can therefore be utilized to impart counter-torque to the tube 104 when rotating the inner sleeve 108. In addition, the coupler 266 can also interface with a groove or other feature to prevent unintended axial separation of the counter-torque handle 250 from the captured component. For example, a portion of the coupler 266 can extend into the groove 147 formed on the tube 104 to prevent separation of the two components until a user depresses the coupler against the spring bias. Alternatively, the forked end of the counter-torque handle 250 can be used in a similar manner, i.e., by disposing the opposed forks 260, 262 against opposed flats 149 of the counter-torque feature 148 of the tube 104 in order to allow use of the handle 250 to provide counter-torque when rotating the inner sleeve 108.

Figure 14:
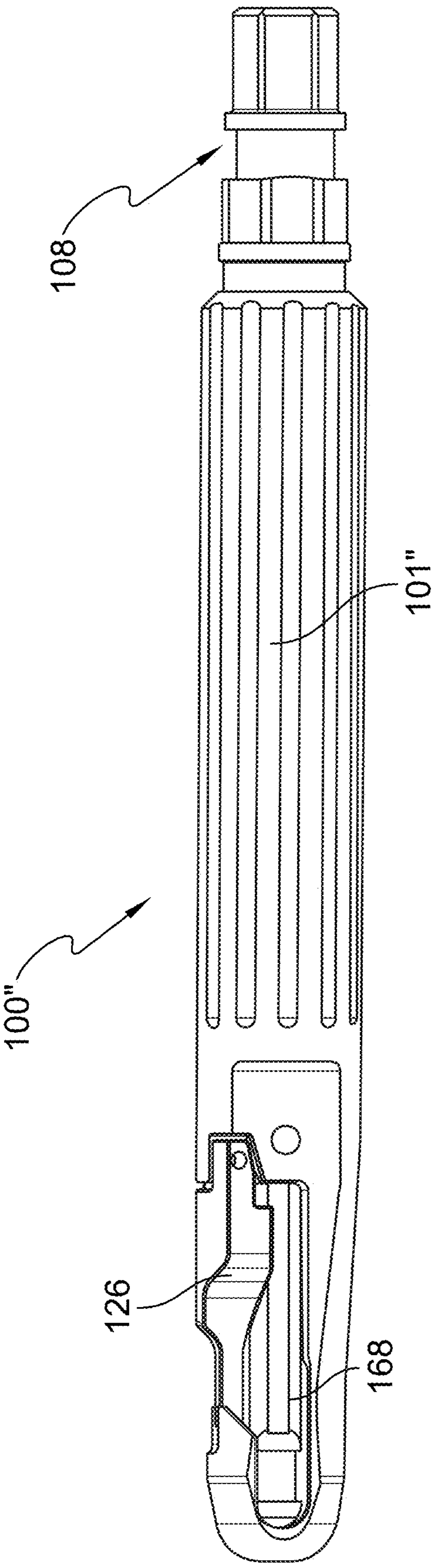
FIG. 14 is a side view of a cutting instrument having a single-piece outer sleeve without a separable distal cutting tip.

The above-described embodiments have shown a modular configuration in which a base tube 104 can be selectively coupled to a variety distal cutting tips 102 to form the outer sleeve 101 of the instrument, wherein the different distal cutting tips can be configured to cut implants of different sizes, shapes, materials, etc. In some embodiments, however, the cutting instrument can have a more unitary, non-modular construction. For example, FIG. 14 illustrates one embodiment of a cutting instrument 100" having a single-piece or unitary outer sleeve 101" without a separable distal cutting tip. As mentioned above, the cutting instrument 100" can be similar to the cutting instrument 100 in many respects and, as a result, a detailed description of every feature is omitted for the sake of brevity. As shown, the outer sleeve 101" can receive the inner shaft 108 and anvil 168 therethrough in a similar manner as the assembled outer sleeve 101 described above to cut an implant disposed in a distal portion of the outer sleeve 101". Even though the outer sleeve 101" may not accommodate different distal cutting tips, it is possible to utilize different anvils 168 having differently configured cutting tips 184 in the same manner that can be done with the cutting instrument 100 described above, which can provide for some flexibility to accommodate different implant sizes, geometries, materials, etc., even without a modular distal tip portion of the instrument outer sleeve.

Figure 15A:
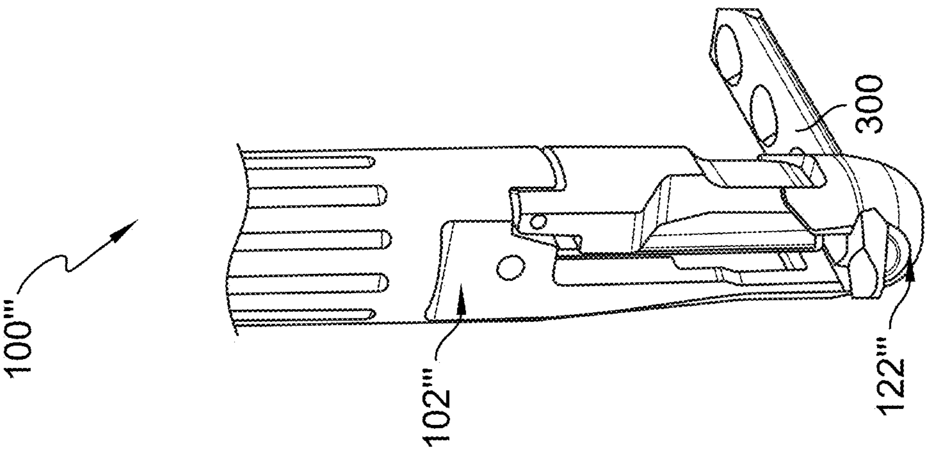
FIG. 15A is a perspective view of one embodiment of a distal tip of a cutting instrument receiving a plate transversely therethrough.
Figure 15B:
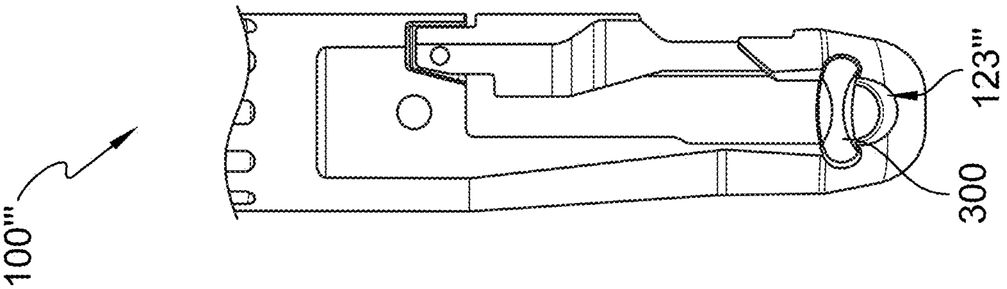
FIG. 15B is a side perspective view of the distal tip of FIG. 15A receiving the plate transversely therethrough.
Figure 15C:
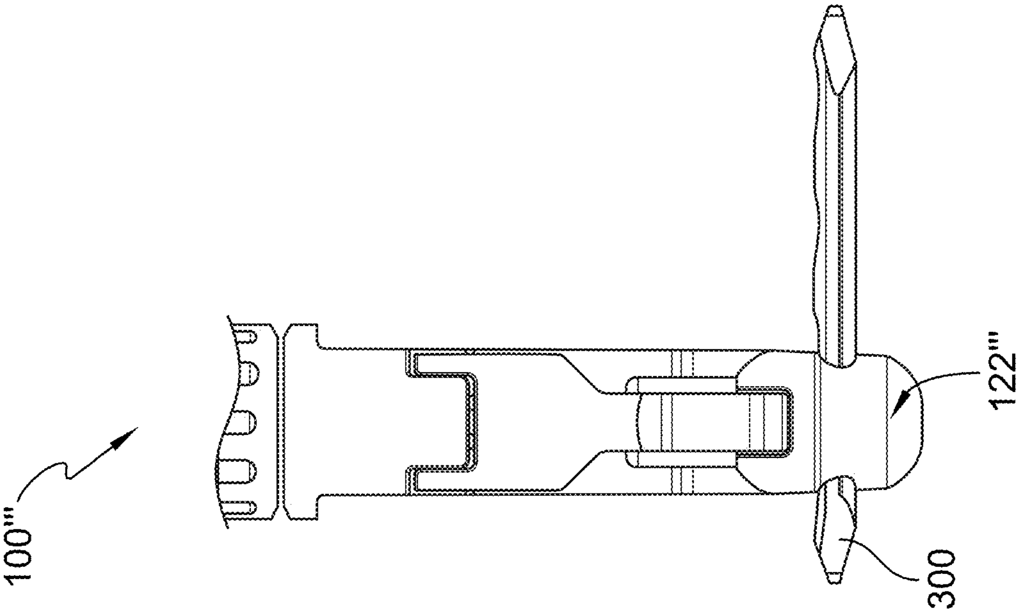
FIG. 15C is a front perspective view of the distal tip of FIG. 15A receiving the plate transversely therethrough.

Returning to the instrument 100, the modular configuration of the distal tip 102 and the base tube 104 can allow the cutting instrument 100 to be used to cut various types of implants. For example, in some embodiments, the distal tip 102 described above that can be particularly configured to cut spinal rods can be replaced with a distal tip 102'" that can be particularly configured to cut plates. FIGS. 15A-15C illustrate an embodiment of the distal tip 102'" for cutting a plate 300. As shown, the distal tip 102'" of the plate cutter 100"" can include an elongate slot 123"" that defines a plate-receiving portion 122'" configured to receive the plate 300 transversely therethrough. The distal tips 102'" can be configured to cut a variety of different bone plates, such as craniomaxillofacial (CMF) plates, various trauma plates, etc. In some embodiments, a shape of the plate-receiving portion 122'" and the distal tip 102'" can be customized to fit a size and shape of a particular plate being cut. In some embodiments, however, the distal tip 102 of a cutting instrument can be configured to accommodate a plurality of different implants, such as various rods, plates, screws, and so forth.

Figure 16A:
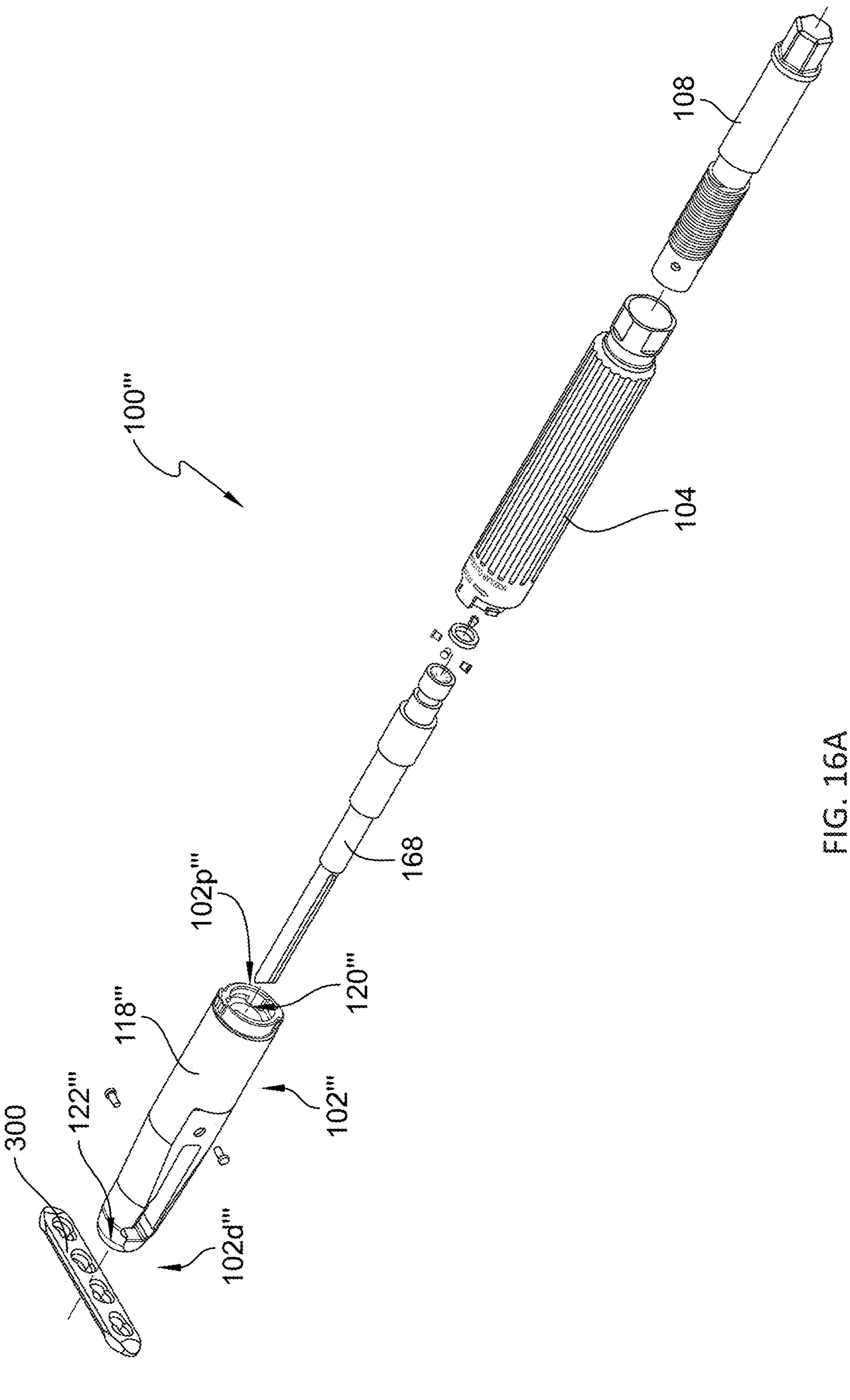
FIG. 16A is an exploded view of the cutting instrument of FIG. 15A and the plate.
Figure 16B:
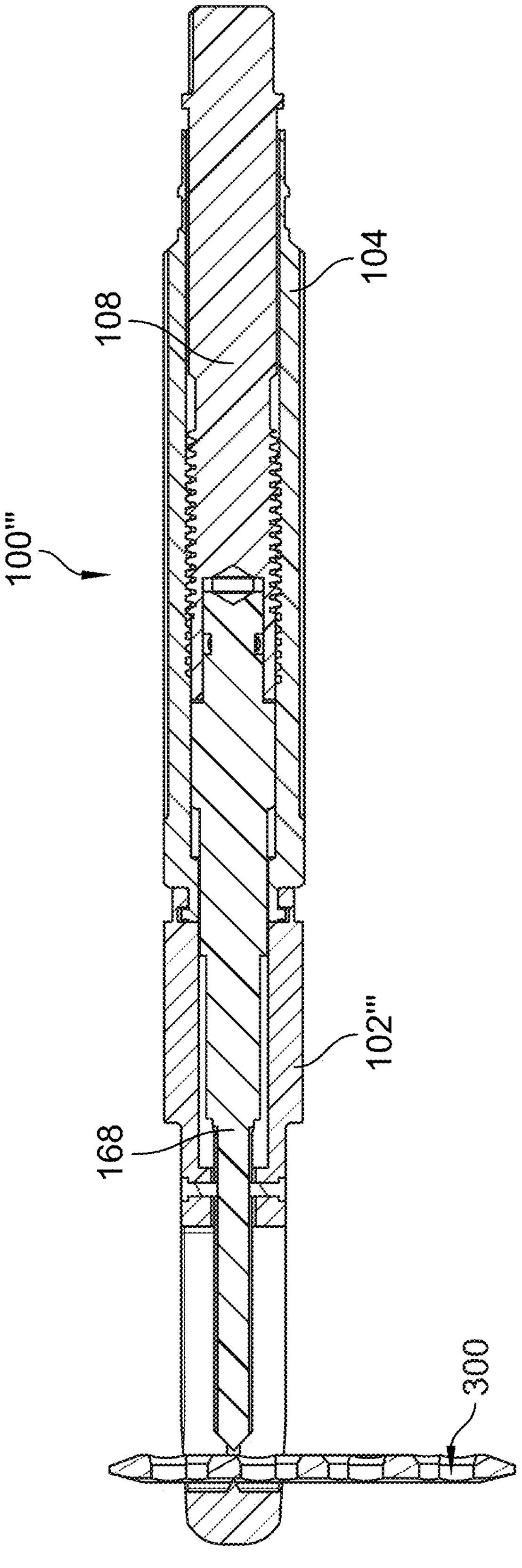
FIG. 16B is a longitudinal cross-sectional view of the instrument and plate of FIG. 15A.

FIGS. 16A-16B illustrate the plate cutter 100'" of the present disclosure in more detail. As mentioned above, the plate cutter 100"" can be similar to the cutting instrument 100 in many respects and, as a result, a detailed description of every feature is omitted for the sake of brevity. As shown, the plate cutter 100"" can include the distal tip 102'", the base tube 104, the inner shaft 108, and the anvil 168. The distal tip 102'" can include a cylindrical sidewall 118'" that defines a lumen 120'". The lumen 120"" can extend substantially through a length of the distal outer sleeve 102'" from a proximal end 102*p*"" to a distal end 102*d*'" thereof to receive the anvil 168. The plate 300 can be disposed in the plate-receiving portion 122"". The sidewall 118" of the distal outer sleeve 102'" can be substantially continuous such that it includes no breaks formed therein to have a capture arm disposed therethrough.

FIGS. 17A-17K illustrate one example method of using the instruments disclosed herein for cutting a spinal rod using the cutting instrument 100. Except as indicated below, the steps of the described method can be performed in various sequences and one or more steps can be omitted or added. A detailed description of every sequence of steps is omitted here for the sake of brevity.

Figure 17A:
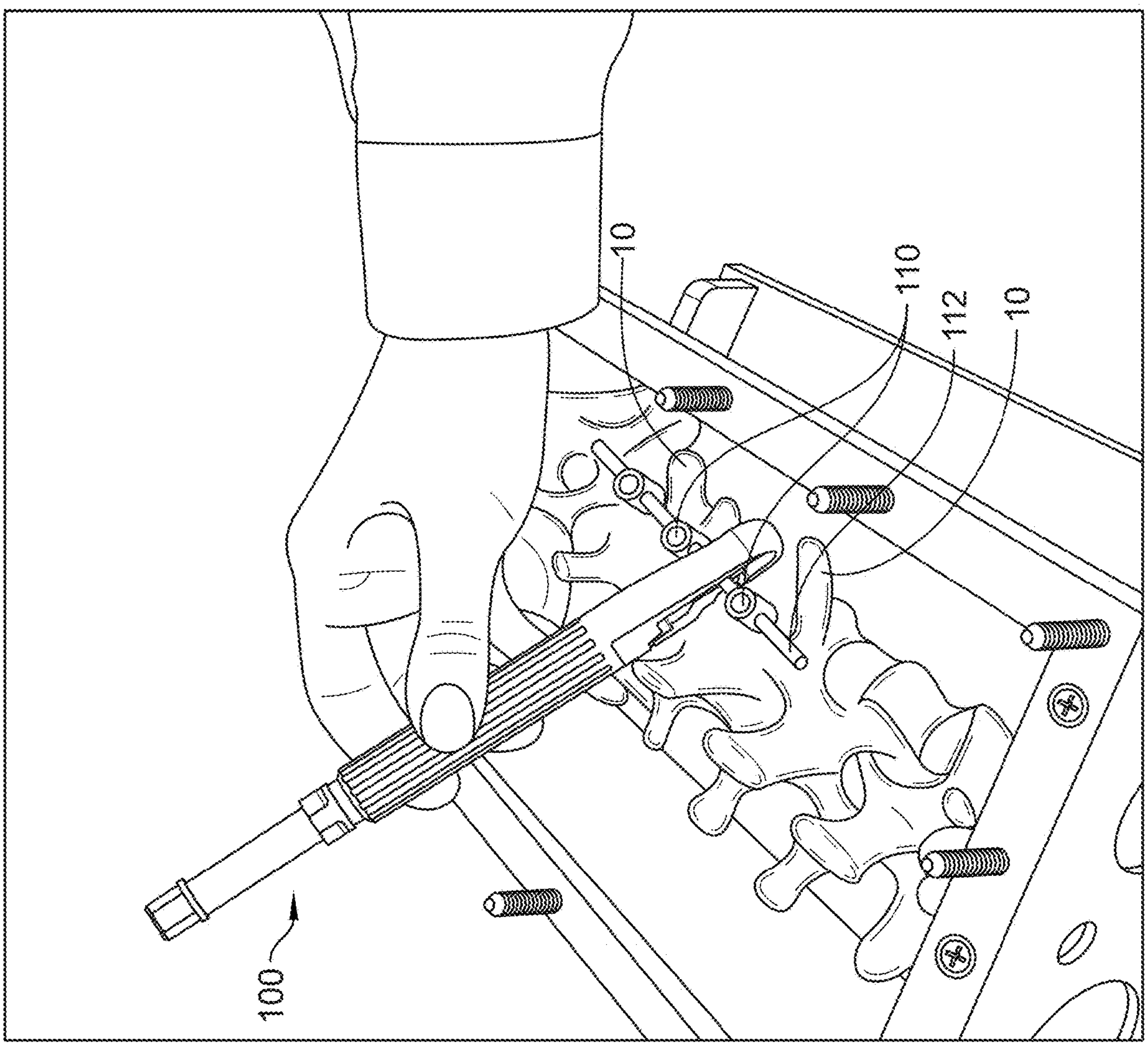
FIG. 17A is a perspective view of one embodiment of using the cutting instrument of FIG. 1A in an initial configuration.

FIG. 17A illustrates the cutting instrument 100 in its initial configuration being coupled to a spinal rod 112 that is disposed between adjacent bone anchors 110 implanted within vertebrae 10. The cutting instrument 100 can be positioned to engage the rod 112 between the bone anchors 110 to cut a section of the rod positioned therebetween.

Figure 17B:
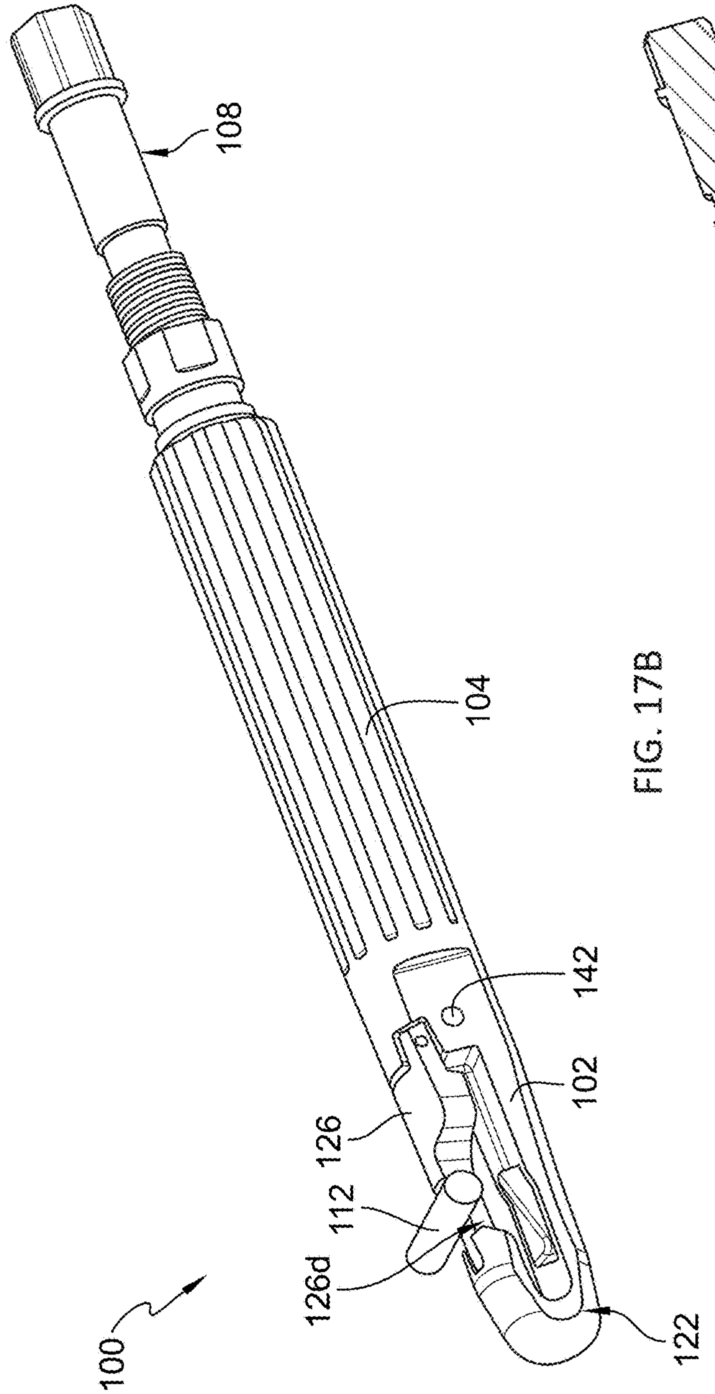
FIG. 17B is a perspective view of the cutting instrument of FIG. 17A being coupled to a spinal rod.
Figure 17C:
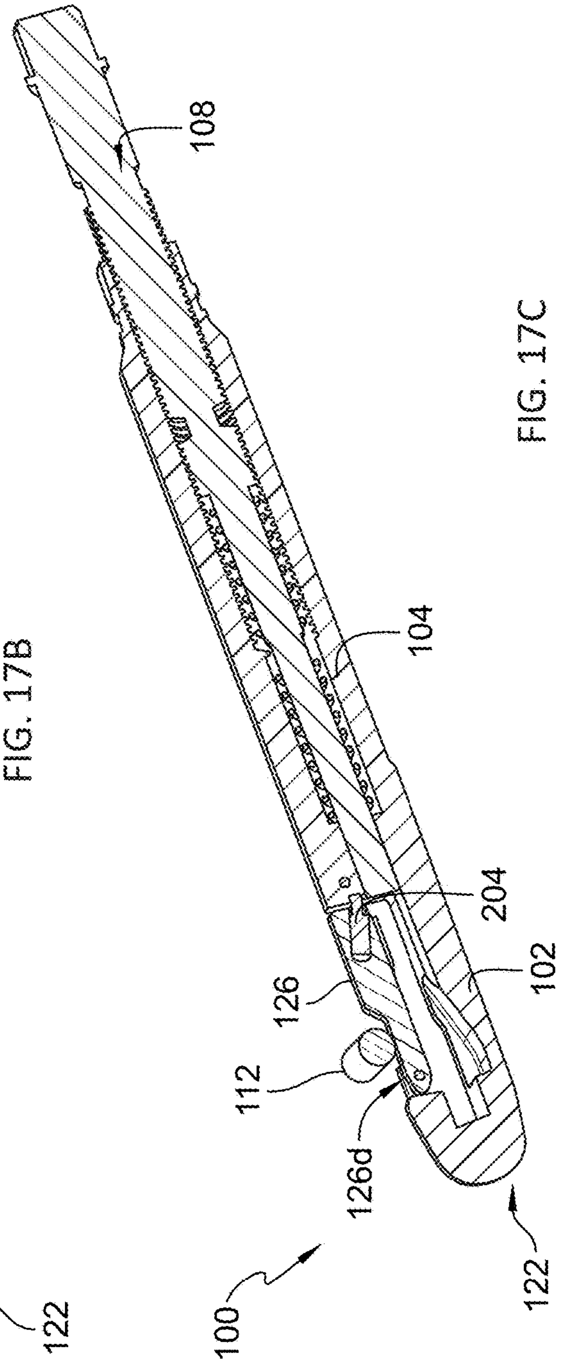
FIG. 17C is a longitudinal cross-sectional view of the cutting instrument of FIG. 17A being coupled to a spinal rod.
Figure 17D:
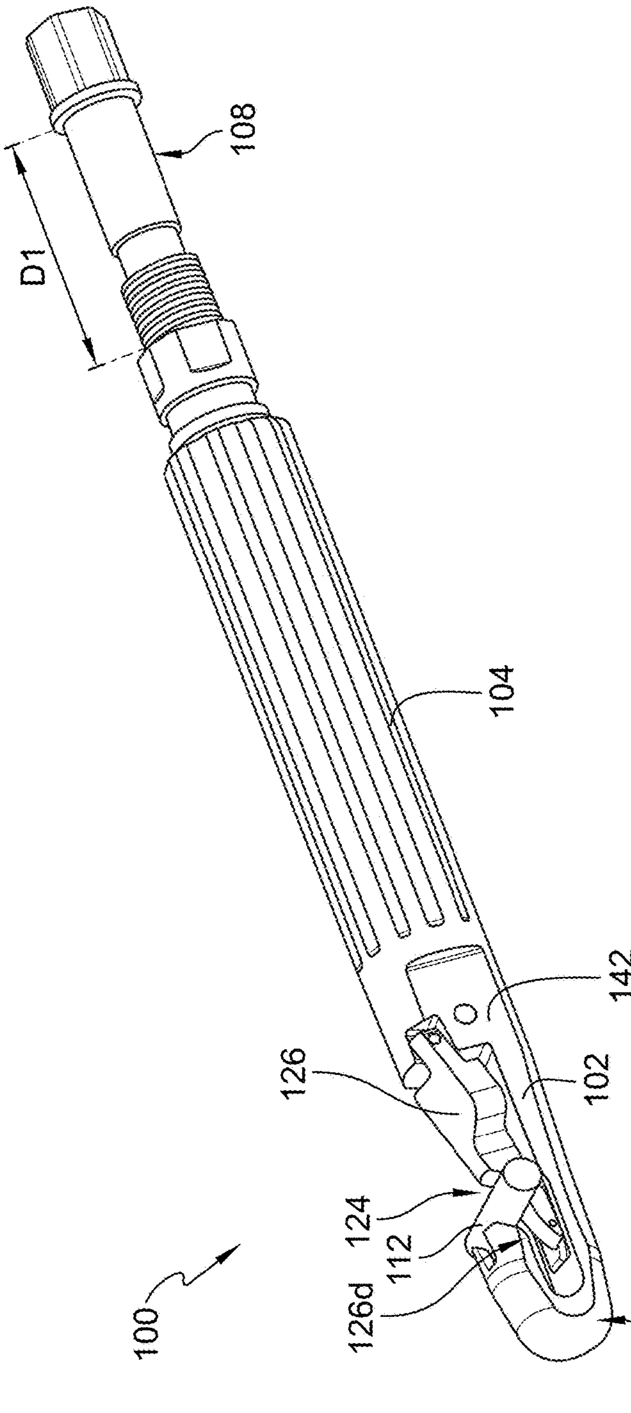
FIG. 17D is a perspective view of the a capture arm of the cutting instrument of FIG. 17A deflecting radially inward to allow the spinal rod to pass into the opening.
Figure 17E:
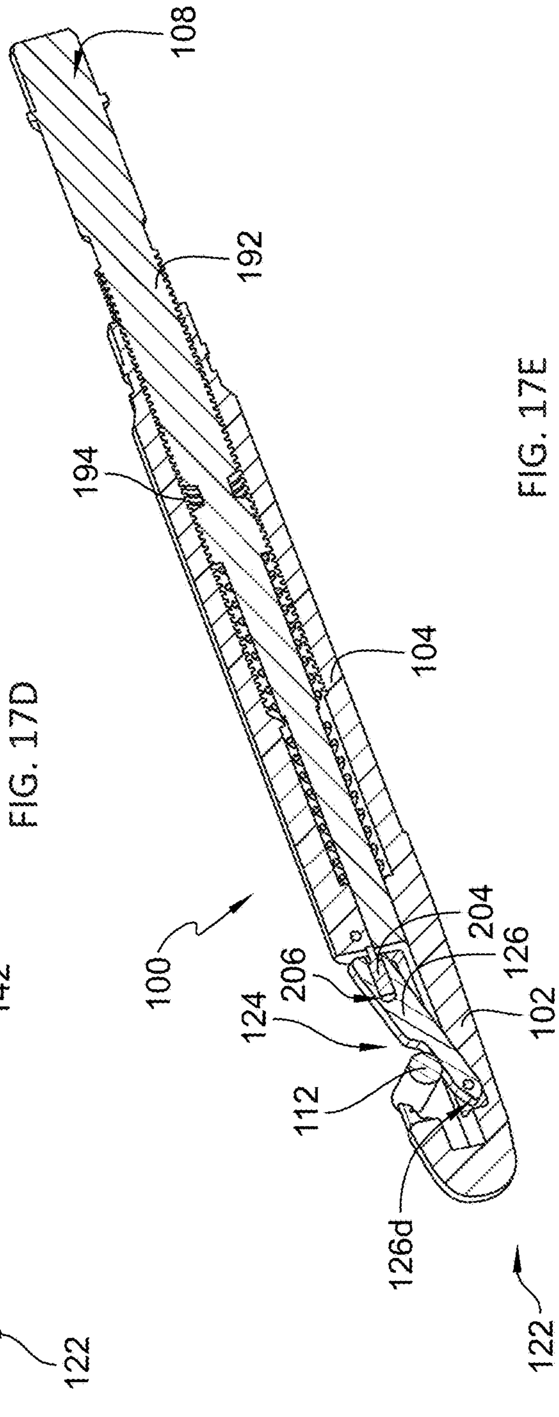
FIG. 17E is a longitudinal cross-sectional view of the capture arm of the cutting instrument of FIG. 17A deflecting radially inward to allow the spinal rod to pass into the opening.

The rod 112 can be disposed within the cutting instrument 100 by side-loading. For example, as shown in FIGS. 17B and 17C, the cutting instrument 100 can be brought into contact with the spinal rod 112 such that the capture arm 126 abuts the spinal rod 112. The force of the spinal rod 112 on the distal end 126*d* of the capture arm 126 can cause the capture arm 126 to deflect radially inward to allow the rod to pass through the opening 124 into the rod-receiving portion 122, as shown in FIGS. 17D and 17E.

Figure 17F:
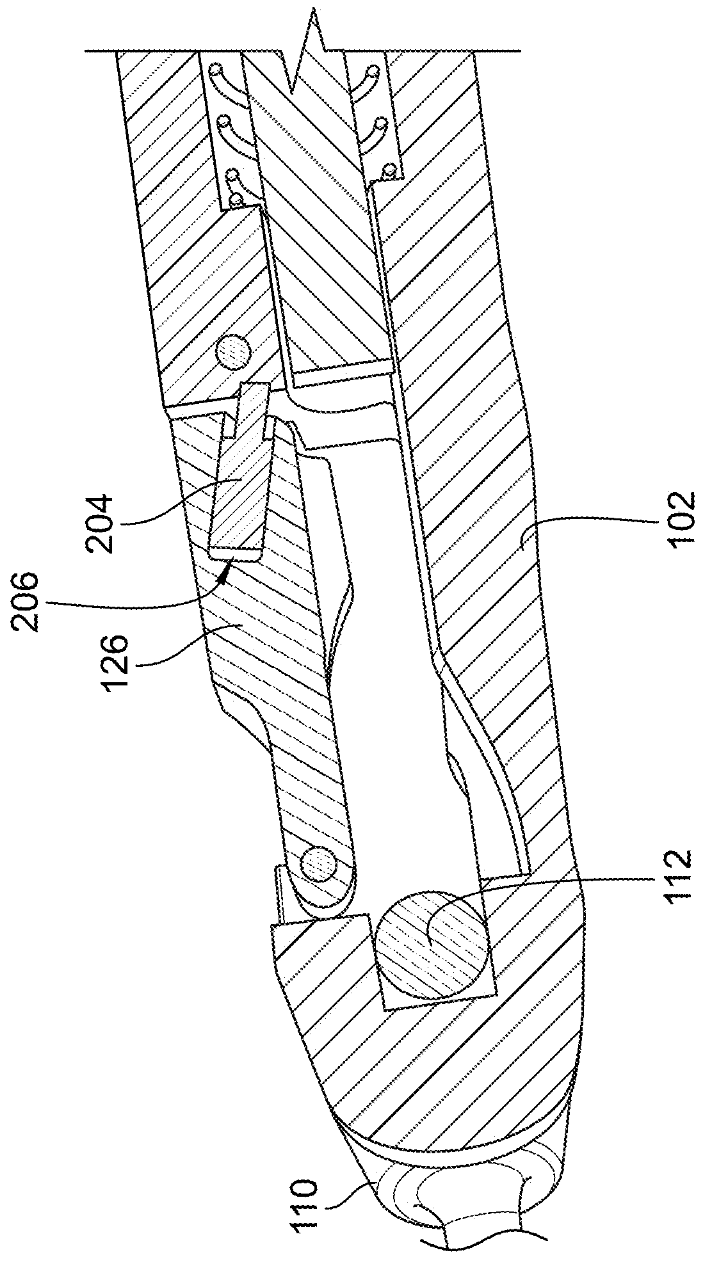
FIG. 17F is a longitudinal cross-sectional view of the capture arm of the cutting instrument of FIG. 17A pivoted back into place after coupling to the spinal rod.
Figure 17G:
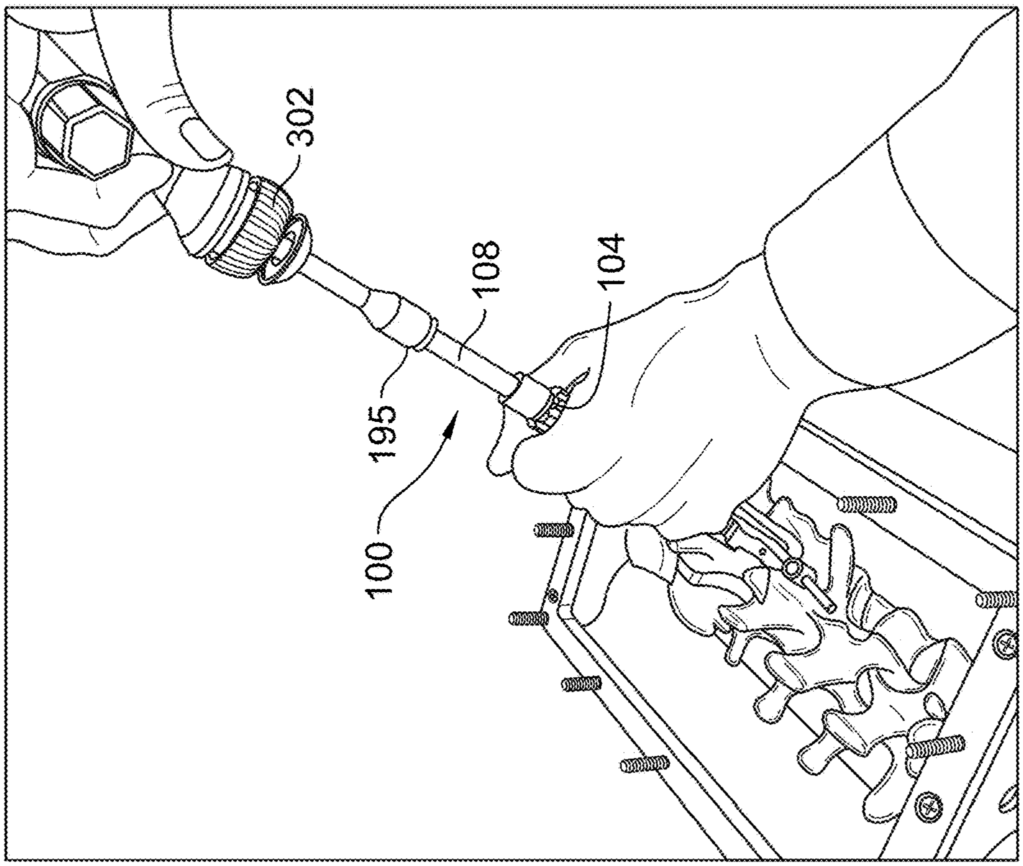
FIG. 17G is a perspective view of a manual driver attached to a drive feature of the cutting instrument of FIG. 17A.
Figure 17H:
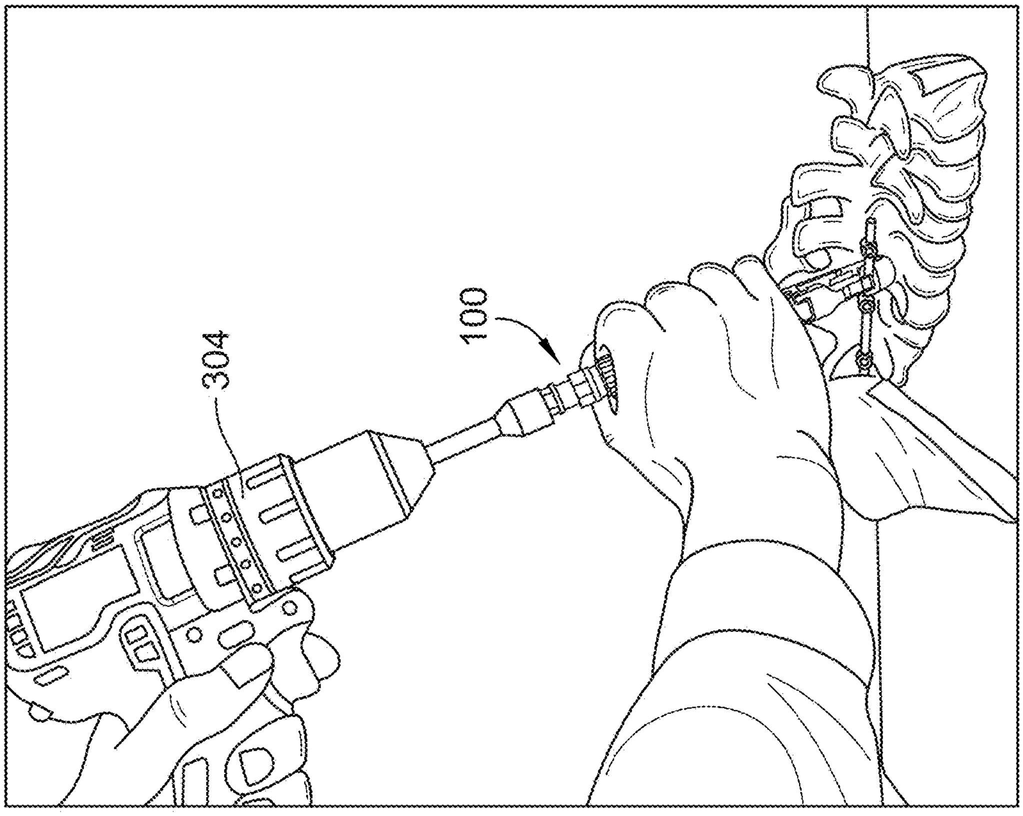
FIG. 17H is a perspective view of a powered driver attached to a drive feature of the cutting instrument of FIG. 17A.

Once the rod is seated in the rod-receiving portion 122, the capture arm 126 can move radially outward and snap back into place to secure against the rod passing back out of the opening 124 and separating from the instrument 100. As shown in FIG. 17F, the spring 204 can exert a biasing force onto the capture arm 126 to pivot the capture arm 126 back into place to block the opening 124 after the rod 112 is no longer in contact with the arm exerting a force on it. After the rod 112 is secured within the rod-receiving portion 122, a manual driver 302, e.g., a hex driver, can be attached to the drive feature 195 of the inner sleeve 108, as shown in FIG. 17G. The driver 302 can rotate the inner sleeve 108 and thereby advance it distally relative to the tube 104. In the illustrated embodiment, a user is manually grasping the tube 104 to provide counter-torque during rotation of the inner sleeve 108 via the driver 302. Distal advancement of the inner sleeve 108 can drive the anvil 168 distally. Alternatively, in some embodiments, a powered driver 304 can be used to rotate the inner sleeve 108 in lieu of the manual driver 302, which can enable in situ powered rod cutting without the use of a specialty powered cutter in the operating room. That is, any typical powered driver can be utilized to impart the torque necessary to cut an implant without the need for a specialty powered instrument. The ability of the cutting instrument 100 to be used with a conventional powered instrument, such as the driver 304, can reduce the inventory of instruments required in the operating theater, as well as reduce time spent cutting implants and required force application from a user to perform a rod cutting operation.

Figure 17I:
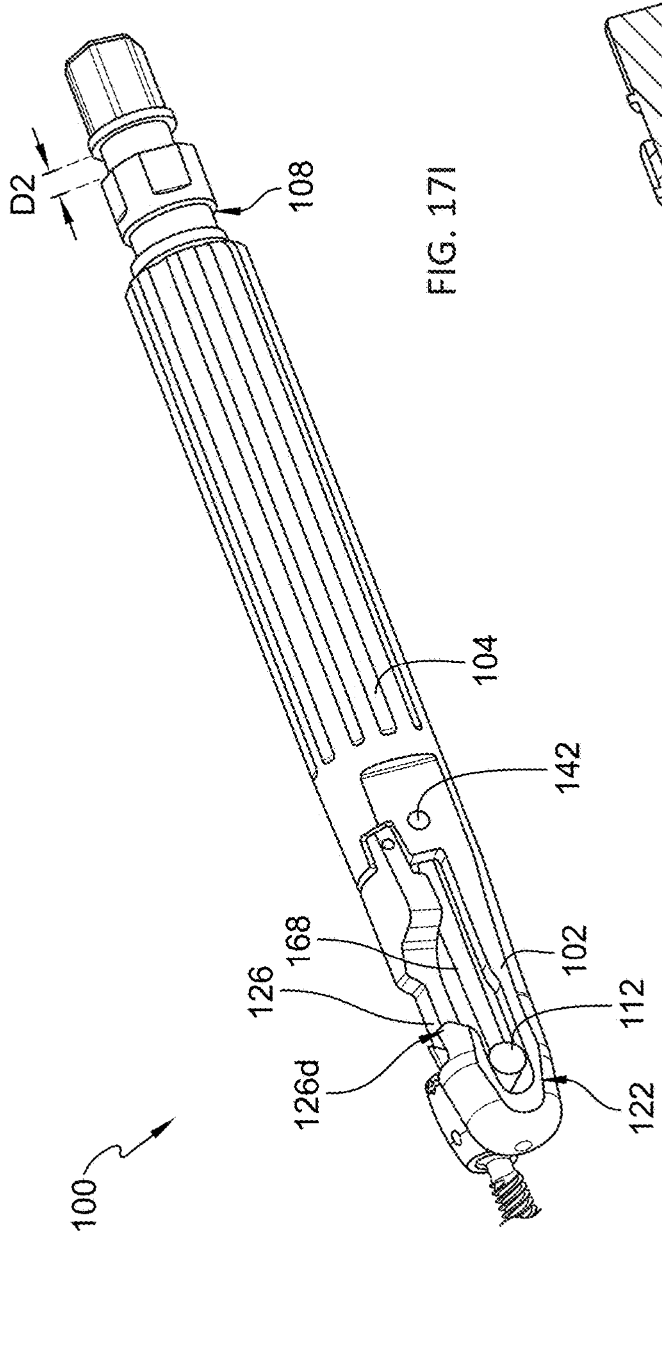
FIG. 17I is a perspective view of the cutting instrument of FIG. 17A with the anvil translated distally until the cutting tip abuts the spinal rod.
Figure 17J:
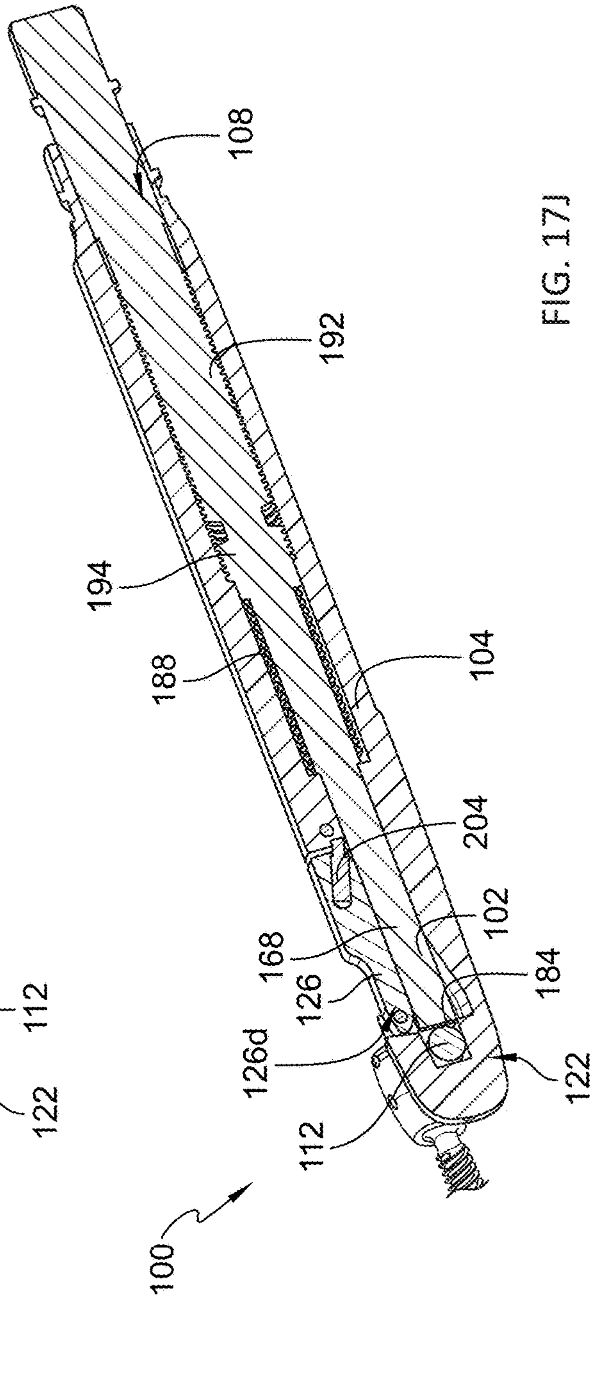
FIG. 17J is a longitudinal cross-sectional view of the cutting instrument of FIG. 17A with the anvil translated distally until the cutting tip abuts the spinal rod.
Figure 17K:
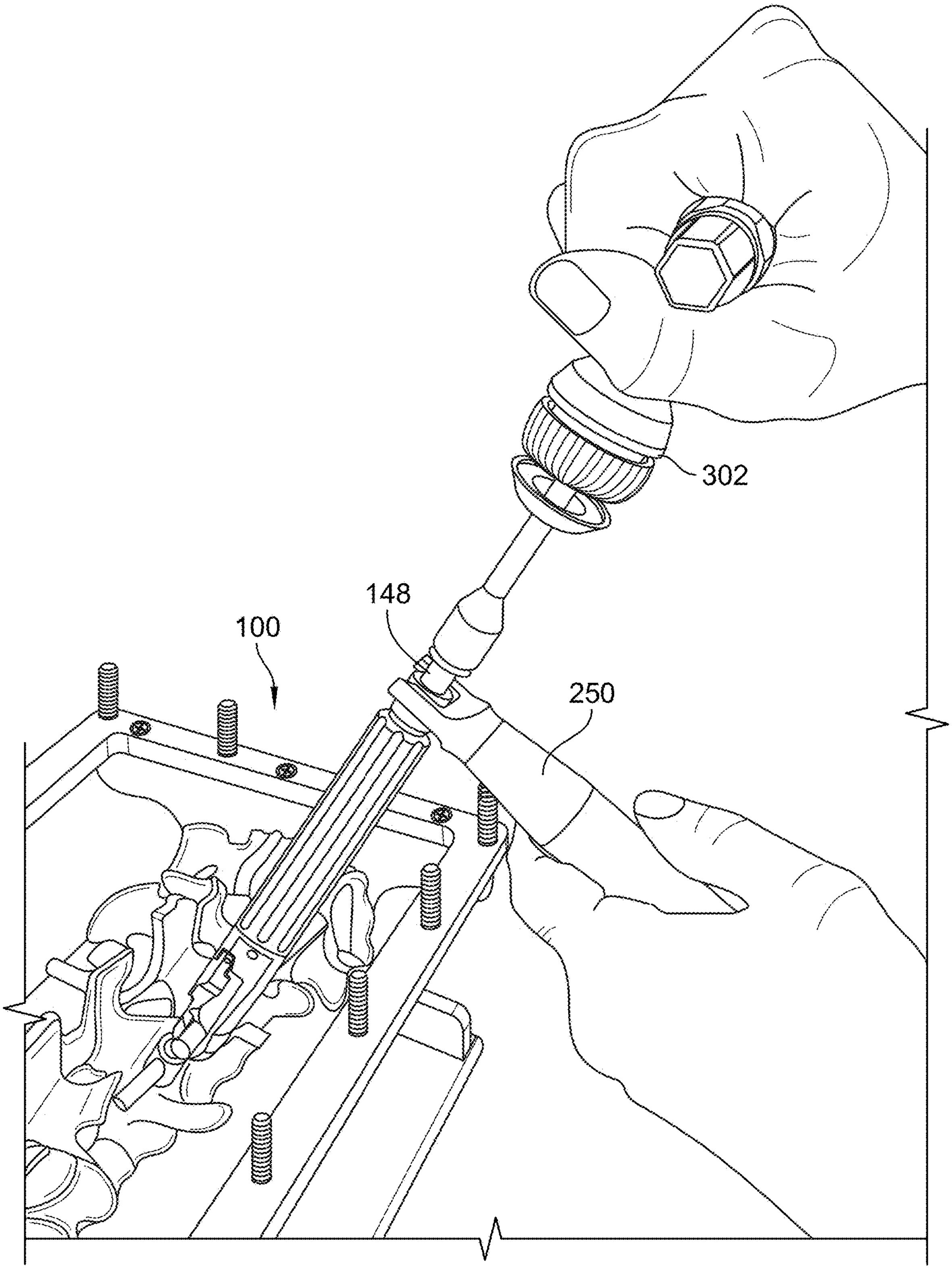
FIG. 17K is a perspective view of the counter-torque handle of FIG. 13A applied to the cutting instrument of FIG. 17A.

As shown in FIGS. 17I and 17J, rotation of the inner sleeve 108 can cause translation of the anvil 168 distally until the cutting tip 184 abuts the rod 112. During rotation of the inner shaft 108, counter-torque force can be applied onto the outer sleeve 101 via, e.g., the tube 104. As shown in FIG. 17G, a user can manually grasp the tube 104 to provide counter-torque thereto and prevent corresponding rotation of the tube 104 when the driver 302 is actuated to rotate the inner sleeve 108. Alternatively, the counter-torque handle 250 can be coupled to the drive feature 148 of the tube 104 to prevent rotation thereof, as shown in FIG. 17K.

Continued application of force to the inner sleeve 108 by actuation of the driver 302 can continue to advance the anvil 168 distally until it splits the rod 112 in a controlled fashion.

After splitting an implant, the instrument 100 can be withdrawn from the surgical site and the driver 302 can be actuated in an opposite direction to proximally withdraw the anvil 168. At this point, the instrument can be reused, either in its existing configuration or after modularly swapping out one distal tip 102 for another, e.g., to facilitate cutting another implant of a different size, geometry, material, etc. In addition, the anvil can be replaced if needed. This can be done by continuing to rotate the inner sleeve 108 in a manner that withdraws it proximally relative to the outer sleeve 101 until the inner sleeve 108 separates from the base tube 104, allowing for complete withdrawal of the anvil 168 and inner sleeve 108 from the outer sleeve 101.

Figure 18A:
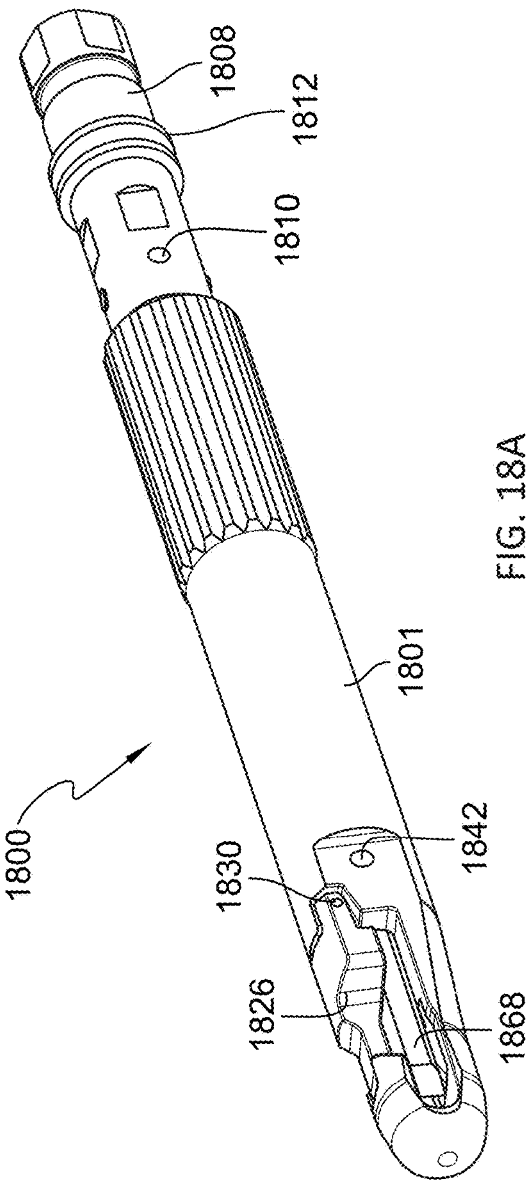
FIG. 18A is a perspective view of one embodiment of a cutting instrument of the present disclosure.
Figure 18B:
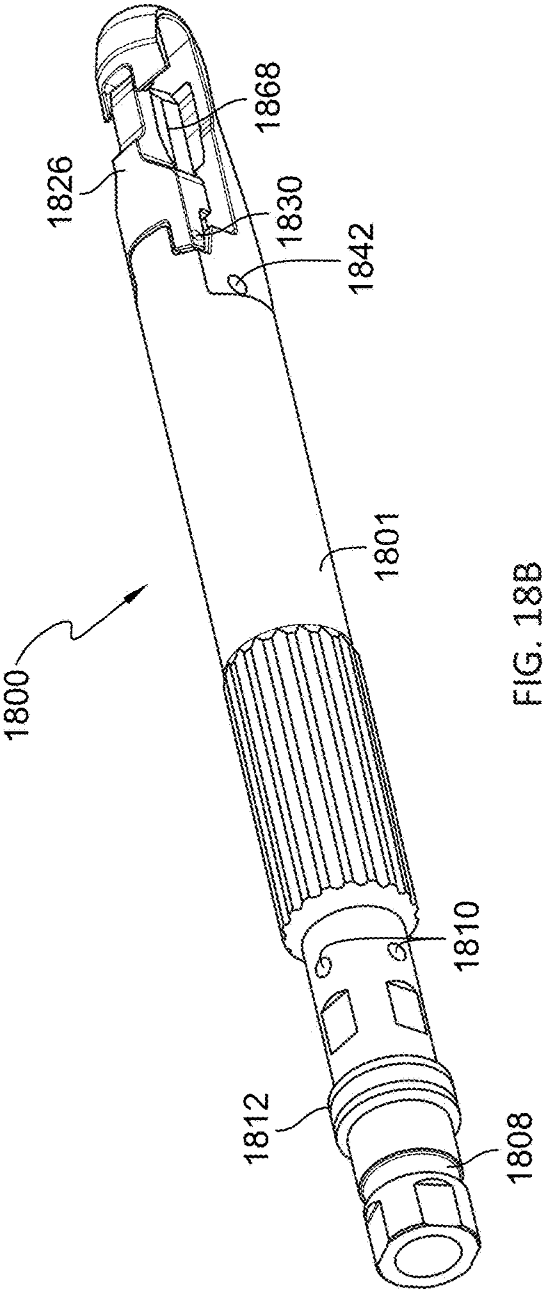
FIG. 18B is an alternate perspective view of the cutting instrument of FIG. 18A.
Figure 19:
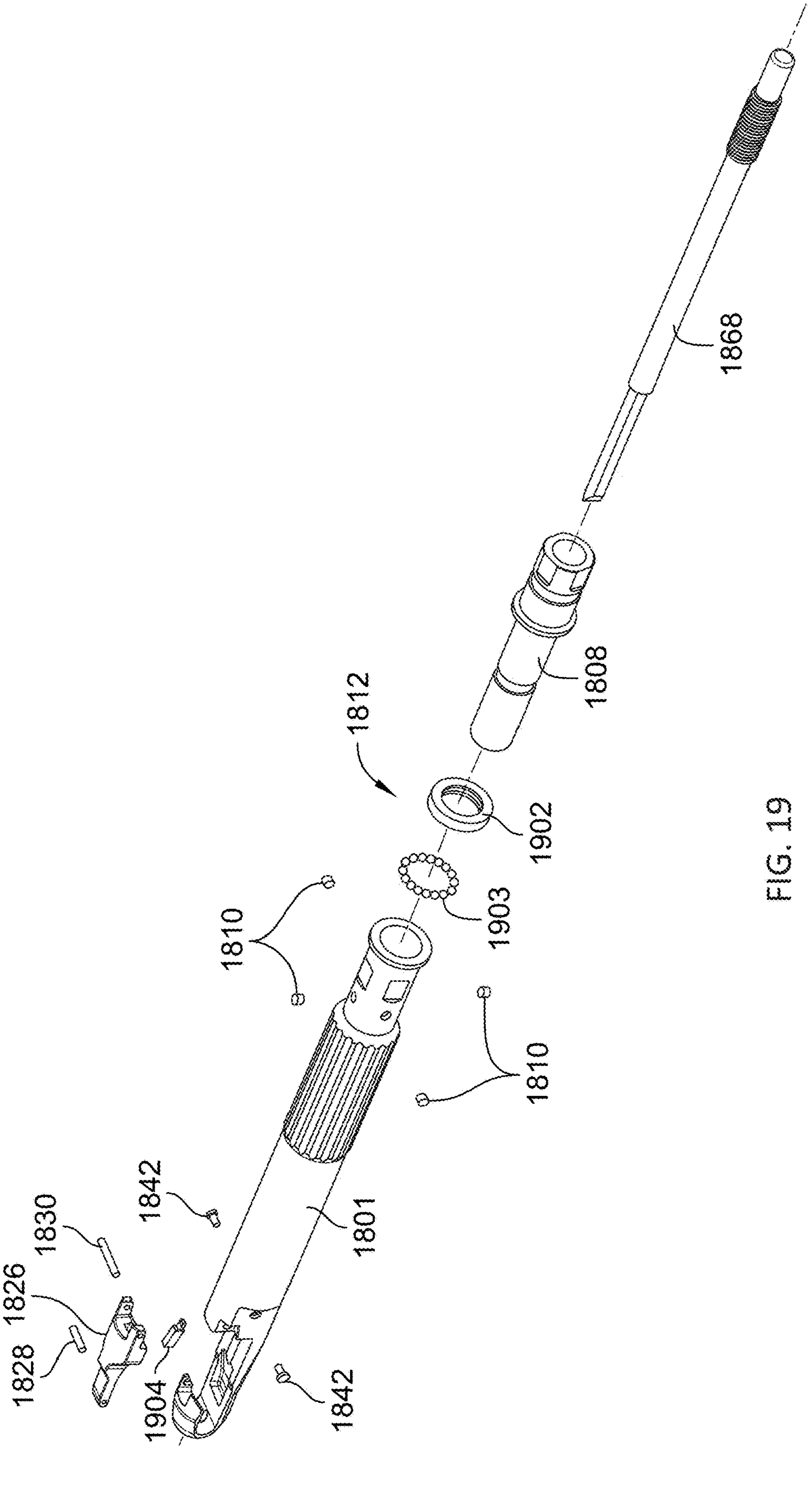
FIG. 19 is an exploded view of the cutting instrument of FIG. 18A.

FIGS. 18A-28 illustrate another embodiment of an instrument 1800 according to the present disclosure. As shown in FIGS. 18A-19, the instrument 1800 includes an outer sleeve 1801 with pivotably coupled capture arm 1826, inner sleeve 1808, and anvil 1868, similar to the instrument 100 described above. The distal end of the outer sleeve 1801 and capture arm 1826 can be similar to the embodiments described above, and a detailed description is therefore omitted. The proximal portion of the instrument 1800 can include a different configuration wherein the inner sleeve 1808 is configured to rotate relative to the outer sleeve 1801 but not translate relative thereto. This can be accomplished, for example, with one or more pins 1810 disposed through bores formed in the outer sleeve 1801 such that they extend into a groove 2102 (see FIGS. 21A-21B) formed in the inner sleeve 1808, thereby permitting relative rotation between the inner and outer sleeves 1808, 1801 while preventing relative translation therebetween. The inner sleeve 1808 thereby functions like a captured threaded nut at the proximal end of the outer sleeve 1801.

The anvil 1868 can be a single-piece or unitary inner shaft having a cutting tip 2384 (see FIGS. 23A-23B) disposed at a distal end thereof and one or more threaded portions 2392 formed proximal thereto. In addition, a distal portion of the anvil 1868 can include one or more flats or grooves 2390 that can interface with pins 1842 to prevent relative rotation between the anvil 1868 and the outer sleeve 101 while allowing for relative translation therebetween. The one or more threaded portions 1992 can interface with a threaded portion of the inner surface 2104 (see FIG. 21A) of the inner sleeve 1808 such that rotation of the inner sleeve 1808 relative to the outer sleeve 1801 causes translation of the anvil 1868 relative to the outer sleeve 1801.

To reduce friction and maintain alignment, especially during periods of high loading, such as while cutting an implant, the instrument 1800 can further include a thrust bushing or bearing 1812 disposed between the outer sleeve 1801 and the inner sleeve 1808. For example, an annular ball bearing 1812, including one or more races or carriers 1902 (see FIG. 19) and a plurality of balls 1903, can be disposed around the inner sleeve 1808 such that it is positioned between a proximal-facing surface 2002 (see FIG. 20A) of the outer sleeve 1801 and a distal-facing surface 2106 (see FIG. 21A) of a shoulder 2108 formed on the inner sleeve 1808. In other embodiments, for example, a polymer thrust bushing can be utilized in place of the annular thrust bearing.

Also shown in the exploded view of FIG. 19 is the pin 1830 that pivotably couples the capture arm 1826 to the outer sleeve 1801, as well as the pin 1828 disposed at a distal end of the capture arm 1826 such that ends thereof are received in recesses 2036 (see FIGS. 20A-20B) formed in the outer sleeve to increase the strength of the capture arm against axial loading during cutting operations. Further, the leaf spring 1904 or other lateral deflection biasing element is also shown in the exploded view and can be similar to the spring 204 described above.

Figure 20A:
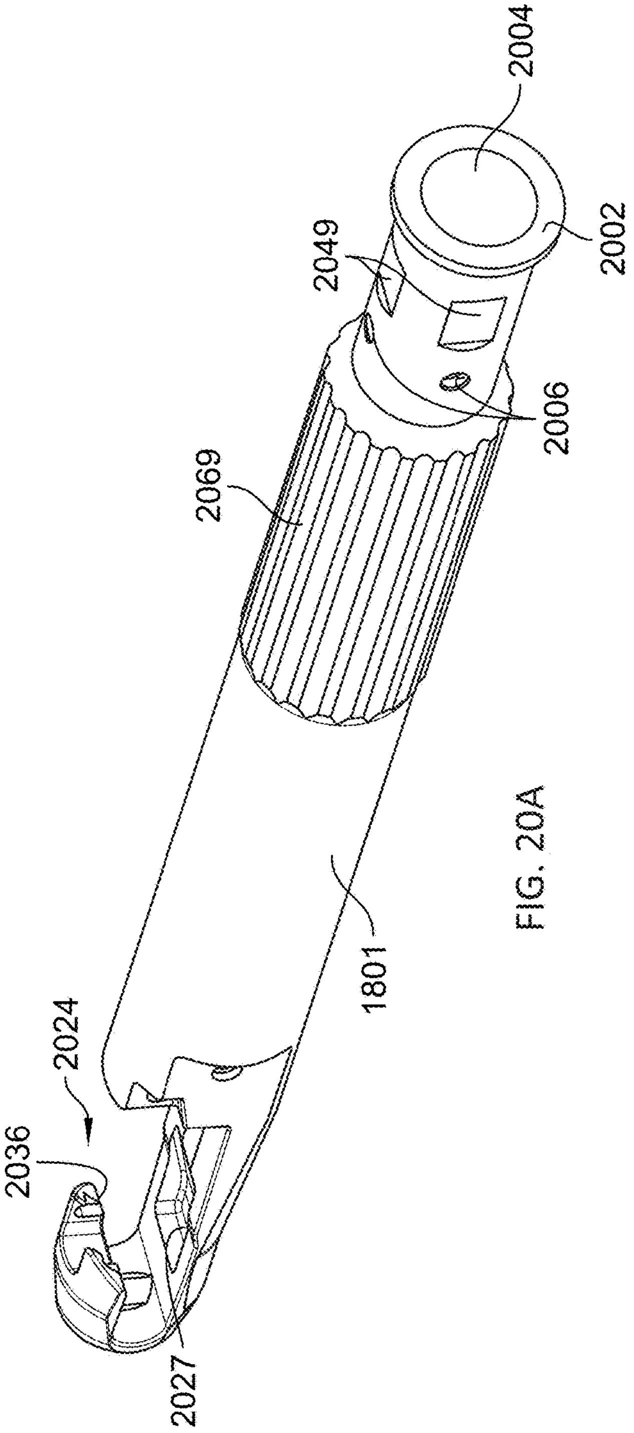
FIG. 20A is a perspective view of an outer sleeve of the cutting instrument of FIG. 18A.
Figure 20B:
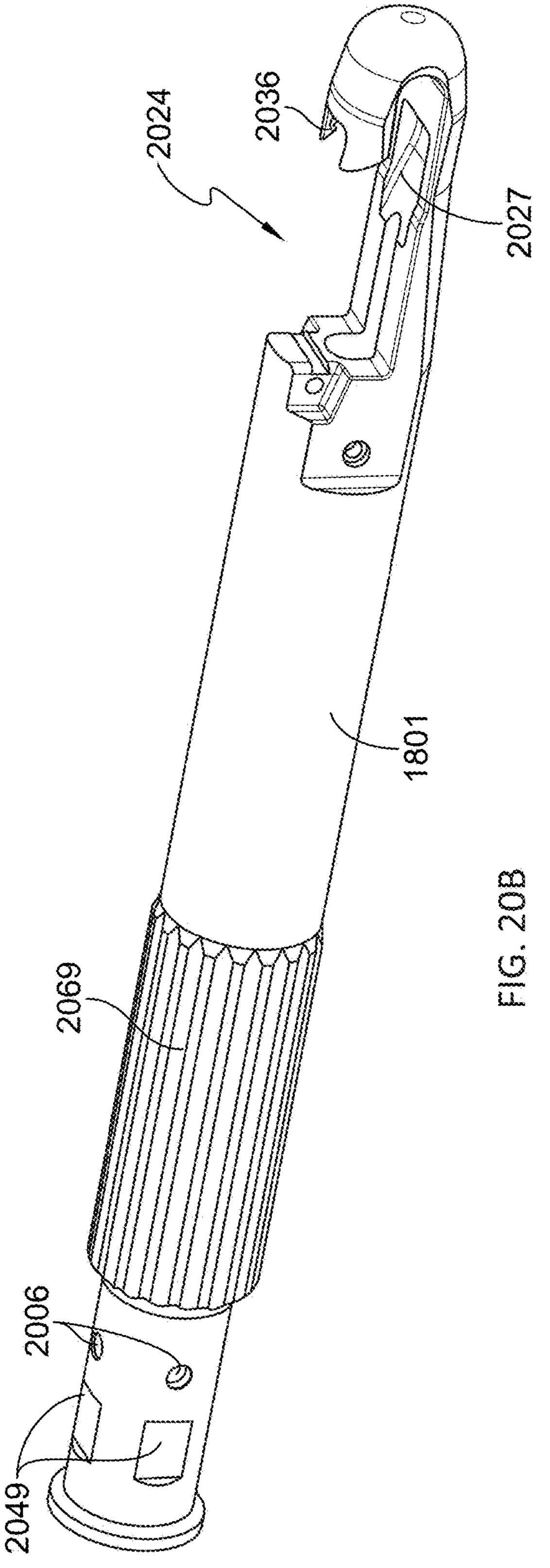
FIG. 20B is another perspective view of the outer sleeve of the cutting instrument of FIG. 18A.

FIGS. 20A and 20B illustrate the outer sleeve 1801 in greater detail. As noted above, the outer sleeve 1801 can be similar to the outer sleeve 101 described above. In the illustrated embodiment, the outer sleeve 1801 has a unitary, single-piece construction similar to the outer sleeve 101", though in other embodiments an outer sleeve with modular proximal and distal portions can be utilized such that different distal portions can be configured to receive various different implant geometries/types. The illustrated outer sleeve 1801 includes a similar hook-shaped distal portion with an opening 2024 formed on one side thereof that can receive the pivoting capture arm 1826, which can be similar to the capture arm 126 described above. The distal portion can also include a recess or pocket 2027 formed opposite the opening 2024 that can accommodate a portion of the capture arm 1826 when it pivots inward to expose the opening. Moreover, a proximal portion of the outer sleeve 1801 can include grip grooves 2069 formed thereon to facilitate a user grasping the outer sleeve, as well as one or more flats 2049 distributed around a circumference thereof to facilitate the application of torque to the outer sleeve.

In contrast to the outer sleeve 101 described above, the outer sleeve 1801 can include a thread-free inner surface 2004 given that the outer sleeve 1801 is not in threaded engagement with the inner sleeve 1808. Instead, the outer sleeve 1801 can include one or more bores 2006 formed therein and configured to receive the one or more pins 1810 that can ride in the groove 2102 of the inner sleeve 1808 to capture it and prevent relative translation between the inner and outer sleeves while permitting relative rotation therebetween.

Figure 21A:
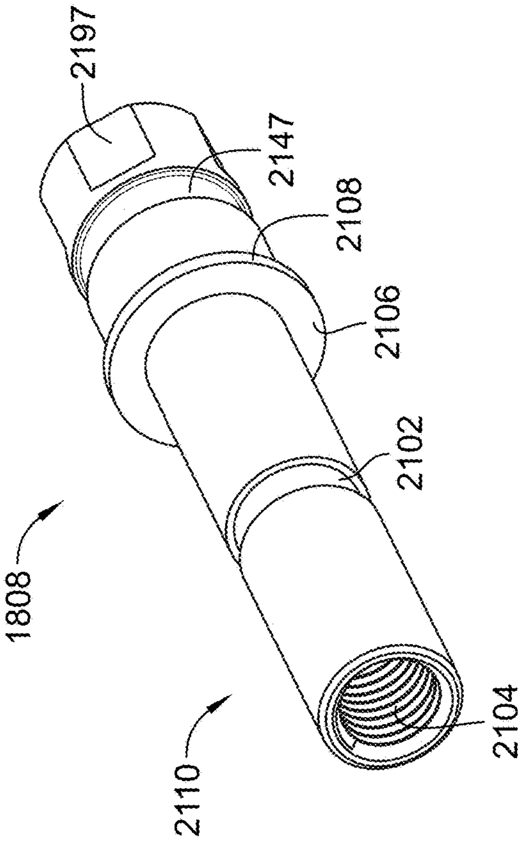
FIG. 21A is a perspective view of an inner sleeve of the cutting instrument of FIG. 18A.
Figure 21B:
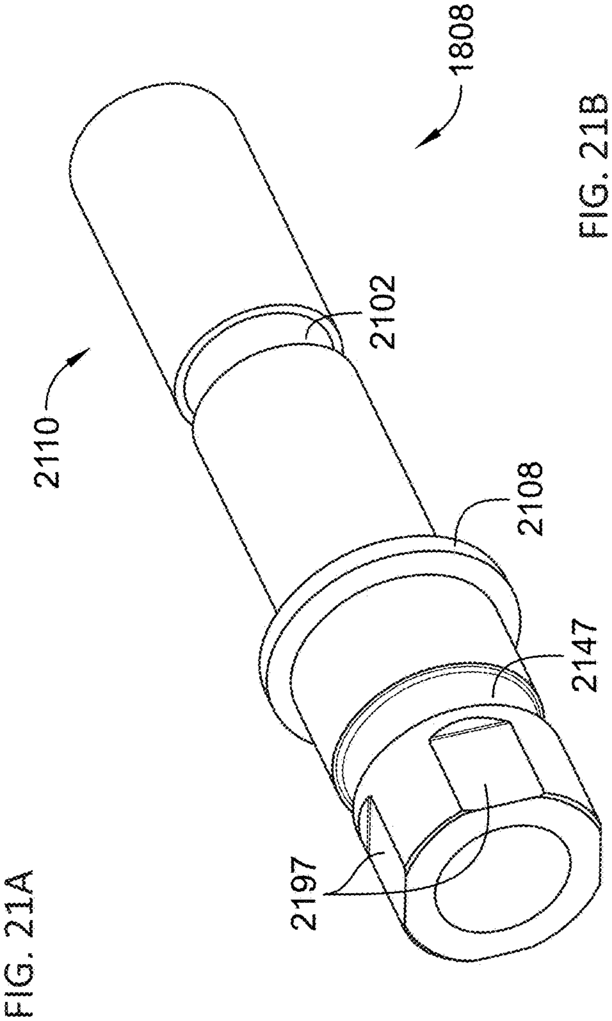
FIG. 21B is another perspective view of the inner sleeve of the cutting instrument of FIG. 18A.

FIGS. 21A and 21B illustrate the inner sleeve 1808 in greater detail. Shown in these figures is the smooth cylindrical distal portion 2110 that is configured to be received within the inner lumen of the outer sleeve 1801 when assembled. The distal portion 2110 also includes the groove 2102 that can receive the one or more pins 1810 disposed through the one or more bores 2006 formed in the outer sleeve 1801 in order to capture the inner sleeve 1808 against translation relative to the outer sleeve while allowing relative rotation therebetween. Further, and as noted above, the inner sleeve 1808 can include a shoulder 2108 with a distal-facing surface 2106 that can be configured to abut the thrust bushing or bearing 1812.

The inner sleeve 1808 can include an inner lumen extending therethrough with an inner surface having threads 2104 formed along at least a potion thereof. A variety of thread types can be utilized. In some embodiments, single-lead threads can be utilized to minimize friction. Standard V-threads are illustrated, but other thread forms can be utilized in some embodiments. For example, buttress or acme-style threads can also be utilized and can help maximize cutting force.

The inner sleeve 1808 can include features for applying torque thereto, similar to the inner sleeve 101 described above. For example, one or more flats 2197 can be disposed around a circumference of a proximal portion of the inner sleeve 1808. The one or more flats 2197 or other drive feature (e.g., a hex drive feature) can be configured to accept any of a manual driver handle and a powered driver. In addition, a groove 2147 can be provided in proximity to the one or more flats 2197 to facilitate coupling a counter-torque handle 250 thereto such that the components are locked against axial separation until a user intentionally decouples the handle from the inner sleeve 1808.

Figure 22:
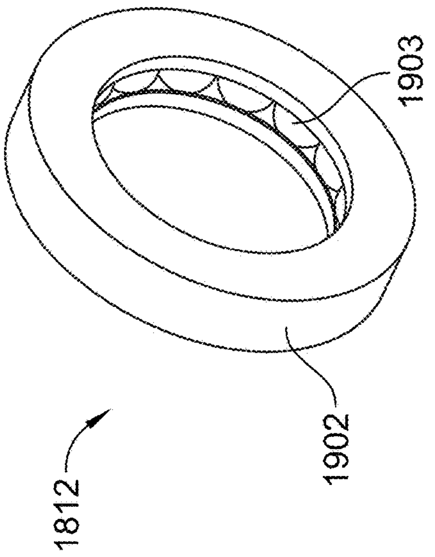
FIG. 22 is a perspective view of a bushing of the cutting instrument of FIG. 18A.

FIG. 22 illustrates the thrust bearing 1812 in greater detail. In the illustrated embodiment, the bearing includes one or more races or carrier 1902 and a plurality of balls 1903 that ride therein or therebetween. Reducing friction and maintaining alignment of components can be important for smooth operation of the instruments disclosed here, especially during times of high loading when cutting an implant. Use of a thrust bushing or bearing 1812 between the outer and inner sleeves 1801, 1808 can help provide for smooth operation of the instrument during cutting.

Figure 23A:
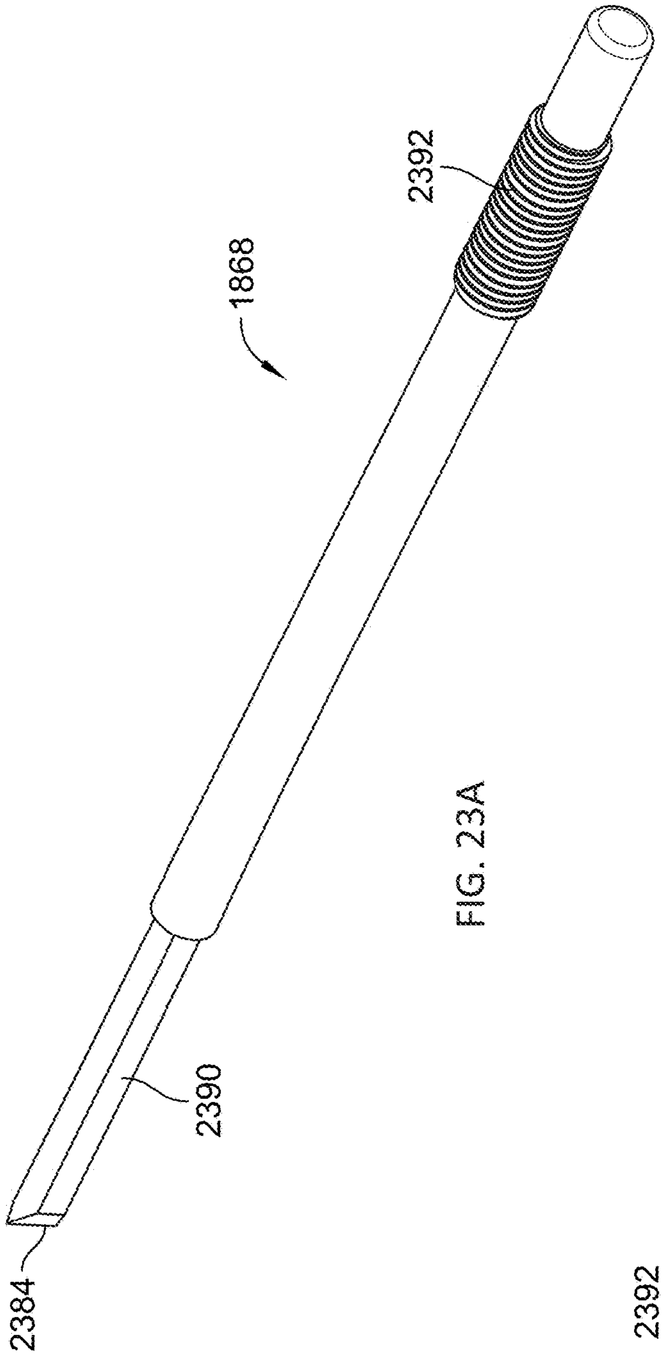
FIG. 23A is a perspective view of the anvil of the cutting instrument of FIG. 18A.
Figure 23B:
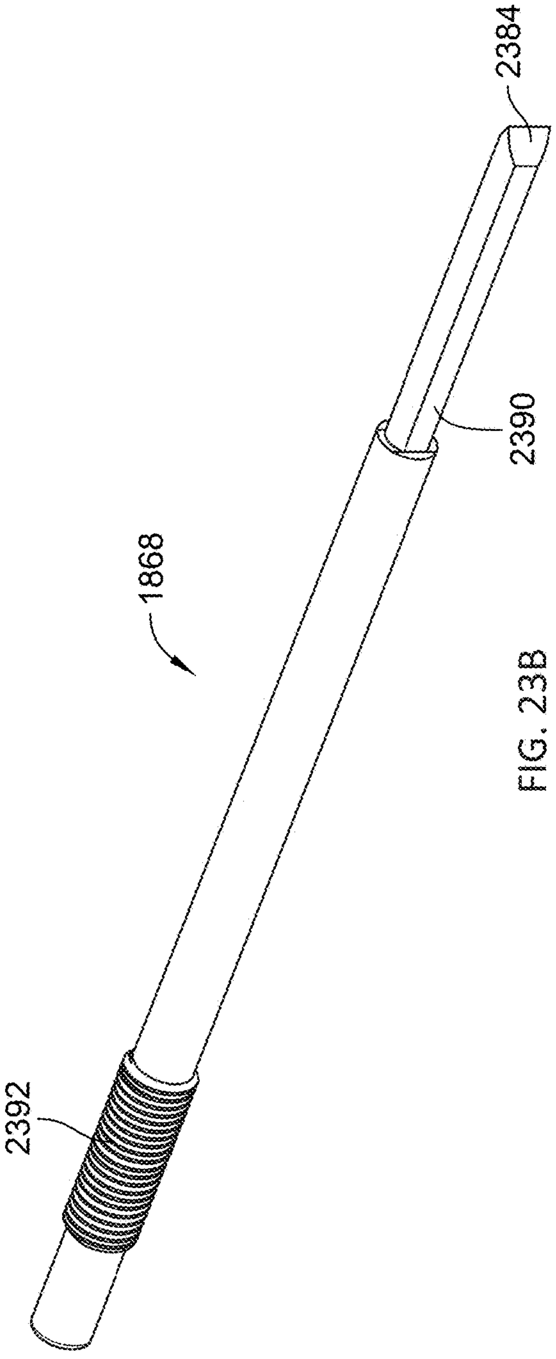
FIG. 23B is another perspective view of the anvil of the cutting instrument of FIG. 18A.

FIGS. 23A and 23B illustrate the anvil 1868 in greater detail. The anvil 1868 can be simplified relative to the assembly of the anvil 168 and inner sleeve 108 described above. In particular, the anvil 1868 can be a unitary, single-piece shaft having a distal cutting tip 2384 and one or more threaded portions 2392 positioned proximal thereto. Further, one or more flats or grooves 2390 can be positioned along a portion of a length thereof and configured to interface with pins 1842 to prevent relative rotation between the anvil 1868 and the outer sleeve 1801 while allowing relative translation therebetween. The anvil can be a single-use component or can be configured for re-use after cleaning, sharpening, etc. The anvil can also be made from a variety of materials and can include any of a variety of surface treatments. In some embodiments, for example, the anvil 1868 can be a single use component made from high strength steel and having a low-friction coating.

Figure 24A:
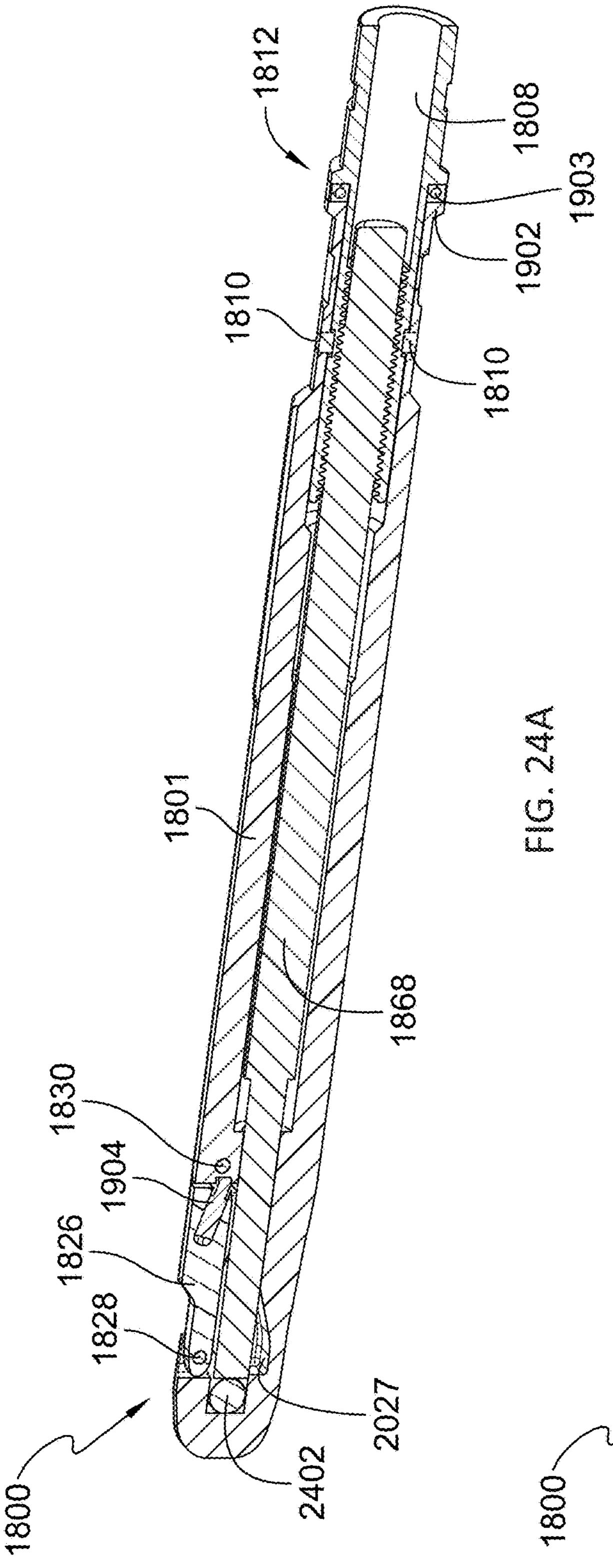
FIG. 24A is a longitudinal cross-sectional view of the cutting instrument of FIG. 18A.
Figure 24B:
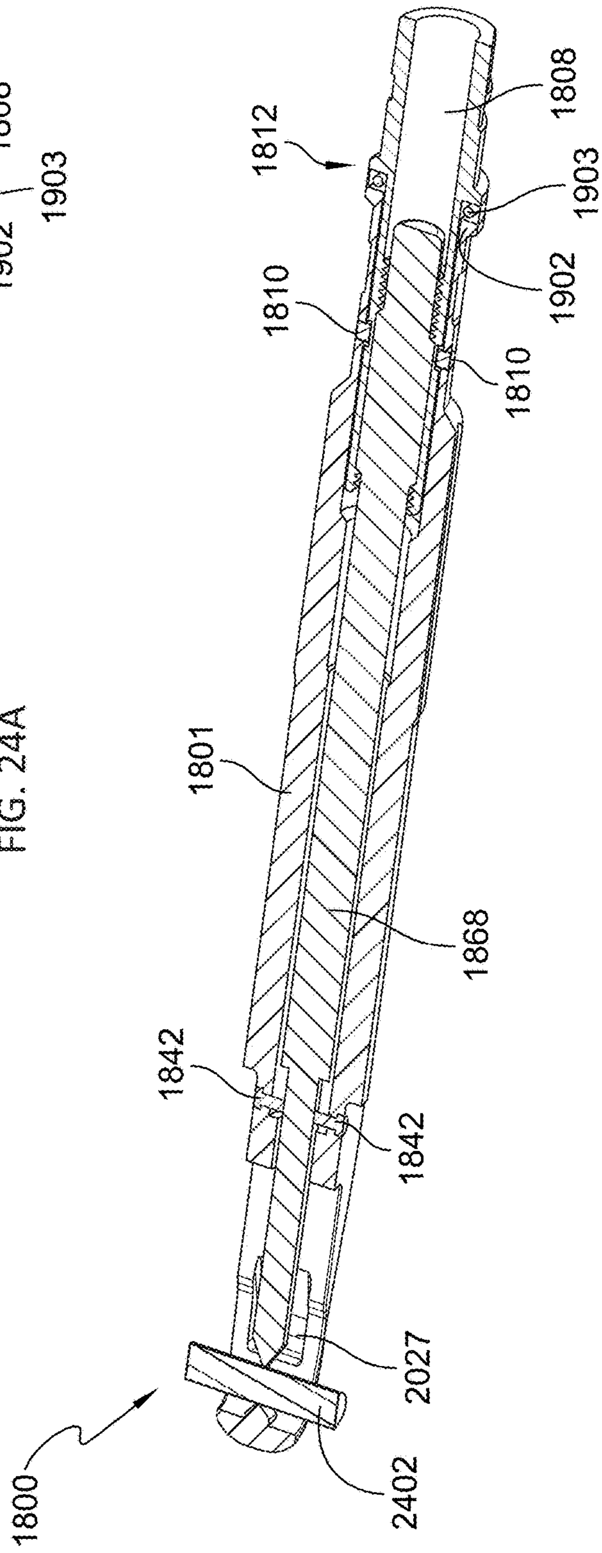
FIG. 24B is another longitudinal cross-sectional view of the cutting instrument of FIG. 18A.

FIGS. 24A and 24B illustrate longitudinal perspective cross-sectional views at perpendicularly offset angles to illustrate the above-described components in an assembled configuration and interfacing with a spinal fixation rod 2402, one example of an implant that can be cut using the instrument 1800.

Figure 25A:
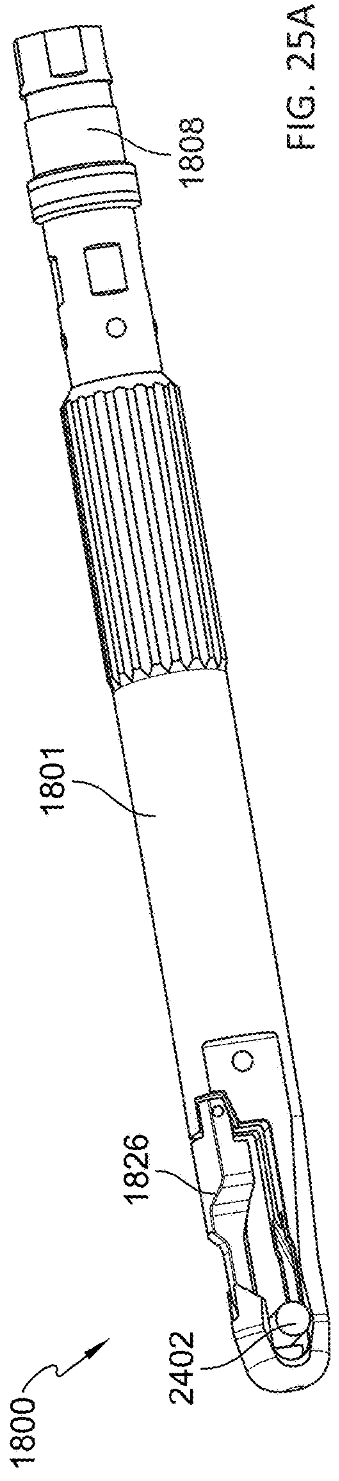
FIG. 25A is a perspective view of the cutting instrument of FIG. 18A in which the anvil is retracted proximally.
Figure 25B:
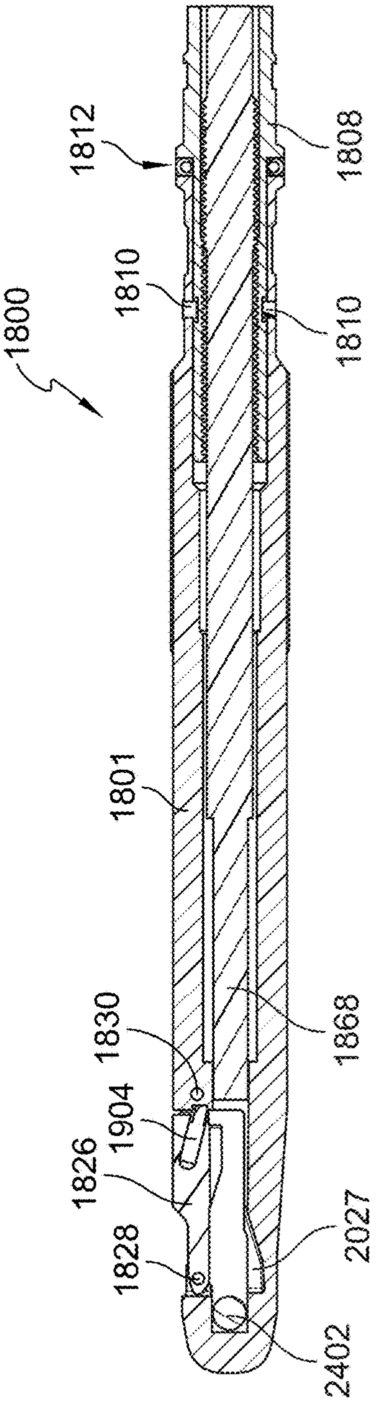
FIG. 25B is a side longitudinal cross-sectional view of the cutting instrument of FIG. 18A in which the anvil is retracted proximally.
Figure 25C:
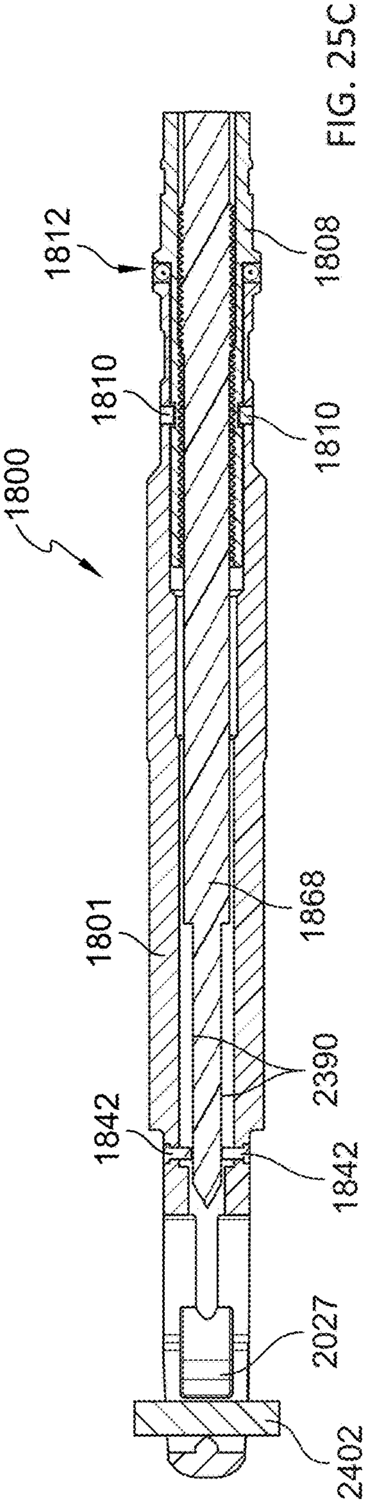
FIG. 25C is a top longitudinal cross-sectional view of the cutting instrument of FIG. 18A in which the anvil is retracted proximally.

FIGS. 25A-28 illustrate use of the instrument 1800. FIGS. 25A-25C, for example, illustrate the instrument 1800 in a configuration wherein the anvil 1868 is retracted proximally such that it does not interfere with operation of the capture arm 1826 and the threads of the inner sleeve 1808 are minimally engaged with the threads of the anvil. In particular, FIG. 25A is a perspective view, FIG. 25B is a side longitudinal cross-sectional view, and FIG. 25C is a top longitudinal cross-sectional view of the instrument 1800. In the illustrated configuration, the capture arm 1826 can pivot freely to expose the opening 2024 and allow an implant to be side-loaded for cutting. The figures show a spinal fixation rod 2402 already loaded and the capture arm 1826 closed such that the instrument 1800 is ready to distally advance the anvil 1868 and perform a cutting operation.

Figure 26A:
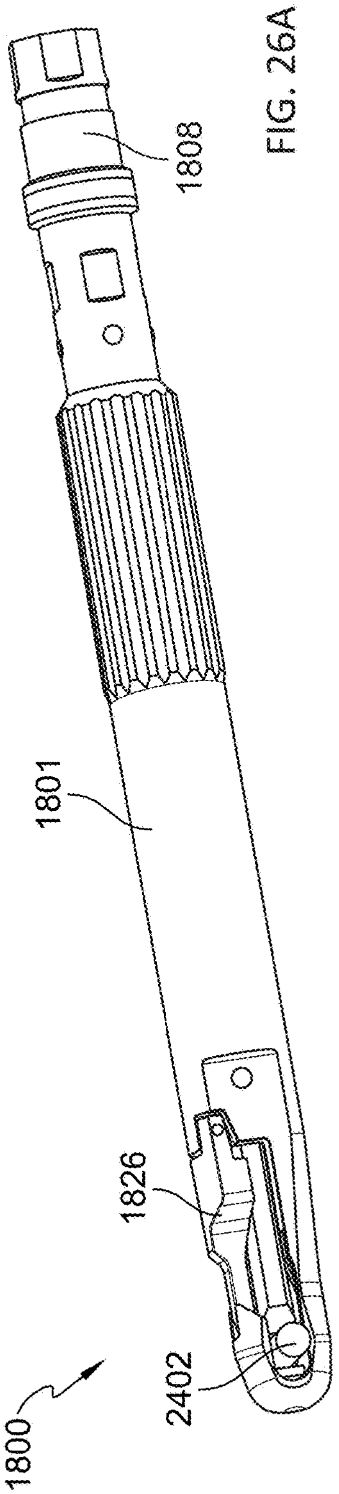
FIG. 26A is a perspective view of the cutting instrument of FIG. 18A in which an anvil is advanced distally.
Figure 26B:
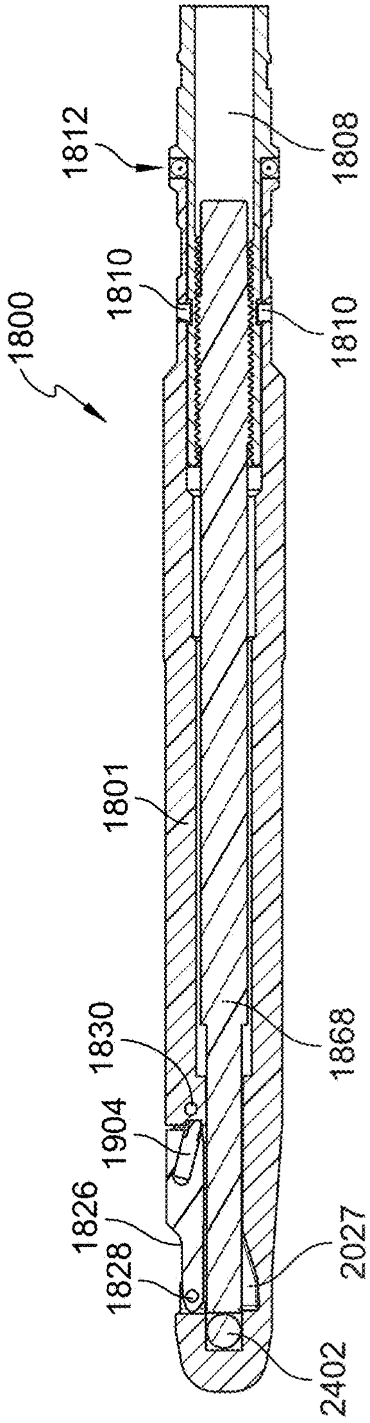
FIG. 26B is a side longitudinal cross-sectional view of the cutting instrument of FIG. 18A in which an anvil is advanced distally.
Figure 26C:
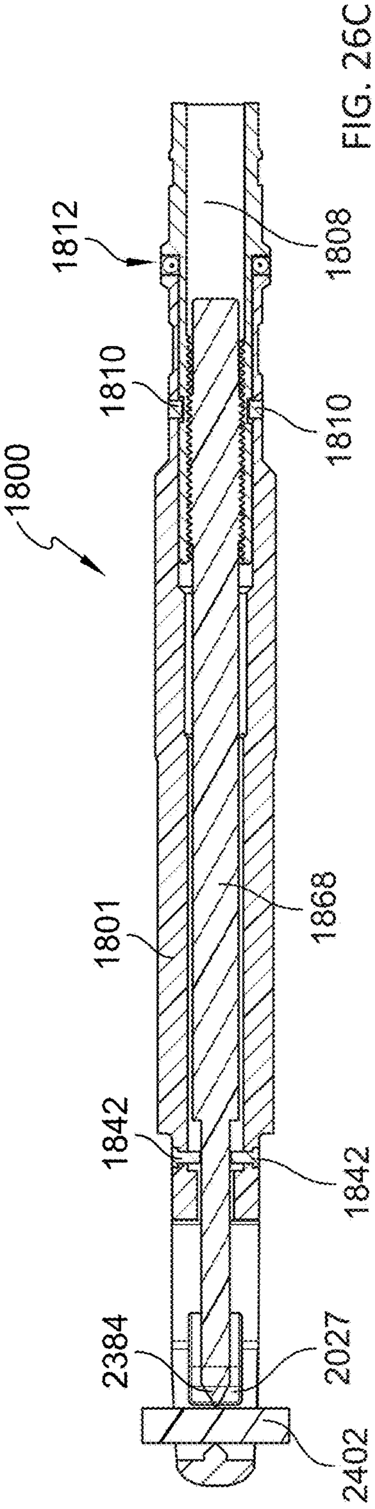
FIG. 26C is a top longitudinal cross-sectional view of the cutting instrument of FIG. 18A in which an anvil is advanced distally.

FIGS. 26A-26C illustrate the instrument 1800 in a configuration where the anvil 1868 is advanced distally relative to the outer sleeve 1801 and inner sleeve 1808 such that a distal cutting tip 2384 of the anvil contacts the rod 2402 that is loaded in the distal end of the outer sleeve. In particular, FIG. 26A is a perspective view, FIG. 26B is a side longitudinal cross-sectional view, and FIG. 26C is a top longitudinal cross-sectional view of the instrument 1800. To move the instrument from the configuration of FIGS. 25A-25C to the configuration of FIGS. 26A-26C, the inner sleeve 1808 can be rotated relative to the outer sleeve 1801. The rotation of the inner sleeve 1808 can cause translation of the anvil 1868 due to the threaded interface between the two components and the keying of the anvil relative to the outer sleeve 1801 via the pins 1842 and the flats 2390 that prevents relative rotation between those components.

Figure 27:
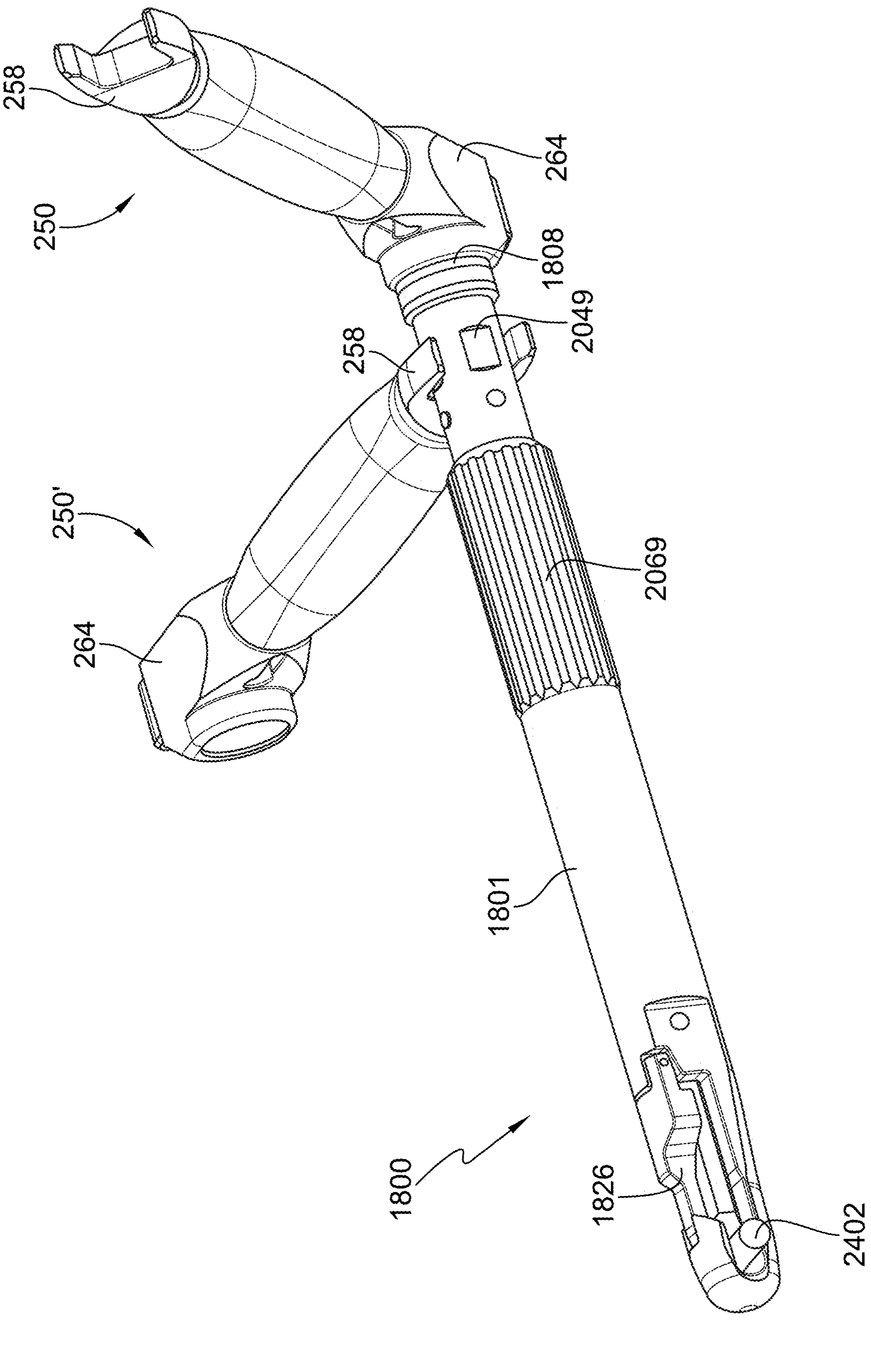
FIG. 27 is a perspective view of a plurality of handles being used to impart torque and counter-torque to the inner and outer sleeve of the cutting instrument of FIG. 18A.
Figure 28:
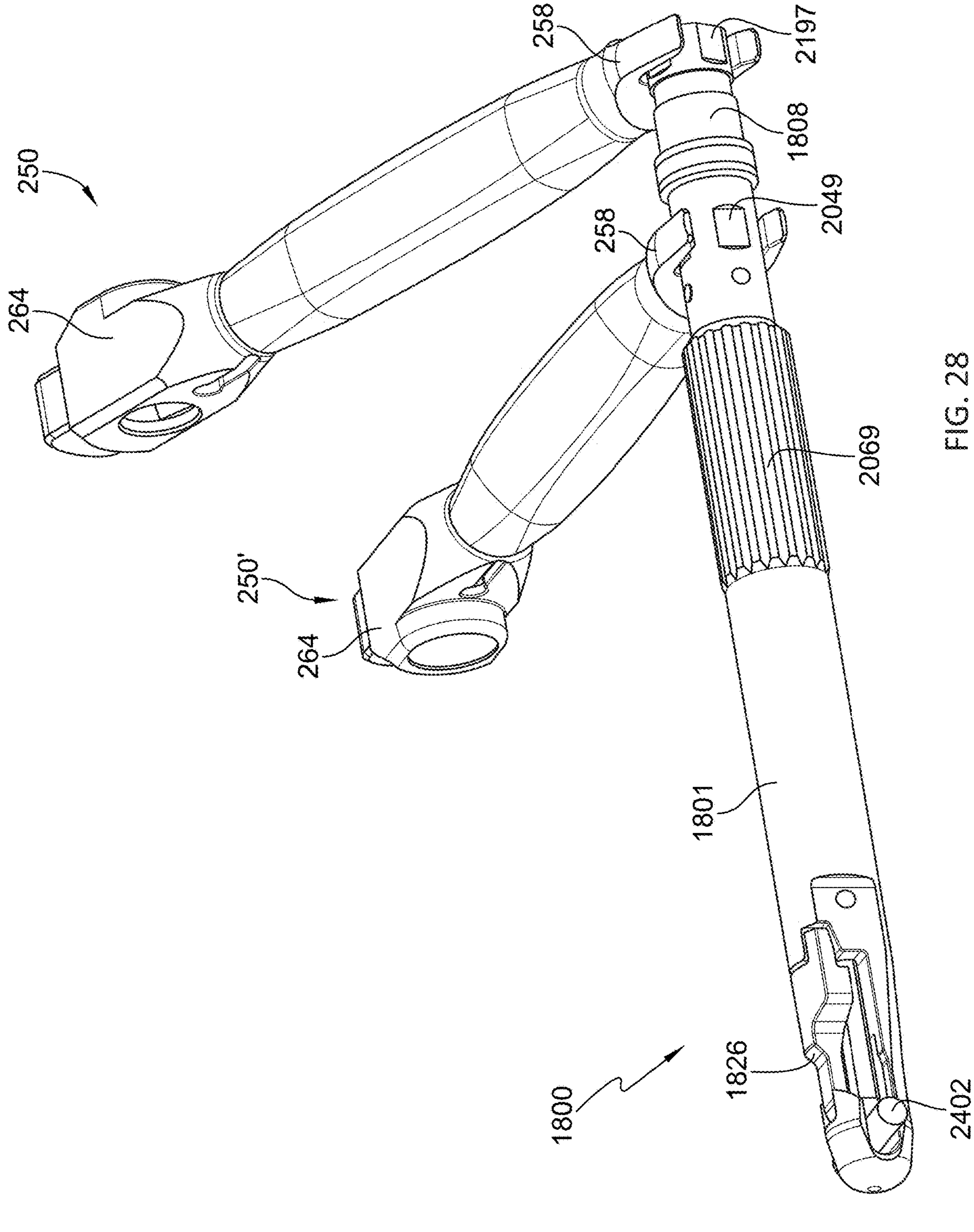
FIG. 28 is another perspective view of a plurality of handles being used to impart torque and counter-torque to the inner and outer sleeves of the cutting instrument of FIG. 18A.

Continued rotation of the inner sleeve 1808 relative to the outer sleeve 1801 to advance the anvil 1868 distally from the configuration shown in FIGS. 26A-26C can sever the implant at the location of contact with the anvil. In some embodiments, rotation of the inner sleeve 1808 relative to the outer sleeve 1801 can be performed manually by hand until resistance is encountered and the anvil is in contact with the implant to be cut. To rotate the inner sleeve 1808 further at that point, additional instruments can be utilized. FIGS. 27 and 28, for example, illustrate the use of two counter-torque handles 250, 250' to apply torque in one direction to the inner sleeve 1808 and counter-torque in the opposite direction to the outer sleeve 1801.

In particular, FIG. 27 illustrates one possible use where a housing or closed end 264 of a first handle 250 is utilized to apply torque to the inner sleeve 1808 via the one or more flats 2197 formed around a proximal end thereof. In addition, a fork or open end 258 of a second counter-torque handle 250' is utilized to apply counter-torque to the outer sleeve 1801 via the one or more flats 2049 formed thereon. In this configuration, the counter-torque handle 250 can be selectively locked to the inner sleeve 1808 via interaction with the groove 2147.

FIG. 28 illustrates another possible use where the forks or open ends 258 of both handles 250, 250' are utilized to impart torque and counter-torque to the inner and outer sleeves 1808, 1801. In other embodiments, alternative driver configurations can be utilized. For example, an alternative manual driver handle, such as a T-handle driver, etc., can be utilized to apply torque to the inner sleeve 1808 and the counter-torque handle 250' can be utilized to apply counter-torque to the outer sleeve 1801. In another embodiment, a powered driver can be utilized to apply torque to the inner sleeve 1808 and the counter-torque handle 250' can be utilized to apply counter-torque to the outer sleeve 1801. In still other embodiments, any of the above-mentioned drivers can be utilized in connection with the inner sleeve 1808 and counter-torque can be applied manually by a user grasping the outer sleeve 1801, such as via the rip grooves 2069 formed on the outer sleeve.

In some embodiments of the instruments described herein, the inner sleeve can include a plurality of threaded portions formed thereon. For example, the inner sleeve can include a first threaded portion and a second, additional threaded portion spaced apart from the first threaded portion. Further, the threads formed on the inner surface of the outer sleeve can be positioned towards a proximal end thereof. This configuration can prevent the inner sleeve from being removed proximally out of the outer sleeve unintentionally, while still enabling complete disassembly from the instrument for cleaning, anvil replacement, etc. In use, the first and second threaded portions of the inner sleeve can be threaded into the outer sleeve to perform a cutting operation as described above. When proximal retraction of the inner sleeve and anvil are desired, however, the spaced-apart threaded portions of the inner sleeve can prevent unintentional separation of the inner sleeve from the outer sleeve. More particularly, the first and second threaded portions of the inner sleeve can be separated by a non-threaded portion. The non-threaded portion can include alternative surface features in some embodiments, such as ribs, nubs, or other features. The presence of the non-threaded portion can allow feedback to a user that they have retracted the inner sleeve to a maximum extent relative to the outer sleeve, as the inner sleeve will translate freely relative to outer sleeve once the first threaded portion is disengaged and the non-threaded portion of the inner sleeve is aligned with the threads of the outer sleeve. To fully disassemble the inner sleeve from the outer sleeve, however, a user will have to both pull proximally on the inner sleeve to translate it relative to the outer sleeve and rotate it relative to the outer sleeve to engage the second threaded portion at a distal end of the inner sleeve with the threads of the outer sleeve. Only once the second threaded portion is fully disengaged from the threads of the outer sleeve can the inner sleeve be completely removed from the outer sleeve. That is, removal of the inner sleeve relative to the outer sleeve is performed with a pull/push force as well as a rotation, which can prevent unwanted back-out of the inner sleeve. Additional details on this type of configuration can be found in U.S. Patent Publication No. 2022/0280207, the entire contents of which are incorporated by reference herein.

Various devices and methods disclosed herein can be used in minimally-invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices disclosed herein can be constructed from any of a variety of known materials. Example materials include those that are suitable for use in surgical applications, including metals such as stainless steel, titanium, titanium nitride, nickel, cobalt, chrome, cobalt-chromium, or alloys and combinations thereof, polymers such as PEEK, ceramics, carbon fiber, and so forth. The various components of the devices disclosed herein can be rigid or flexible. In addition, one or more of the components or devices disclosed herein can be formed as monolithic or unitary structures, e.g., formed from a single continuous material, or can be formed from separate components coupled together in a variety of manners that either facilitate or discourage subsequent separation. One or more components or portions of the device can be formed from a radiopaque material to facilitate visualization under fluoroscopy and other imaging techniques, or from a radiolucent material so as not to interfere with visualization of other structures. Example radiolucent materials include carbon fiber and high-strength polymers. Further, various methods of manufacturing can be utilized, including 3D printing or other additive manufacturing techniques, as well as more conventional manufacturing techniques, including molding, stamping, casting, machining, etc.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly of the device, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device or component, are all within the scope of the present disclosure.

Various devices or components described herein can be processed before use in a surgical procedure. For example, a new or used device or component can be obtained and, if necessary, cleaned. The device or component can then be sterilized. In one sterilization technique, the device or component can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the device or component and in the container. The sterilized device or component can then be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as "at least one of" or "one or more of" may occur followed by a conjunctive list of elements or features. By way of example, "an element" means at least one element and can include more than one element. "About" is used to provide flexibility to a numerical range endpoint by providing that a given value may be "slightly above" or "slightly below" the endpoint without affecting the desired result. The use herein of the terms "including," "comprising," or "having," and variations thereof, is meant to encompass the elements listed thereafter and equivalents thereof, as well as additional elements. As used herein, "and/or" refers to and encompasses any and all possible combinations of one or more of the associated listed items, as well as the lack of combinations where interpreted in the alternative ("or"). Further, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

To the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

The figures provided herein are not necessarily to scale. Still further, to the extent arrows are used to describe a direction of movement, these arrows are illustrative and in no way limit the direction that the respective component can or should be moved. Other movements and directions may be possible to create the desired result in view of the present disclosure.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A surgical instrument, comprising:
   - an outer sleeve having a lumen that extends therethrough;
   - an opening formed in a sidewall of the outer sleeve and configured to receive at least a portion of an implant therethrough;
   - a capture arm disposed within the opening, the capture arm being pivotably coupled to the outer sleeve and configured to selectively expose the opening to allow the implant to pass therethrough; and
   - an inner sleeve disposed in the lumen of the outer sleeve, the inner sleeve being configured to rotate relative to the outer sleeve; and
   - an anvil disposed in the lumen of the outer sleeve distal to the inner sleeve, the anvil being configured to translate without rotating relative to the outer sleeve to cut the implant.
2. The instrument of example 1, wherein the inner sleeve is configured to rotate relative to the outer sleeve to translate the anvil distally with respect to the outer sleeve.
3. The instrument of example 2, wherein the inner sleeve includes a threaded surface on at least a portion thereof that is configured to engage with a corresponding threaded surface on an inner surface of the outer sleeve.
4. The instrument of any of examples 2 to 3, wherein the anvil further comprises a cutting tip at a distal end thereof for cutting the implant.
5. The instrument of example 4, wherein the cutting tip is V-shaped.
6. The instrument of any of examples 1 to 5, wherein the anvil includes a groove formed along a length thereof.
7. The instrument of example 6, further comprising a pin that passes through the outer sleeve and is disposed in the groove of the anvil to prevent rotation of the anvil during translation.
8. The instrument of any of examples 1 to 7, wherein the anvil includes a coating configured to enhance a hardness thereof.
9. The instrument of any of examples 1 to 8, wherein the implant comprises one or more of a spinal rod, a trauma plate, or a CMF plate.
10. The instrument of any of examples 1 to 9, wherein the capture arm is configured to pivot to expose the opening in response to a force applied to the capture arm by the implant.
11. The instrument of any of examples 1 to 10, wherein the capture arm is biased to be disposed within the opening.

12 The instrument of example 11, wherein the capture arm is biased by a spring disposed in a channel formed in the capture arm that exerts a radially outward force onto the capture arm.

13. The instrument of any of examples 1 to 12, further comprising a pocket formed on an inner surface of a sidewall of the pouter sleeve opposite the opening, the pocket being configured to receive the capture arm when the capture arm selectively exposes the opening.
14. The instrument of any of examples 1 to 13, further comprising a counter-torque handle configured to mate with the outer sleeve to prevent rotation of the outer sleeve during rotation of the inner sleeve.
15. The instrument of any of examples 1 to 14, wherein the outer sleeve includes a sharpened edge positioned to contact an implant on an opposite side from the anvil.
16. The instrument of any of examples 1 to 15, wherein a proximal end of the inner sleeve comprises a drive feature configured to couple with a torque application device to facilitate rotation of the inner sleeve.
17. The instrument of any of examples 1 to 16, wherein the outer sleeve includes a base tube and a distal tip configured to be modularly coupled to one another and selectively locked against separation.
18. The instrument of example 17, wherein a distal end of the base tube includes a reduced diameter portion configured to be received within a reduced diameter portion of a proximal end of the distal tip.
19. The instrument of any of examples 17 to 18, wherein the distal tip includes a snap lock configured to interface with a slot of the base tube to selectively lock against separation of the distal tip and base tube.

20 The instrument of any of examples 17 to 19, wherein the opening is formed in the distal tip.

21. The instrument of any of examples 17 to 19, wherein the capture arm is pivotably coupled to the distal tip.
22. The instrument of any of examples 1 to 21, wherein the inner sleeve is configured to translate relative to the outer sleeve.
23. A surgical method, comprising:
    - contacting an implant against a capture arm on a side of a cutting instrument outer sleeve to pivot the capture arm and expose an opening to an implant-receiving portion of the cutting instrument;
    - passing the implant through the opening and into the implant-receiving portion of the cutting instrument; and
    - rotating an inner sleeve of the cutting instrument relative to the outer sleeve to distally translate an anvil through the implant.

24 The method of example 23, further comprising coupling a driver to a proximal portion of the inner sleeve.

25. The method of example 24, wherein the driver is powered and rotating the inner sleeve further comprises actuating the powered driver.

26. The method of any of examples 23 to 25, further comprising coupling a counter-torque handle to the outer sleeve to prevent rotation of the outer sleeve during rotation of the inner sleeve.

27. The method of any of examples 23 to 26, wherein pivoting the capture arm includes passing a distal end of the capture arm into a pocket formed in a sidewall of the cutting instrument opposite the opening.

28 The method of any of examples 23 to 27, further comprising pivoting the capture arm to block the opening after passing the implant through the opening.

29 The method of any of examples 23 to 28, further comprising assembling the outer sleeve by coupling a modular distal tip with a base tube prior to contacting the implant against the capture arm.

30. The method of example 29, wherein coupling the modular distal tip with the base tube further comprises inserting a reduced diameter portion of a distal end of the base tube into a reduced-diameter portion of a proximal end of the distal tip.

31. The method of example 30, wherein coupling the modular distal tip with the base tube further includes rotating the distal tip and base tube relative to one another to engage a lock against separation thereof.

32. The method of any of examples 23 to 31, wherein the implant comprises one or more of a spinal rod, a trauma plate, or a CMF plate.

What is claimed is:

1. A surgical instrument comprising:

an outer sleeve having a lumen;

an opening formed in a sidewall of the outer sleeve and configured to receive at least a portion of an implant therethrough;

a capture arm disposed within the opening, the capture arm being pivotably coupled to the outer sleeve and configured to selectively expose the opening to allow the implant to pass therethrough;

an inner sleeve disposed in the lumen of the outer sleeve, the inner sleeve having a lumen and being configured to rotate relative to the outer sleeve; and an anvil configured to be inserted through the lumen of the inner sleeve to a position that is distal to the inner sleeve, the anvil being configured to translate without rotating relative to the outer sleeve to cut the implant.

2. The instrument of claim 1, wherein the inner sleeve is configured to rotate relative to the outer sleeve to translate the anvil distally with respect to the outer sleeve.

3. The instrument of claim 2, wherein the anvil further comprises a cutting tip at a distal end thereof for cutting the implant.

4. The instrument of claim 3, wherein the cutting tip is V-shaped.

5. The instrument of claim 1, wherein the anvil includes a coating configured to enhance a hardness thereof.

6. The instrument of claim 1, wherein the implant comprises one or more of a spinal rod, a trauma plate, or a craniomaxillofacial (CMF) plate.

7. The instrument of claim 1, wherein the capture arm is biased to be disposed within the opening.

8. The instrument of claim 7, wherein the capture arm is biased by a spring disposed in a channel formed in the capture arm that exerts a radially outward force onto the capture arm.

9. The instrument of claim 1, further comprising a pocket formed on an inner surface of a sidewall of the outer sleeve opposite the opening, the pocket being configured to receive the capture arm when the capture arm selectively exposes the opening.

10. The instrument of claim 1, further comprising a counter-torque handle configured to mate with the outer sleeve to prevent rotation of the outer sleeve during rotation of the inner sleeve.

11. The instrument of claim 1, wherein the outer sleeve includes a sharpened edge positioned to contact an implant on an opposite side from the anvil.

12. The instrument of claim 1, wherein a proximal end of the inner sleeve comprises a drive feature configured to couple with a torque application device to facilitate rotation of the inner sleeve.

13. The instrument of claim 1, wherein the capture arm is configured to pivot to expose the opening in response to a force applied to the capture arm by the implant.

* * * * *